(12) United States Patent
Shi

(10) Patent No.: US 6,409,769 B1
(45) Date of Patent: Jun. 25, 2002

(54) KINETIC RESOLUTION OF OLEFINS

(75) Inventor: Yian Shi, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 09/673,335

(22) PCT Filed: Apr. 16, 1999

(86) PCT No.: PCT/US99/08418
§ 371 (c)(1),
(2), (4) Date: Dec. 4, 2000

(87) PCT Pub. No.: WO99/52886
PCT Pub. Date: Oct. 21, 1999

Related U.S. Application Data

(60) Provisional application No. 60/082,029, filed on Apr. 16, 1998.

(51) Int. Cl.[7] .................. C07D 301/02; C07D 301/12; C07D 301/14; C07D 301/19
(52) U.S. Cl. ............... 649/519; 549/523; 549/525; 549/529; 549/531
(58) Field of Search ............... 549/519, 523, 549/525, 529, 531

(56) References Cited

U.S. PATENT DOCUMENTS

| | | |
|---|---|---|
| 4,902,820 A | 2/1990 | Zoeller |
| 5,403,549 A | 4/1995 | McNeil et al. |
| 5,414,078 A | 5/1995 | Liotta et al. |
| 5,859,265 A | 1/1999 | Müller et al. |
| 6,060,610 A | 5/2000 | Arca et al. |
| 6,160,137 A | 12/2000 | Tsuji |
| 6,160,138 A | 12/2000 | Escrig et al. |
| 6,194,591 B1 | 2/2001 | Grey et al. |
| 6,225,482 B1 | 5/2001 | Drauz et al. |

OTHER PUBLICATIONS

U.S. application No. 09/284,054, Shi, filed Apri. 6, 1999.
U.S. application No. 09/534,419, Shi, filed Mar. 23, 2000.
U.S. application No. 09/663,390, Shi, filed Aug. 10, 2000.
Tu et al., *J. Am. Chem. Soc.*, 1996, 118, p. 9806–9807.
Wang et al., *J. Am. Chem. Soc.*, 1997, 119, p. 11224–11235.
Wang et al., *J. Org. Chem.*, 1997, 62, p. 2328–2329.
Wang e tal., *J. Org. Chem.*, 1997, 62, p. 8622–8623.
Kurihara et al., *Tet. Lett.*, 1994, 35, p. 1577–1580.
Denmark et al., *J. Org. Chem.*, 1995, 60, p. 1391–1407.
Cicala et al., *J. Org. Chem.*, 1982, 47, p. 2670–2673.
Curci et al., *J. Org. Chem.*, 1980, 45, p. 4758–4760.
Besse et al., *Tetrahedron*, 1994, 50, p. 8885–8927.
Curci et al., *J. Chem. Soc.*, 1984, p. 155–156.
Curci et al., *Tet. Lett.*, 1995, 36, p. 5831–5834.
Brown et al., *Tetrahedron*, 1995, 51, p. 3587–3606.
Denmark et al., *J. Org. Chem.*, 1997, 62, p. 8288–8289.
Yang et al., *J. Am. Chem. Soc.*, 1996, 118, p. 491–492.
Yang et al., *J. Am. Chem. Soc.*, 1996, 118, p. 11311–11312.
Armstrong et al., *Tetrahedron: Asymmetry*, 1997, 8, 1677–1684.
Song et al., *Tetrahedron: Asymmetry*, 1997, 8, p. 2921–2926.
Aggarwal et al., *Chem. Commun.*, 1996, p. 191–192.
Davis et al., *Tet. Lett.*, 1986, 27, p. 5079–5082.
Ebrahim et al., *Tetrahedron: Asymmetry*, 1997, 8, p. 3163–3173.
Kroutil et al., *J. Chem. Soc., Perkin Trans. I*, 1996, p. 2837–2844.
Kroutil et al., *Chem. Commun.*, 1996, p. 845–846.
Itsuno et al., *J. Org. Chem.*, 1990, 55, p. 6047–6049.
Tipson et al., *Carbohyd. Res.*, 1971, 16, p. 383–393.
DuPenhoat et al., *Carbohyd. Res.*, 1971, 71, p. 135–148.
Chughtal et al., Abstracts, 1996, 21th ACS National Meetings, Am. Chem. Soc.
Schulz et al., *J. Org. Chem.*, 1997, 62, p. 188–193.
Payne, *Tetrahedron*, 1962, 18, p. 763–765.
McDonald, *Mech.,Mol. Migr.*, 1971, 3, p. 67.
Soloway et al., *J. Am. Chem. Soc.*, 1954, 76, p. 2941.
Feng et al., *J. Am. Chem. Soc.*, 1999, 121, p. 11002.
Zhu, *J. Org. Chem.*, 2001, 66, p. 1818.
Williamson et al., *J. Org. Chem.*, 1967, 3(12), p. 3937–7.
Adam et al., *J. Am. Chem. Soc.*, 1998, 120, p. 708–714.

*Primary Examiner*—Ba K. Trinh
(74) *Attorney, Agent, or Firm*—Townsend and Townsend and Crew LLP

(57) ABSTRACT

A method for kinetically resolving a stereoisomer mixture of compounds using asymmetric epoxidation is provided. Compounds contain an olefin moiety providing one stereoisomer to be epoxidized at a higher rate than the other stereoisomer using a chiral ketone and an oxidizing agent.

64 Claims, 5 Drawing Sheets

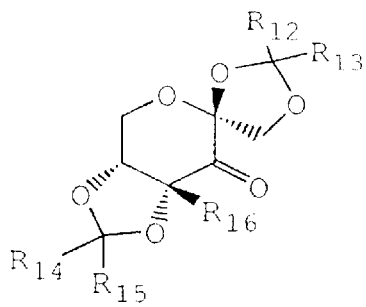
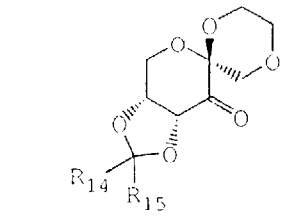

| $R_{12}, R_{13}$ | $R_{14}, R_{15}$ | $R_{16}$ |
|---|---|---|
| Me, Me | Me, Me | H |
| Me, Me | Et, Et | H |
| Me, Me | Et, H | H |
| Me, Me | Ph, H | H |
| Me, Me | i-Pr, H | H |
| Me, Me | -(CH$_2$)$_4$- | H |
| Me, Me | -(CH$_2$)$_5$- | H |
| Me, Me | Bn, Bn | H |
| Et, Et | Et, Et | H |
| Et, Et | Me, Me | H |
| -(CH$_2$)$_4$- | -(CH$_2$)$_4$- | H |
| -(CH$_2$)$_4$- | Me, Me | H |
| -(CH$_2$)$_4$- | -(CH$_2$)$_5$- | H |
| -(CH$_2$)$_4$- | Me, Me | H |
| -(CH$_2$)$_4$- | -(CH$_2$)$_6$- | H |
| Me, Me | Me, Me | CH$_2$OH |

| $R_{14}, R_{15}$ |
|---|
| Me, Me |
| Et, Et |
| Pr, Pr |
| Ph, Ph |
| Bn, Bn |
| -(CH$_2$)$_5$- |
| -(CH$_2$)$_4$- |

| $R_{17}$ | $R_{18}$ | $R_{16}$ |
|---|---|---|
| MeO | H | H |
| MeO | H | CH$_2$OTs |
| ClCH$_2$CH$_2$O | H | H |
| ClCH$_2$CH$_2$O | CH$_2$OH | H |
| ClCH$_2$CH$_2$O | CH$_2$OAc | H |
| ClCH$_2$CH$_2$O | CH$_2$OTBS | H |

Fig. 4

KINETIC RESOLUTION OF OLEFINS

This application is a 371 of PCT/US99/08418 dated Apr. 16, 1999 which claims the benefit of provisional application 60/082,029 dated Apr. 16, 1998.

STATEMENT REGARDING FEDERALLY FUNDED RESEARCH

The U.S. government has a paid up license in this invention and the right in limited circumstances to require the patent owner to license others on reasonable terms as provided for by the terms of Grant No. GM-55704-01 awarded by National Institute of Health.

FIELD OF THE INVENTION

The present invention is directed to a method for resolving a stereoisomer mixture of a compound containing an olefin moiety using a chiral ketone mediated kinetic resolution.

BACKGROUND OF THE INVENTION

The stereochemistry of a molecule is important in many of the properties of the molecule. For example, it is well known that physiological properties of drugs having one or more chiral centers, i.e., stereochemical centers, depend on the stereochemistry of a drug's chiral center. In addition, properties of a polymer containing a chiral monomeric unit depend on the enantiomeric purity of the monomer.

Although there are many asymmetric chemical reactions which produce enantiomerically enriched products, the scope of these reactions are limited. Separation of a stereoisomeric mixture (e.g., racemic or geometric isomers; of a compound is often difficult and/or a time-consuming task. One method of separating (or enriching) a racemic mixture of a compound is to react the racemic mixture with a chiral compound to produce diastereoisomers which may be physically separated, e.g., by chromatography, distillation or crystallization.

Many enzymatic methods are also available for separating stereoisomers of compounds containing one or more hydroxy groups. In addition, a kinetic resolution method for allylic alcohols is also available. For example, enrichment of one particular stereoisomer in a racemic allylic alcohol mixture can be achieved by using titanium catalyzed asymmetric epoxidation to convert predominantly one of the allylic alcohol stereoisomer to an epoxide.

Despite the availability of these and other methods for resolving a stereoisomeric mixture of compounds, there is a need for a method for resolving a variety of stereoisomer mixtures of compounds containing at least one olefin moiety. There is also a need for a method for resolving a stereoisomer mixture of compounds which does not contain an allylic alcohol functional group.

SUMMARY OF THE INVENTION

Present invention provides a method for increasing a relative concentration of at least one stereoisomer of a compound having at least one olefinic moiety, from the stereoisomer mixture. The method generally involves converting one of the stereoisomers of the compound to an epoxide at a higher rate than the conversion of the other stereoisomer.

The method of the present invention involves contacting an oxidizing agent with a mixture of a chiral ketone and a stereoisomer mixture of the compound to epoxidize the olefinic moiety of the compound. Epoxidation of one stereoisomer of the compound occurs at a relatively higher rate than epoxidation of the other stereoisomer resulting in a relative increase in the concentration of the other stereoisomer.

The chiral ketone is selected from the group consisting of compounds of the formula:

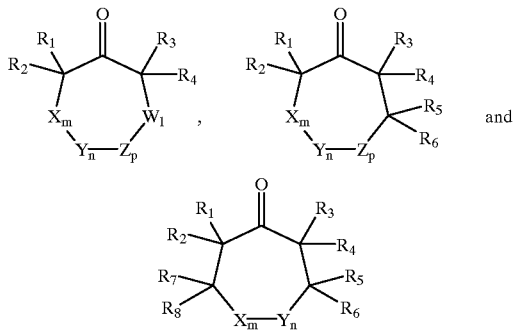

wherein
each of W, X, Y and Z is independently $CR_9R_{10}$, O, $NR_{11}$, $NR_{11}R_{12}$, S, Se, Si or P;
each of l, m, n and p is independently an integer from 0 to 3;
each of $R_1$, $R_2$, $R_3$, $R_4$, $R_5$, $R_6$, $R_7$, $R_8$, $R_9$ and $R_{10}$ is independently hydrogen, halide, hydroxyl, nitro, thio, or alkyl, alkoxy, aryl, silyl, siloxy, carbonyl, carboxylate, ester, amino, sulfinyl, sulfonyl, sulfate, sulfite, phosphate or phosphite groups containing from 1 to about 20 carbon atoms, or two or more $R_1$, $R_2$, $R_3$, $R_4$, $R_5$, $R_6$, $R_7$, $R_8$, $R_9$ and $R_{10}$ are linked to form (i.e., together forms) 3 to about 10 membered cyclic moiety containing 1 to about 20 carbon atoms; and
each of $R_{11}$ and $R_{12}$ is hydrogen, oxygen or alkyl, sulfonyl, alkoxy or carbonyl groups containing from 1 to about 20 carbon atoms, or $R_{11}$ and $R_{12}$ are linked to form (i.e., together forms) 3 to about 10 membered cyclic moiety containing 1 to about 20 carbon atoms.

Preferably a chiral ketone is selected from the group consisting of the compound of the formula:

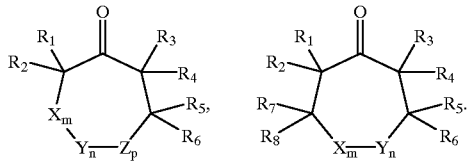

wherein preferably, m is 0, Y is O or $CR_9R_{10}$, n and p are 1, and Z is $CR_9R_{10}$.

Preferably two or more $R_1$, $R_2$, $R_3$, $R_4$, $R_5$, $R_6$, $R_7$, $R_8$, $R_9$ and $R_{10}$ are linked to form 3 to about 10 membered cyclic moiety containing 1 to about 20 carbon atoms, more preferably $R_1$ and $R_2$ are linked to form a moiety of the formula:

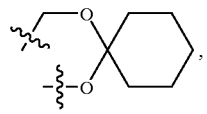

$-O-C(CH_2CH_3)_2-O-CH_2-$ or $-O-C(CH_3)_2-CH_2-$. Alternatively, $R_1$ and $R_7$ are linked to form a moiety of the formula —O—C(CH$_3$)$_2$—O—, —O—C(CH$_2$CH$_3$)$_2$—O—, or —C(CH$_3$)$_2$—.

Preferably R$_3$ and R$_6$ are linked to form a moiety of the formula —O—C(CH$_3$)$_2$O— or a moiety of the formula —O— C(CH$_2$CH$_3$)$_2$O—.

Preferably R$_4$, R$_5$, R$_9$ and R$_{10}$ are independently hydrogen, halide or alkoxy, carboxyl or alkyl groups having 1 to about 20 carbon atoms. More preferably, R$_4$, R$_5$ and R$_{10}$ are hydrogen and R$_9$ is hydrogen, halide, or alkoxy, carboxyl, sulfinyl or alkyl groups having 1 to about 20 carbon atoms.

Preferably the chiral ketone is derived from a carbohydrate, quinic acid or carvone. More preferably the ketone is derived from a group consisting of carvone, inositol, quinic acid, (D)-fructose, (L)-fructose, (D)-arabinose, (L)-arabinose and (L)-sorbose.

In a particular embodiment of the present invention, the chiral ketone is a compound of the formula:

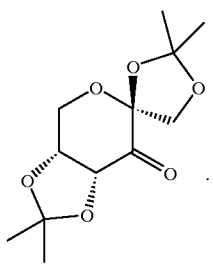

Preferably the oxidizing agent selected from the group consisting of peracids, hydrogen peroxide, sodium hypochlorite, potassium peroxomonosulfate, sodium perborate, tetrabutylammonium monopersulfate and hypofluoride (HOF). More preferably, the oxidizing agent is potassium peroxomonosulfate.

Preferably the pH of the mixture during the epoxidation reaction is from about pH 5 to about pH 14, more preferably from about pH 10 to about pH 14, and most preferably from about pH 10 to about pH 12.

The pH of the mixture is adjusted by adding a base. Useful bases include carbonates, bicarbonates, hydroxides, borates and phosphates. Preferably, the base is selected from the group consisting of potassium carbonate, potassium bicarbonate, sodium bicarbonate, sodium carbonate, sodium hydroxide, sodium borate, sodium phosphate, potassium phosphate, potassium hydroxide, tetraalkylammonium hydroxide, and mixtures thereof.

BRIEF DESCRIPTION OF THE DRAWINGS

FIG. 4 shows a variety of chiral ketones prepared from fructose and arabinose which are useful in kinetic resolution of olefins as described in the present invention;

DETAILED DESCRIPTION OF THE INVENTION

Figure 1:
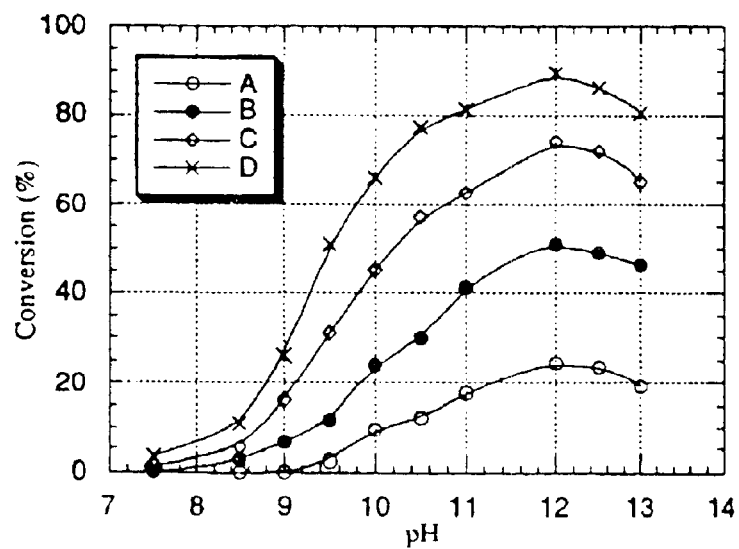
FIG. 1 is a plot of % conversion of trans-β-methylstyrene against pH of the epoxidation reaction using 3 equivalents of acetone as the catalyst in H$_2$O—CH$_3$CN (1:1.5, v/v) solvent system at different time intervals.

The present invention provides a method for increasing a relative concentration of at least one stereoisomer of a compound from a stereoisomer mixture of the compound. A "stereoisomer" refers to any group of compounds having the same molecular formula and the same linkages of bonded atoms but differ in their spatial arrangement. Exemplary stereoisomers includes geometric somers (e.g., cis- or trans-olefins), diastereomers and enantiomers. Thus, methods of the present invention can be used to enrich (i.e., increase a relative concentration of) a geometric isomer, a diastereomer or an enantiomer. Preferably, the method of the present invention enriches a diastereomer or an enantiomer.

Compounds of the present invention contain at least one olefinic moiety. Preferably, compounds of the present invention contain at least one chiral center. A chiral center (i.e., stereochemical center, or stereogenic center) is, of course, an atom to which four different groups are attached; however, the ultimate criterion of a chiral center is nonsuperimposability on the mirror image. Preferably, the chiral center of the compound is spatially in close proximity to the olefinic moiety which undergoes epoxidation by the method of the present invention. In this manner, the chiral center of the compound influences the rate of epoxidation of the olefin moiety by, among others, its interaction with the chiral center(s) of the chiral ketone.

The method of the present invention is based on the observation by the present inventors that the rate of asymmetric epoxidation of compounds using a chiral ketone is influenced by the chiral center that is present on compounds near the reactive olefin moiety, i.e., the olefin moiety which is epoxidized in the reaction. Chiral ketones which are useful in asymmetric epoxidation of the compounds are disclosed in commonly assigned PCT Patent Application No. PCT/US97/18310 filed on Oct. 8, 1997, entitled "Catalytic Asymmetric Epoxidation", which is incorporated herein by reference in its entirety. Asymmetric synthetic reactions, facial selective reactions, stereoselective reactions, or enantioselective reactions are those in which one of a set of stereoisomers is formed exclusively or predominantly.

The method of the present invention generally involves converting one of the stereoisomer of the compound to an epoxide at a higher rate than the other isomer, i.e., a selective epoxidation of one stereoisomer, which results in a relative enrichment of the other stereoisomer. This type of stereoisomer enrichment is referred herein as a "kinetic resolution." The terms "enrichment" and "relative enrichment" are used herein interchangeably to describe an increase of one stereoisomer relative to the other. It should be appreciated that enrichment is a result of a decrease in the amount of one stereoisomer by conversion to an epoxide.

Kinetic resolution methods of the present invention involve contacting an oxidizing agent with a mixture of a chiral ketone and the stereoisomer mixture of the compound to epoxidize the olefinic moiety of the compound. It is believed that a reaction between the oxidizing agent and the chiral ketone produces a dioxirane intermediate which epoxidizes the olefin moiety of the compound.

A "chiral ketone" refers to a chiral compound having a ketone functional group. In order to provide kinetic resolution of compounds, chiral ketones of the present invention are enantiomerically enriched, i.e., have enantiomeric excess of greater than zero. Preferably, chiral ketones used in methods of the present invention have enantiomeric excess of at least about 80%, more preferably at least about 90%, and most preferably at least about 95%. It should be appreciated that although some of the chemical structures in the present invention do not have the identity of specific stereocenter(s) indicated, the chiral ketones of the present invention are enantiomerically enriched as described above. As such, all possible variations of a stereocenter(s) is intended to be included in the scope of the present invention.

Selectivity and reactivity are two important factors that need to be considered in searching for an effective chiral ketone. Ketones containing the following general features are particularly desirable: (1) having one or more stereocenter(s) close to the reacting center, resulting in efficient stereochemical communication between substrates (i.e., the olefins) and the catalyst; (2) having a fused ring or a quaternary center (i.e, fully substituted carbon atom) α to the carbonyl group to minimize the epimerization of the stereogenic centers; (3) controlling possible competing approaches of an olefin to the reacting dioxirane by sterically blocking one face or using a $C_2$ or pseudo $C_2$ symmetric element. As used in this invention, a "face" means a plane or a direction in which the olefin approaches the dioxirane.

Although the method of the present invention can be used to resolve a variety of stereoisomers of compounds, such as geometric isomers, diastereomers and enantiomers, the present invention will now be described in detail with respect to resolving a racemic mixture of compounds, i.e., a mixture that is composed of equal amounts of enantiomers.

The method of the present invention generally includes epoxidation of an olefin moiety of a compound by contacting an oxidizing agent with a mixture of a chiral ketone and a stereoisomer mixture of the compound.

As used in this invention, an "olefin" or "olefin moiety" refers to a compound or a moiety having an alkene functionality, i.e., a double bond between two carbon atoms. It should be appreciated that a compound can have more than one olefin, i.e., double bond, moiety. If more than one olefin is present in the compound, the double bonds can be conjugated or non-conjugated. The olefin can be monosubstituted, di-substituted, tri-substituted or fully substituted. By substituted, it is meant that the olefinic carbon atom is attached to an atom other than hydrogen atom. For example, the olefinic carbon can be substituted with a halogen atom, silicon atom, another carbon atom, oxygen atom, sulfur atom and/or a metal atom such as lithium, sodium or magnesium. The di-substituted olefin moiety can be geminal, cis-, or trans-substituted olefin moiety. Generally for olefins having at least three substituent groups, trans-olefin designation refers to the trans relationship between the larger substituents attached to the two different olefinic carbon atoms, whereas cis designation refers to the cis relation between the larger substituents. In addition to cis- and trans- notation an "E" or "Z" notation can used to denote the relative priority of the substituent groups. E- and Z- notations denoting the stereoisomers of alkenes are well known to one of ordinary skill in the art.

Without being bound by a theory, it is believed that contacting an oxidizing agent to a chiral ketone produces a chiral dioxirane. Although the chiral dioxirane may be isolated under certain conditions, typically it is generated and used in situ by contacting (i.e, reacting) a chiral ketone with an oxidizing agent. It is believed that the reaction between the olefin and the dioxirane produces an epoxide and regenerates the chiral ketone; therefore, the chiral ketone can be used as a catalyst. In addition, less than one equivalent of the chiral ketone, relative to the olefin, can be used in the method of the present invention.

The same molecule of chiral ketone can be used more than once in epoxidizing olefins. The average number of epoxidation of olefins by a chiral ketone molecule is known as a catalytic turn-over rate, or simply a turn-over rate. Preferably the chiral ketones of the present invention have a turn-over rate of at least about 3, more preferably at least about 50 and most preferably at least about 100. Moreover, since the chiral ketones have such a high turnover rate, the amount of the chiral ketones required to resolve stereoisomer of compounds can be less than the stoichiometric amount, i.e., less than one equivalent, of the compound. Moreover, in a racemic mixture there is an equal amount of enantiomers, i.e., 50-50 mixture of enantiomers; therefore, about 1 equivalents or less of the chiral ketone can be used. Preferably about 0.5 equivalents or less of the chiral ketone is used in the methods of the present invention, more preferably about 0.3 equivalents or less, and most preferably about 0.1 equivalents or less.

The chiral ketones which are useful in the method of the present invention are preferably cyclic chiral ketones having at least 3 carbon atoms in the cyclic system, more preferably at least about 4 carbon atoms, and most preferably at least about 5 carbon atoms. Cyclic compounds (or moieties) refer to compounds (or moieties) having a chain of atoms that does not have a terminal portion, i.e, a ring of atoms. The atoms in a cyclic compound (or moiety) can be all carbon atoms, or can be a chain of carbon atoms which can be interrupted by an oxygen atom, sulfur atom, nitrogen atom, silicon atom, phosphorus atom, and/or any other multivalent atoms. Although a $C_2$-symmetry can be present in the cyclic chiral ketone, a presence of a $C_2$-symmetry on the cyclic chiral ketone is not required for the present invention.

In one embodiment of the present invention, the chiral ketone is selected from the group consisting of compounds of the formula:

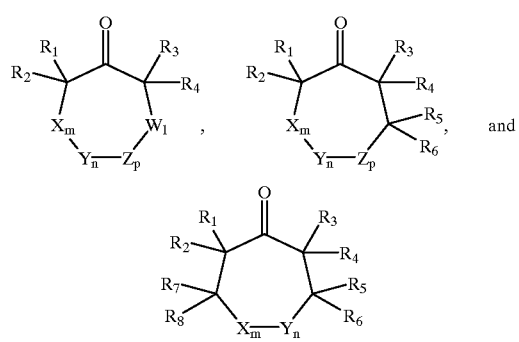

wherein
each of W, X, Y and Z is independently $CR_9R_{10}$, O, $NR_{11}$, $NR_{11}R_{12}$, S, Se, Si or P;
each of 1, m, n and p is independently an integer from 0 to 3;
each of $R_1$, $R_2$, $R_3$, $R_4$, $R_5$, $R_6$, $R_7$, $R_8$, $R_9$ and $R_{10}$ is independently hydrogen, halide, hydroxyl, nitro, thio, or alkyl, alkoxy, aryl, silyl, siloxy, carbonyl, carboxyl, ester, amino, sulfinyl, sulfonyl, sulfate, sulfite, phosphate or phosphite groups containing from 1 to about 20 carbon atoms; and each of $R_{11}$ and $R_{12}$ is hydrogen, oxygen or alkyl, sulfonyl, alkoxy or carbonyl groups containing from 1 to about 20 carbon atoms or $R_{11}$ and $R_{12}$ are linked to form (i.e., together form) 3 to about 10 membered cyclic moiety containing 1 to about 20 carbon atoms.

Alternatively, two or more $R_1$, $R_2$, $R_3$, $R_4$, $R_5$, $R_6$, $R_7$, $R_8$, $R_9$ and $R_{10}$ are linked to form (i.e., together form) 3 to about 10 membered cyclic moiety containing 1 to about 20 carbon atoms. For example, $R_3$ and $R_5$ can be linked to form a moiety of the formula —O—C(CH$_3$)$_2$—O—, or $R_3$ and $R_4$ can be linked to form a moiety of the formula —O—C(CH$_2$CH$_3$)$_2$—O—(CH$_2$)—. More preferably $R_1$, $R_2$, $R_3$, $R_4$, $R_5$, $R_6$, $R_7$, $R_8$, $R_9$ and $R_{10}$ are independently hydrogen, halide, or alkoxy, siloxy, carboxyl, or sulfonyl groups having 1 to about 20 carbon atoms, or two or more $R_1$, $R_2$, $R_3$, $R_4$, $R_5$, $R_6$, $R_7$, $R_8$, $R_9$ and $R_{10}$ are linked to form a from about three to about six-membered cyclic moiety.

Chiral cyclic ketones can be derived from any appropriate starting materials such as carbohydrates, carvone, inositol, and quinic acid. In a particular embodiment of the present invention, a carbohydrate-derived chiral ketone is used as an epoxidation catalysts. Reasons for selecting these ketones as catalysts include (a) carbohydrates are chiral and readily available; (b) they are highly substituted with oxygen groups, which would be good for reactivity, as the inductive effect of oxygen activates the ketone catalyst; and (c) carbohydrate-derived ketones could have rigid conformations because of the anomeric effect, which is desirable for selectivity. Preferably, the chiral cyclic ketone is derived from an oxidation of an unprotected hydroxy group of a carbohydrate compound having at least one protected hydroxy group.

As used in the present invention, a carbohydrate is a sugar molecule or its derivative. A carbohydrate can be monosaccharide or polysaccharide. Exemplary carbohydrates include glucose, fructose, maltose, lactose, mannose, sorbose, ribose, xylose, rhamnose, galactose, talose, arabinose, gulose, sucrose, cellobiose, cellulose, maltonic acid, heparin, chondroitin sulfate, amylose and amylopectin.

Examples of many of the possible hydroxy protecting groups can be found in *Protective Groups in Organic Synthesis*, 2nd edition, T. H. Greene and P. G. M. Wuts, John Wiley & Sons, New York, 1991, which is incorporated herein by reference in its entirety. Preferably a hydroxy protecting group is selected from the group consisting of silyl ethers, ethers, acetals, ketals, esters, ortho esters, sulfonates, phosphates and mixtures thereof. A protecting group for two or more hydroxy groups of the carbohydrate or its derivative can be interconnected. For example, an acetonide group protecting 4,5-hydroxy groups of fructose can be considered to be "two interconnected acetal protecting groups" since they protect two hydroxy groups on the fructose. The oxidation of a hydroxy group of a carbohydrate to form a carbonyl group is well known to one skilled in the art. See Mio et al. *Tetrahedron* 1991, 47, 2133–2144. For example, pyridinium chlorochromate (PCC), pyridinium dichromate (PDC), Swern oxidation condition or other oxidizing conditions can be used to oxidize a hydroxy group of a carbohydrate or its derivative to a ketone compound of the present invention. Preferably, a carbohydrate is selected from the group consisting of fructose, sorbose arabinose, mannose and glucose. More preferably, a carbohydrate is selected from the group consisting of (D)-fructose, (L)-fructose (L)-sorbose, (L)-arabinose and (D)-arabinose.

Preferably, a chiral ketone is selected from the group consisting of a compound of the formula:

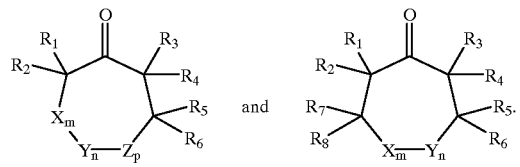

Preferably, m is 0, Y and Z are independently O or $CR_9R_{10}$, and n and p are 1.

Preferably, two or more $R_1$, $R_2$, $R_3$, $R_4$, $R_5$, $R_6$, $R_7$, $R_8$, $R_9$ and $R_{10}$ are linked to form 3 to about 10 membered cyclic moiety containing 1 to about 20 carbon atoms.

Preferably, $R_1$ is linked with $R_2$ or $R_7$ to form a three, five or six-membered cyclic moiety. When $R_1$ and $R_2$ are linked, preferably the linkage forms a moiety of the formula:

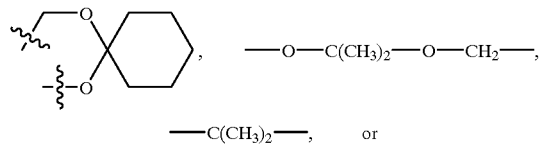

—O—C(CH$_3$)$_2$—O—CH$_2$—, —C(CH$_3$)$_2$—, or —O—C(CH$_2$CH$_3$)$_2$—O—CH$_2$—.

When $R_1$ and $R_7$ are linked, preferably the linkage forms a moiety of the formula —O—C(CH$_3$)$_2$—O— or —O—C(CH$_2$CH$_3$)$_2$—O—CH$_2$—.

Preferably, $R_3$ and $R_6$ are linked to form a five-membered cyclic moiety, and most preferably $R_3$ and $R_6$ are linked to form a moiety of the formula —O—C(CH$_3$)$_2$—O—, —C(CH$_3$)$_2$— or —O—C(CH$_2$CH$_3$)$_2$—O—CH$_2$—. Preferably $R_4$, $R_5$, $R_9$ and $R_{10}$ are independently hydrogen, or alkoxy, carboxyl, sulfonyl or alkyl groups having 1 to about 20 carbon atoms.

When both Y and Z are $CR_9R_{10}$, preferably one $R_9$ is hydrogen and the other $R_9$ is hydrogen, halide, alkyl or alkoxy group containing 1 to about 20 carbon atoms, more preferably 1 to about 10 carbon atoms, and most preferably 1 to about 6 carbon atoms.

In a particular embodiment of the present invention, the chiral ketone is a compound of the formula:

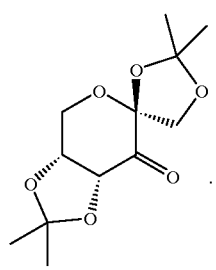

As used in this invention, a moiety of the formula does not include atoms which are directly part of the parent structure. Thus, for example, a chiral compound of the formula:

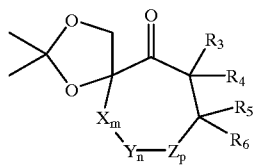

can be alternatively be described as a compound of the formula:

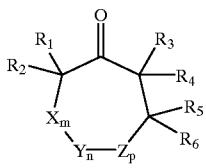

with $R_1$ and $R_2$ together forming a moiety of the formula —O—C(CH$_3$)$_2$—O—(CH$_2$)—.

Alkyl groups according to the present invention are aliphatic hydrocarbons which can be straight or branched carbon atom chain groups. Alkyl groups optionally can be substituted with one or more substituents, such as halo, aryl, hydroxy, alkoxy, carboxy, oxo and cycloalkyl. There may be optionally inserted along the alkyl group one or more oxygen, sulfur or substituted or unsubstituted nitrogen atoms. Exemplary alkyl groups include methyl, ethyl, i-propyl, n-butyl, t-butyl, n-pentyl, heptyl, octyl, hydroxymethyl, hydroxy ethyl, chloromethyl, aminomethyl and dimethylaminomethyl.

Although the dioxirane can be generated in a separate reaction mixture prior to contacting with the compound, it is more advantageous to combine the chiral ketone and the compound in a single reaction mixture to generate the dioxirane in situ by adding an oxidizing agent. It should be appreciated that in situ generation of dioxirane from the chiral ketone generally requires the oxidizing agent to be more reactive towards the chiral ketone than the compound to avoid competing oxidation of the compound by the oxidizing agent.

It should be appreciated that in the method of the present invention, the oxidizing agent and the mixture which includes the chiral ketone and the stereoisomer of the compound can be used with or without a solvent, i.e., they can be used neat (i.e., without any solvent) or in a solution.

The oxidizing agent of the method of the present invention can be any oxidizing agent capable of producing dioxiranes from the corresponding chiral ketones. However, for economic reasons a relatively inexpensive oxidizing agent such as peracids, hydrogen peroxide, sodium hypochlorite, potassium peroxomonosulfate, sodium perborate and hypofluoride (HOF) are preferred. Non-organic oxidizing agents are particularly preferred as these oxidizing agents and their reaction products can be easily removed from the reaction mixture by a simple aqueous extraction. A particularly preferred oxidizing agent is potassium peroxomonosulfate. The amount of oxidizing agent used in the present invention depends on a variety of factors including the reactivity of the chiral ketone, the reactivity of the compound, and the decomposition rate of the oxidizing agent. Preferably the amount of an oxidizing agent used is at least about 3 equivalents of the amount of the chiral ketone, more preferably at least about 2 equivalents of the amount of the chiral ketone, and most preferably at least about 1 equivalents of the amount of the chiral ketone.

It should be appreciated that while relative amounts of the chiral ketone and/or the oxidizing agent can be used to control the amount of kinetic resolution of a particular enantiomer in the racemic mixture, other conditions such as reaction temperature, reaction time, particular solvent(s) used in the reaction, structure of the chiral ketone, concentrations of each components, pH of the reaction, and a variety of other variables can be used to control the amount of kinetic resolution.

In asymmetric epoxidation of olefins, the reaction time affects both the yield of the epoxide as well as the enantiomeric excess of the epoxide produced. Thus, while a longer reaction period provides higher yield of the epoxide, the enantiomeric excess begins to decrease after awhile. Therefore, obtaining a maximum yield of the epoxide while maintaining a sufficient level of enantiomeric excess requires a compromise between the two diametrically opposed results.

Since the reaction time affects the extent of epoxidation and the enantiomeric excess of the epoxide product, kinetic resolution of the compounds is also affected by the reaction time. Preferably, for kinetic resolution of a stereoisomer mixture of compounds, the reaction time is from about 1 h to about 10 h, more preferably from about 1.5 h to about 5 h, and most preferably from about 1.5 h to about 2.5 h.

Figure 2:
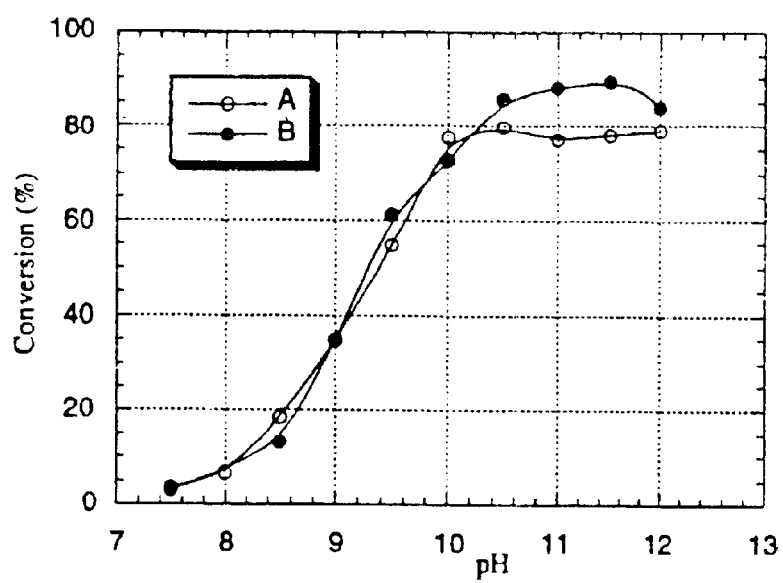
FIG. 2 is a plot of % conversion of trans-β-methylstyrene against pH of the epoxidation reaction using fructose-derived chiral ketone 1 in different solvent systems.

The pH can also affect the rate and the relative amount of kinetic resolution. In some cases, generally higher pH results in more rapid autodecomposition of the dioxirane and/or the oxidizing agent, which leads to the decrease in epoxidation efficiency. For this reason, most non-asymmetric epoxidations are usually carried out between pH 7 and pH 8. In some cases, the optimal pH is within a narrow window of 7.8–8.0. As shown in FIG. 1, some epoxidations are more effective at a higher pH. Lines A, B, C and D in FIG. 2 represent samples taken at a reaction time of 0.5 h, 1.0 h, 1.5 h and 2.0 h, respectively. In all cases, the optimal pH is about 12 for epoxidation of methylstyrene with acetone as a catalyst.

For the kinetic resolution of the present invention, another issue that needs to be considered is side reactions. As used in this invention, a "side reaction" is a reaction that does not ultimately lead to a production of a desired product (a desired product of the reaction between an oxidizing agent and a ketone is a dioxirane, whereas the desired product of the reaction between a dioxirane and an olefin is an epoxide). Without being bound by any theory, it appears that the Baeyer-Villiger reaction is one of the major side reactions for the catalyst at pH 7–8. The competing Baeyer-Villiger reaction can be reduced at a higher pH which can lead to a more efficient formation of dioxirane.

Figure 3:
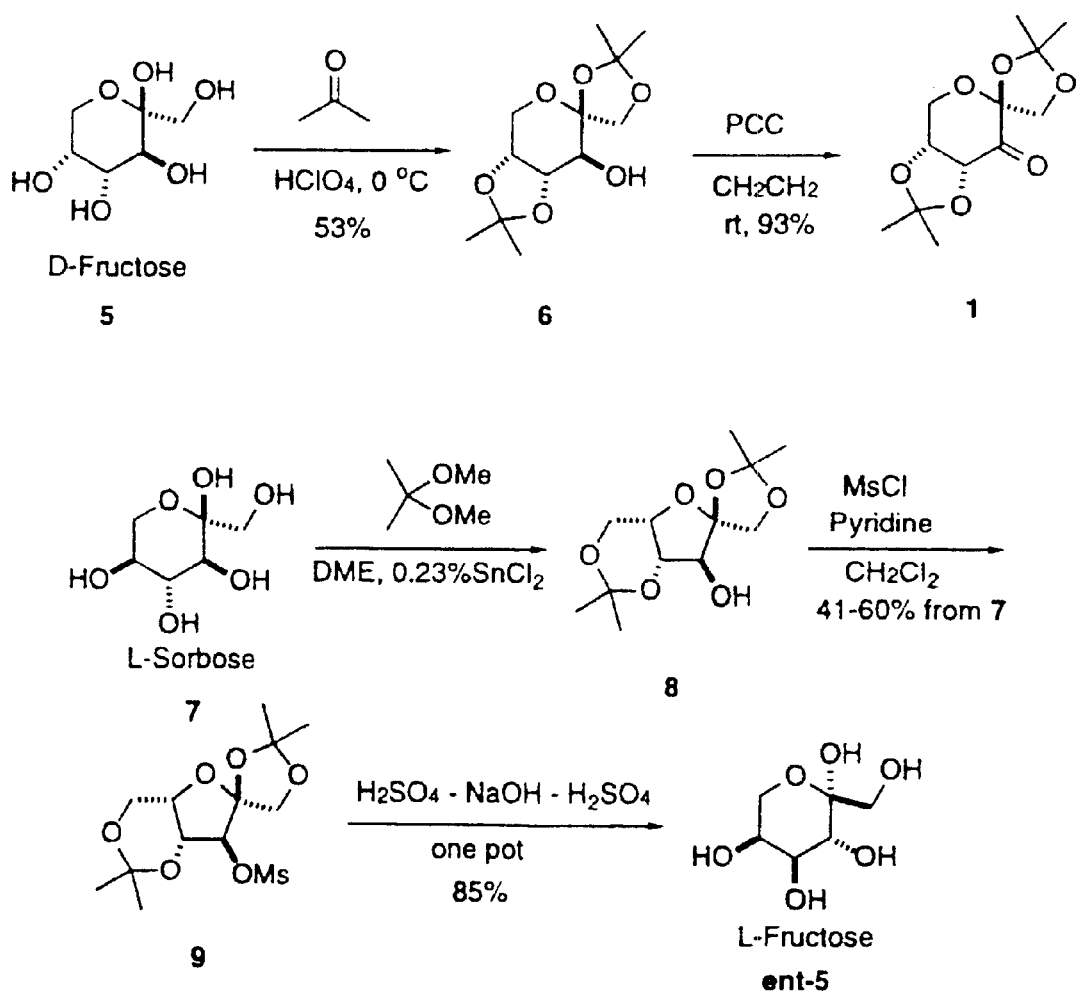
FIG. 3 illustrates a synthetic scheme for a preparation of a chiral ketone derived from D-fructose which is useful for kinetic resolution of a stereoisomer mixture of olefins as described in the present invention and a synthetic scheme for a preparation of L-fructose from L-sorbose.
Figure 5:
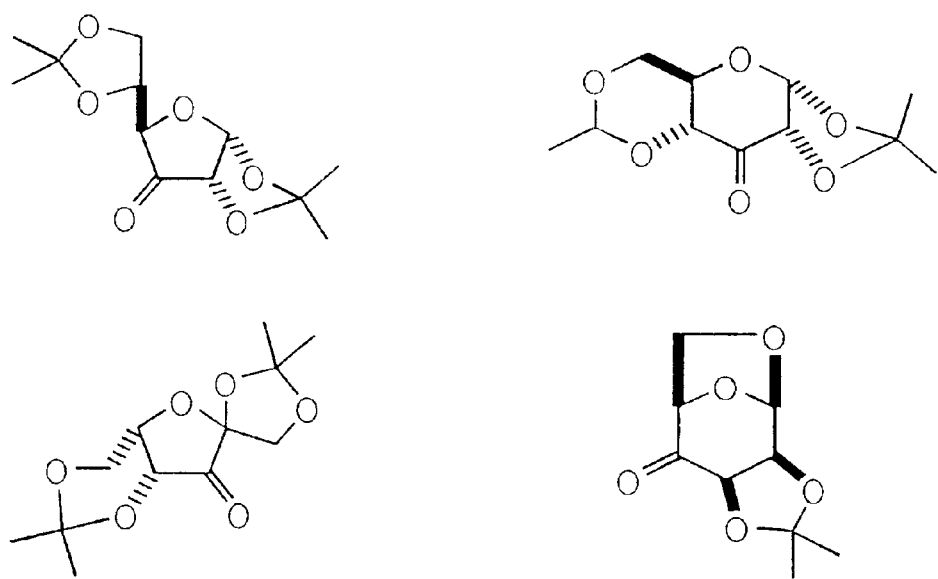
FIG. 5 shows a variety of chiral ketones prepared from glucose, sorbose and mannose which are useful in kinetic resolution of olefins as described in the present invention.
Figure 6:
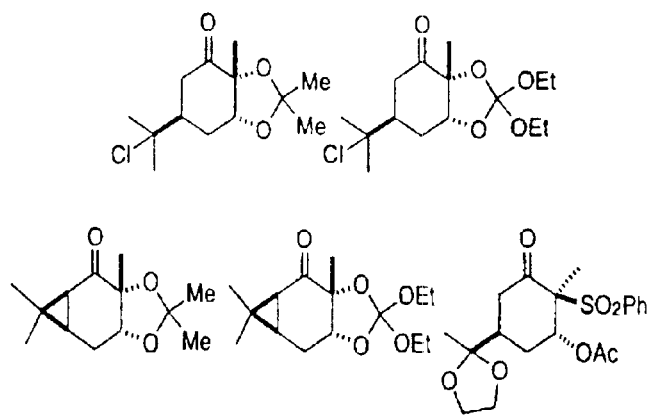
FIG. 6 shows a variety of chiral ketones prepared from carvone which are useful in kinetic resolution of olefins as described in the present invention.
Figure 7:
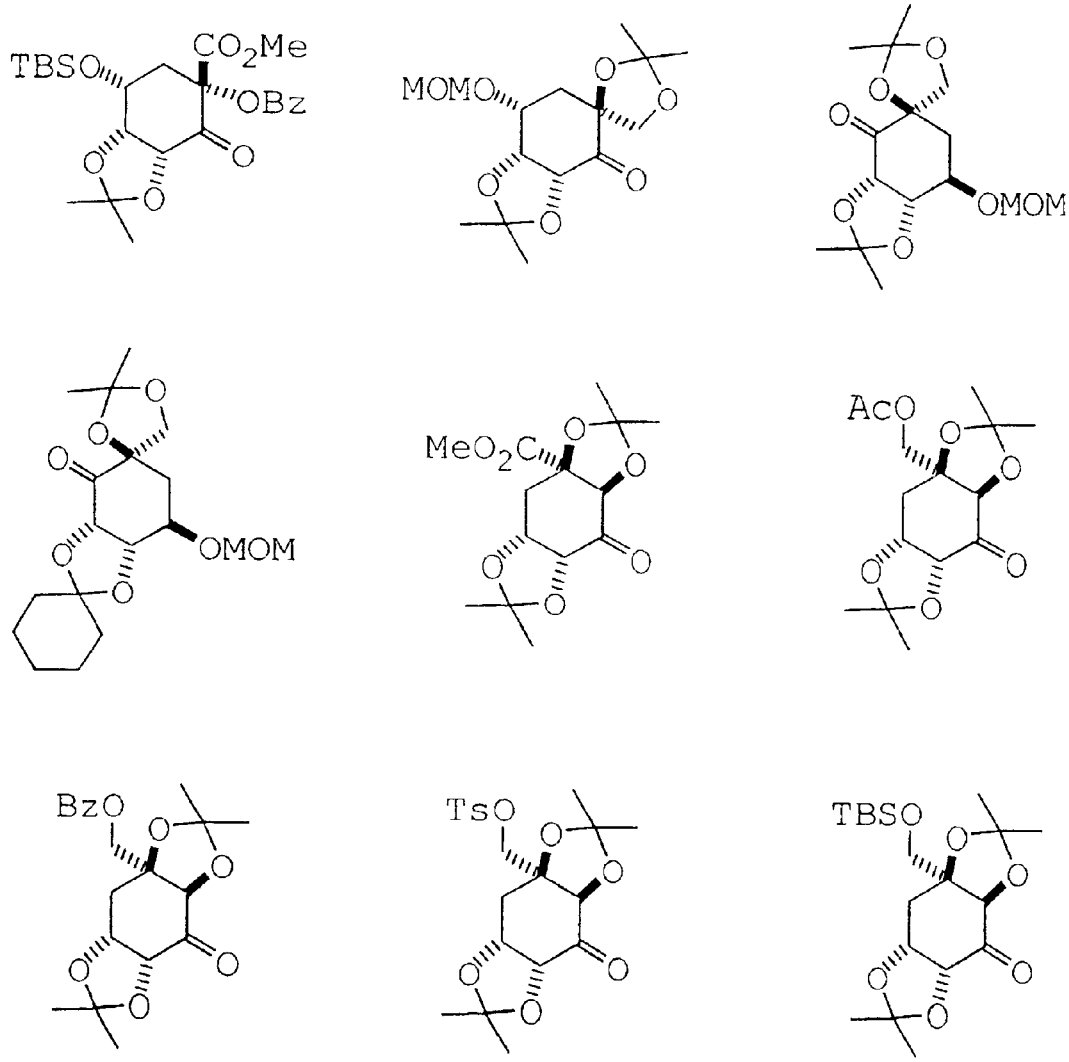
FIG. 7 shows a variety of chiral ketones prepared from quinic acid which are useful in kinetic resolution of olefins as described in the present invention.

A higher pH generally provides a higher conversion rate of the olefin to the epoxide and higher catalytic efficiency (i.e., higher turn-over rate). As shown in FIG. 3, the pH has a significant effect on the rate and the amount of epoxide produced. In FIG. 2, line A represents a reaction solvent system comprising 1:1.5 (v/v) of H$_2$O—CH$_3$CN and line B represents a reaction solvent system comprising 2:1:2 (v/v/v) of H$_2$O—CH$_3$CN-DMM. In certain cases, the production of epoxides from olefins increased more than 10 fold from a lower pH (7–8) to a higher pH (>10). In addition, the amount of oxidizing agent can be reduced significantly. The optimal pH range is broad. Preferably, the pH is at least about 5, more preferably at least about 8, still more preferably the pH is at least about 10. Even more preferably the pH of the reaction mixture is from about pH 5 to about pH 14, yet even more preferably from about pH 10 to about pH 14, and most preferably from about pH 10 to about pH 12.

The pH of the reaction can be conveniently achieved by adding a sufficient amount of base to maintain the pH at a desired level. The base can be added separately, it can be added to the solution containing the chiral ketone, or it can be added to the solution containing the oxidizing agent. Alternatively, a solid mixture of the base and oxidizing agent can be added to the reaction mixture. Preferably the base is selected from the group consisting of hydroxides, carbonates, bicarbonates, borates and phosphates. More preferably the base is selected from the group consisting of potassium carbonate, potassium bicarbonate, lithium carbonate, lithium bicarbonate, sodium carbonate, sodium bicarbonate, calcium carbonate, sodium borate, sodium phosphate, potassium phosphate, lithium hydroxide, sodium hydroxide, potassium hydroxide, magnesium hydroxide and calcium hydroxide, most preferably the base is selected from the group consisting of potassium carbonate, potassium bicarbonate, sodium bicarbonate, sodium carbonate, sodium hydroxide, sodium borate, sodium phosphate, potassium phosphate, tetraalkylammonium hydroxide and potassium hydroxide. Alternatively, the desired pH of the reaction can be more easily maintained by using a buffer solution.

The solvent system, when used, also affects the rate of epoxidation, which may also affect kinetic resolution. Typically, any organic solvent can be used for the present invention. Exemplary solvents include, nitrites such as acetonitrile and propionitrile, dimethoxymethane (DMM), dimethoxyethane (DME), ethers such as-tetrahydrofuran (THF) and diethyl ether ($Et_2O$), dichloromethane, chloroform, ethyl acetate, hexane, benzene, toluene, xylenes, dioxane, dimethyl formamide (DMF), pentane, alcohols including, but not limited to, methanol, ethanol and i-propyl alcohol, and mixtures thereof.

A mixture of organic solvent and an aqueous solution can also be used as a reaction solution. As Table 1 shows, a wide variety of solvents can be used for the epoxidiation of compounds. The percentage of enantiomeric excess (% ee), which is a measure of enantioselectivity, is equal to the percent of one enantiomer (e.g. stereoisomer) minus the percent of the other enantiomer. Thus for example, if the reaction produces (R,R) and (S,S) epoxides in 99% and 1%, respectively, the enantiomeric excess percentage (% ee) will be 98%. Kinetic resolution is also similary affected by the solvent system.

TABLE 1

The Solvent Effects on the Asymmetric Epoxidation

| Entry | Solvents | T (° C.) | Time (min) | Conversion (%)[b] | % ee[c] |
|---|---|---|---|---|---|
| 1 | $CH_3CN$ | 20 | 20 | 100 | 89 |
| 2 | $CH_3CN$ | 0 | 90 | 96 | 92 |
| 3 | $CH_3CH_2CN$ | 20 | 60 | 11 | 80 |
| 4 | DMM | 20 | 60 | 36.2 | 91 |
| 5 | DME | 20 | 20 | 100 | 89 |
| 6 | DME | 0 | 90 | 92 | 89 |
| 7 | DMF | 20 | 20 | 95 | 86 |
| 8 | Dioxane | 20 | 20 | 100 | 86 |
| 9 | Dioxane | 0 | 90 | 96 | 86 |
| 10 | THF | 20 | 60 | 18 | 74 |
| 11 | $Et_2O$ | 20 | 60 | 0 | |
| 12 | $CH_2Cl_2$ | 20 | 30 | <3 | nd |
| 13 | $CH_3CN$/DMM (2/1) | 20 | 20 | 100 | 90 |
| 14 | $CH_3CN$/DMM (2/1) | 0 | 90 | 100 | 92 |
| 15 | $CH_3CN$/DMM (1/1) | 20 | 20 | 98 | 91 |
| 16 | $CH_3CN$/DMM (1/1) | 0 | 90 | 100 | 93 |
| 17 | $CH_3CN$/DMM (½) | 20 | 20 | 94 | 92 |
| 18 | $CH_3CN$/DMM (½) | 0 | 90 | 88 | 94 |
| 19 | $CH_3CN$/DMM (1/4) | 0 | 90 | 77 | 94 |
| 20 | DMM/DME (1/1) | 20 | 25 | 66 | 92 |

TABLE 1-continued

The Solvent Effects on the Asymmetric Epoxidation

| Entry | Solvents | T (° C.) | Time (min) | Conversion (%)[b] | % ee[c] |
|---|---|---|---|---|---|
| 21 | $CH_3CN$/DMM/DME (1/1/2) | 20 | 20 | 100 | 90 |
| 22 | $CH_3CN$/DMM/DME | 20 | 20 | 89 | 90 |
| 23 | $CH_3CN$/THF (1/1) | 20 | 25 | 63 | 82 |
| 24 | $CH_3CN$/$Et_2O$ (1/1) | 20 | 25 | 28 | 84 |
| 25 | $CH_3CN$ | 0 | 240 | 58.4 | 63.4 |
| 26 | DME | 0 | 240 | 100 | 69.6 |
| 27 | DME | −10 | 240 | 95 | 73.1 |
| 28 | DMM | 0 | 240 | 43 | 66.3 |
| 29 | Dioxane | 0 | 240 | 99.4 | 66.6 |
| 30 | DMM/$CH_3CN$ (2/1) | 0 | 240 | 91 | 67.1 |
| 31 | DMF | 0 | 180 | 99 | 64.3 |

[a]Reactions in entries 1–24 were carried out with trans-β-methylstyrene (1 mmol), ketone 1 (0.3 mmol), Oxone ® (1.38 mmol) in a mixture of 15 mL of organic solvent and 10 mL of 0.05 M $Na_2B_4O_7 \cdot 10H_2O$ in aqueous EDTA (4 × $10^{-4}$ M) solution, and the pH was adjusted to 10.5 by using 1.0 M aqueous $K_2CO_3$ solution. Reactions in entries 25–31 were carried out with trans-β-methylstyrene (0.4 mmol), ketone DW-25a (see Experimental section) (0.02 mmol), Oxone ® (0.55 mmol), and $K_2CO_3$ (2.31 mmol) in organic solvent (6 mL) and buffer (0.05 M $Na_2B_4O_7 \cdot 10H_2O$ in aqueous EDTA (4 × $10^{-4}$ M) (4 mL).
[b]Conversion was determined by GC (HP-17 column).
[c]Enantioselectivity was determined by chiral GC (Chiraldex γ-TA column).

Preferably the solvent is selected from the group consisting of acetonitrile, DMM, DME, DMF, dioxane and mixtures thereof. In certain cases, a mixture of solvents provide higher kinetic resolution.

The temperature of the reaction can also affect kinetic resolution of compounds. Similar to higher enantiomeric excess of epoxidation at lower temperature, as shown in Table 2, a lower reaction temperature results in higher kinetic resolution.

TABLE 2

The Temperature Effect on the Epoxidation of trans-β-Methylstyrene by Ketone 1[a]

| Entry | T (° C.) | Conv. (%)[b] | ee (%)[c] |
|---|---|---|---|
| 1 | −11 | 99.4 | 95.7 |
| 2 | −6 | 96.9 | 95.4 |
| 3 | −2 | 97.5 | 95.2 |
| 4 | 2 | 99.4 | 94.7 |
| 5 | 8 | 99.0 | 93.8 |
| 6 | 20 | 99.0 | 93.2 |
| 7 | 30 | 96.8 | 91.1 |

[a]All reactions were carried out with trans-β-methylstyrene (1 mmol), ketone 1 (1 mmol), Oxone ® (1 mmol), $K_2CO_3$ (4.3 mmol), and $Bu_4NHSO_4$ (0.05 mmol) in 25 mL of $CH_3CN$-DMM-0.05 M $Na_2B_4O_7 \cdot 10H_2O$ in aqueous EDTA (4 × $10^{-4}$ M) solution (1:2:2, V/V); the reactions were stopped after 20 min.
[b]Conversion was determined by GC (HP-17 column).
[c]Enantioselectivity was determined by chiral GC (Chiraldex γ-TA column).

Preferably, kinetic resolution of a racemic mixture of the compound is carried out at a reaction temperature of less than about 50° C., more preferably less than about 30° C., and most preferably less than about 0° C.

The method of the present invention can also be used in kinetic resolution of racemic compounds containing conjugated polyenes. A "polyene" is a compound which has more than one unsaturated bonds including dienes, trienes and enynes.

Preferably, the method of the present invention provides enantiomeric enrichment of the compound of at least about 50% ee, more preferably at least about 80% ee, and most preferably at least about 90% ee.

One of the advantages of the present invention is the availability of relatively inexpensive starting materials for producing chiral ketones. Some of the chiral ketones which can be easily prepared from readily available starting materials and their representative epoxidation of olefins are shown in FIGS. 3–7. For example, chiral ketones can be easily synthesized in high overall yields from readily available carbohydrates such as fructose, sorbose, glucose and mannose. See FIGS. 3, 4 and 5. In addition, chiral ketones of the present invention can also be synthesized from other inexpensive and readily available compounds such as carvone (see FIG. 6), inositol, and quinic acid (see FIG. 7).

Kinetic resolution of the racemic compounds can be performed in a variety of different sequences. The addition sequence of the racemic compound, the chiral ketone, base and the oxidizing agent can be interchanged depending on the nature of each components. Typically, however, an aqueous solution comprising the oxidizing agent and a separate base solution or a solid oxidizing agent and a solid base are added to a mixture comprising the chiral ketone and the racemic compound. A reverse-addition technique can also be used depending upon the reactivity of each components. A reverse-addition is where the mixture comprising the chiral ketone is added to the solution comprising the oxidizing agent or to a solid oxidizing agent.

The rate of addition of the oxidizing agent to the mixture comprising the chiral ketone and the racemic mixture of the compound will vary depending upon a various factors such as the size of the reaction and the substrates.

Kinetic resolution methods of the present invention are environmentally friendly. Water is typically used as a cosolvent and no toxic metals are used. Therefore, no special disposal method is required, which significantly reduces the overall cost of the present invention.

Additional objects, advantages, and novel features of this invention will become apparent to those skilled in the art upon examination of the following examples thereof, which are not intended to be limiting.

EXAMPLES

General Methods:

Oxone® (potassium peroxymonosulfate) was purchased from Aldrich (Milwaukee, Wis.). It has been found that the oxidation activity of the purchased Oxone® occasionally varies with different batches. All glassware used for the epoxidation was carefully washed to be free of any trace metals which catalyze the decomposition of Oxone. The 300 MHZ $^1$H NMR and 75.5 MHZ $^{13}$C NMR spectra were measured on a Bruker ACE-300 spectrometer in CDCl$_3$. Proton chemical shifts ($\delta$) are given relative to internal TMS (0.00 ppm), and Carbon chemical shifts are given relative to CDCl$_3$, (77.23 ppm). Infrared spectra were recorded on a Perkin-Elmer 1600 Series FTIR spectrometer. High-resolution mass spectra were performed by the mass spectrometry facility of Colorado State University. Elemental analyses were performed by M-H-W Laboratories, Phoenix, Ariz. Optical rotations were measured on an Autopol® III automatic polarimeter in a 1 cm cell. Silica gel 60 of E-Merck Co. was employed for all flash chromatography.

As shown in FIG. 3, ketone 1 is readily prepared from readily available inexpensive D-Fructose by ketalization and oxidation. See Mio et al. *Tetrahedron* 1991, 47, 2133–2144. The enantiomer of ketone catalyst 1 (ketone ent-1) is prepared in the same way from L-fructose (ent-5), which can be prepared from readily available L-sorbose by ketalization, mesylation, and one pot acid-base treatment based on the reported procedure. See Chen et al., *Carbohydr. Res.* 1988, 175, 265–271.

1,2:4,5-Di-O-isopropylidene-D-erythro-2,3-hexodiuro-2,6-pyranose (1)

Perchloric acid (70%) (8.6 mL) was added to a suspension of D-fructose (36.84 g, 204.7 mmol) in acetone (740 mL) and 2,2-dimethoxypropane (14.8 mL, 120 mmol) at 0° C. (ice bath). After the reaction mixture was stirred under nitrogen at 0° C. for 6 h, concentrate ammonium hydroxide was added to pH=7–8. After the resulting mixture was stirred for another 5 min, the solvent was removed under reduced pressure, and the solid residue was recrystallized from hexane/CH$_2$Cl$_2$ (4/1, v/v) to afford white needles (alcohol 6) (28.34 g, 53.2%).

PCC (11.64 g, 54 mmol) was added portionwise over 15 min to a mixture of alcohol 6 (5.2 g, 20 mmol) and powdered 3A molecular sieves (22 g, activated at 180–200° C. under vacuum) in CH$_2$Cl$_2$ (100 mL). After the reaction mixture was stirred for 3 h under nitrogen, it was filtered through celite and washed carefully with ether. The filtrate was concentrated and the residue was purified by passing through a short silica gel column (hexane:ether=1:1, v/v) to afford a white solid (4.80 g, 93.0%), which was recrystallized from hexane/CH$_2$Cl$_2$ to give white crystals (ketone 1). MP 101.5–103° C. $[\alpha]^{25}_D$=−125.4° (c 1.0, CHCl$_3$). IR (KBr): 1749 cm$^{-1}$. $^1$H NMR $\delta$ 4.73 (d, J=5.7 Hz, 1H), 4.61 (d, J=9.5 Hz, 1H), 4.55 (ddd, J=5.7, 2.2, 1.0 Hz, 1H), 4.39 (dd, J=13.4, 2.2 Hz, 1H ), 4.12 (d, J=13.4 Hz, 1H), 4.00 (d, J=9.5 Hz, 1H), 1.55 (s, 3H), 1.46 (s, 3H), 1.40 (s, 6H). $^{13}$C NMR $\delta$ 197.1, 114.0, 110.8, 104.3, 78.11, 76.07, 70.20, 60.28, 27.33, 26.70, 26.24, 26.20. Anal. Calcd for C$_{13}$H$_{20}$O$_5$: C, 55.81; H, 7.02. Found: C, 55.47; H, 7.10.

1,2:4,5-Di-O-isopropylidene-L-erythro-2,3-hexodiuro-2,6-pyranose (ent-1)

A solution of SnCl$_2$ (0.0125 g, 0.066 mmol) in 0.5 mL of 1,2-dimethoxyethane was added to a suspension of L-sorbose (5 g, 27.75 mmol) in 2,2-dimethoxypropane (15 mL). The mixture was refluxed gently with stirring until it was clear, then evaporated to a syrup (alcohol 8).

The syrup was dissolved in CH$_2$Cl$_2$ (15 mL), followed by the addition of pyridine (3.5 mL, 43.3 mmol) and DMAP (catalytic amount). The solution was then cooled in an ice bath, and methanesulfonyl chloride (3.3 mL, 42.6 mmol) was added dropwise. After the reaction mixture was stirred for 2 h at 0° C., water was added. The mixture was extracted with CH$_2$Cl$_2$. The combined organic layers were washed with brine, dried (Na$_2$SO$_4$), filtered, and concentrated to give crude mesylate 9. Recrystallization from ethanol gave colorless needles (3.63 g, 41% yield for two steps). [In a separate run the crude mesylate was flash chromatographed (hexane:EtOAc=3:1, v/v) to give 9 as a pale yellow solid (5.3 g, 60%)].

To a solution of mesylate 9 (29.5 g, 87.3 mmol) in acetone (236 mL), was added an aqueous solution of 0.25% H$_2$SO$_4$ (177 mL). After being stirred at 25° C. for 20 h, the solution was made alkaline with 9 M NaOH (23.6 mL). The resulting mixture was heated at 70–80° C. for 48 h, acidified to pH of about 1 with 9 M H$_2$SO$_4$, and heated at 70–80° C. for 20 min. After being neutralized with 2 M NaOH, the mixture was taken to dryness and the residue was extracted with ethanol (500 mL). The ethanol solution was concentrated to a syrup (L-fructose) (14 g, 85%).

The resulting crude L-fructose was directly converted to ketone ent-1 using the same procedure as D-fructose. The resulting ketone ent-1 [mp 102–103° C. $[\alpha]^{25}_D$=+123° (c 0.58, CHCl$_3$)] showed the same enantioselectivity as ketone 1.

Procedure for pH Study:

To a 100 mL three-neck round bottom flask were added buffer (10 mL) [$4\times10^{-4}$ M aq. $Na_2EDTA$ adjusting with 1.0 M KOH for pH 7.5–8.0; 0.05 M $Na_2B_4O_7 \cdot 10H_2O$ in $4\times10^{-4}$ M aq. $Na_2EDTA$ adjusting with 1.0 M aq. $KH_2PO_4$ for pH 8.5–10.5; 0.05 M aq $K_2HPO_4$ plus 0.1 M aq. NaOH (2:1, v/v) adjusting with 1.0 M $KH_2PO_4$ for pH 11.0–12.0; 0.05 M aq $K_2HPO_4$ plus 0.1 M aq. NaOH (2:1, v/v) adjusting with 1.0 M KOH for pH 12.5–13.0], acetonitrile (15 mL), trans-β-methylstyrene (0.118 g, 1 mmol), tetrabutylammonium hydrogen sulfate (0.015 g, 0.04 mmol), and ketone 1 (0.0516 g, 0.2 mmol). The reaction mixture was cooled by an ice bath. A solution of Oxone® (1.54 g, 2.5 mmol) in aq. $Na_2EDTA$ ($4\times10^{-4}$ M, 10 mL) was added through a syringe pump at a speed of 4.1 mL/h. The reaction pH was monitored by a Corning 320 pH meter with a Corning "3 in 1" pH combination electrode and was maintained within ±0.1 by adding 0.5 N aq. KOH. The conversion and ee values were checked by GC every 30 min.

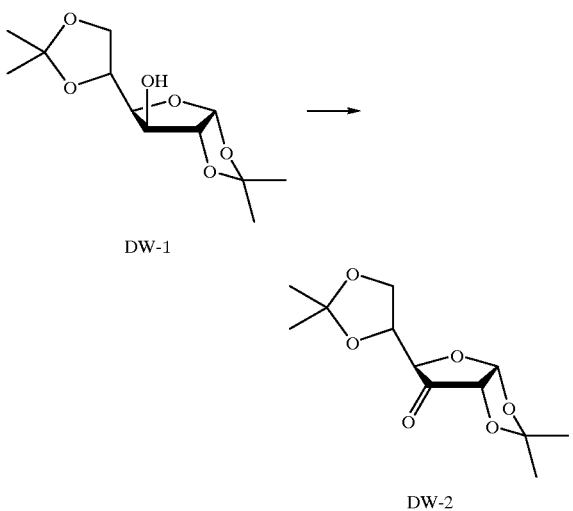

Preparation of Ketone DW-2.

To a solution of alcohol DW-1 (8 g, 30.8 mmol) in dry $CH_2Cl_2$ (90 mL) and acetic anhydride (10 mL) were added PDC (12 g, 32 mmol) and freshly activated 3A molecular sieve powder (16 g). After refluxing for 6 hours, the reaction mixture was diluted with ethyl acetate (100 mL), filtered through a glass funnel with celite, concentrated, and purified by flash chromatography (hexane:ether, 1:1, v/v) to give ketone DW-2 as a colorless syrup (7.3 g, 90%). $[a]_D^{25}$=+102.1° (c 2.2, $CHCl_3$). IR (KBr): 1773 $cm^{-1}$. $^1$H NMR: δ 6.13 (dd, J=4.5, 1.8 Hz, 1H), 4.4–4.31 (m, 3H), 4.05–4.0 (m, 2H), 1.45, 1.42 (s, each 3H), 1.33 (s, 6H). $^{13}$C NMR: δ209, 114.5, 110.5, 103.3, 79.12, 77.43, 76.56, 64.48, 27.73, 27.34, 26.15, 25.47.

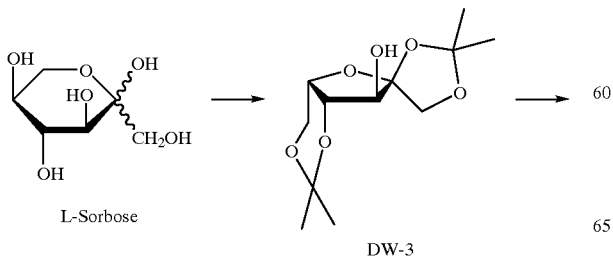

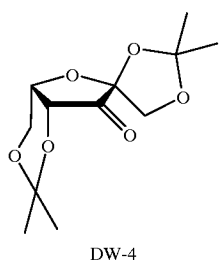

Preparation of Ketone DW-4.

1,2:4,6-Di-O-isopropylidene-a-L-sorbofuranose (DW-3) was prepared based on a known procedure see: C—C. Chen et al, *Carbohydrate Research*, 1988, 175, 265–271.

To a solution of alcohol DW-3 (1.3 g, 5 mmol) in dry $CH_2Cl_2$ (10 mL) were added 3A molecular sieve powder (1.7 g) and PCC (2.2 g, 10 mmol). After being stirred at room temperature for 30 min, the reaction mixture was diluted with ether (50 mL), filtered through a glass funnel with a thin silica-gel layer, and washed with ether. The filtrate was concentrated and purified by flash chromatography (hexane:ethyl acetate, 2:1, v/v) to give a syrup (1 g) which was recrystallized from hexane to yield white crystals (0.8 g, 57%). MP 82–84° C. $[a]_D^{25}$=−48.4° (c 0.71, $CHCl_3$). IR and NMR data showed DW-4 existed in hydrate form. IR (KBr): 3385, 1785 $cm^{-1}$. $^1$H NMR: δ 4.42 (d, J=9.6 Hz, 1), 4.35 (bs, 1H, OH), 4.13–3.90 (m, 5H), 3.61 (bs, 1H, OH), 1.54, 1.47, 1.44, 1.42 (s, each 3H). $^{13}$C NMR: δ 111.2, 111.2, 100.3, 98.24, 72.86, 71.16, 70.33, 60.91, 28.91, 26.5, 25.65, 19.52.

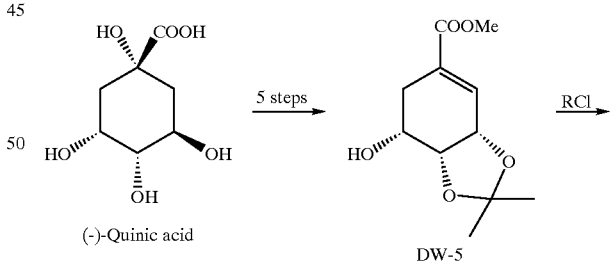

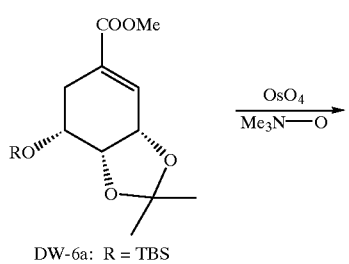

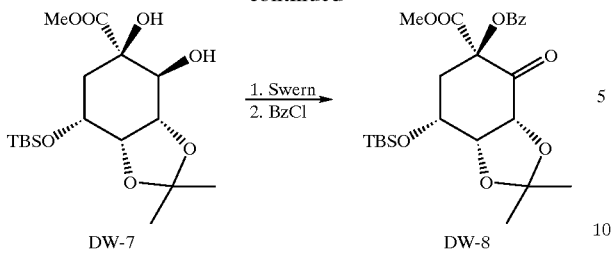
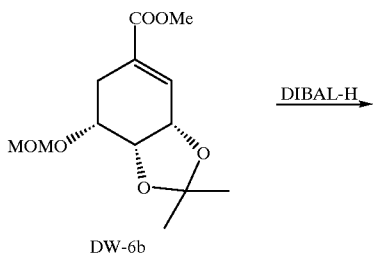

Preparation of DW-8

DW-5 was prepared based on a known procedure from (−)-Quinic acid with 5 steps. See T. K. M. Shing et al, *Tetrahedron*, 1991, 47, 4571–4578. $^1$H NMR showed DW-5 was obtained a mixture of 2,3-O-isopropylidene and 1,2-O-isopropylidene with a ratio of 91.5:8.5.

To a solution of DW-5 (1.1 g, 4.8 mmol), imidazole (0.65 g, 9.6 mmol), and a catalytic amount of DMAP in dry $CH_2Cl_2$ (20 mL) was added TBSCl (0.9 g, 6.0 mmol) at room temperature. After being stirred for 10 hours, the reaction mixture was quenched with aqueous $NH_4Cl$ and extracted with $CH_2Cl_2$ (3×20 mL) The combined extracts were washed with water and brine, dried over $Na_2SO_4$, concentrated and purified by flash chromatography (hexane:ether, 10:1 to 5:1) to afford 2,3-O-isopropylidene (DW-6a, 1.2 g) and 1,2-O-isopropylidene (0.16 g).

To a solution of DW-6a (1.0 g, 2.9 mmol), trimethylamine N-oxide dihydrate (0.6 g, 5.4 mmol), pyridine (1.8 mL), and water (0.3 mL) in t-BuOH (8 mL) was added $OsO_4$ (0.01 g, 0.039 mmol) under $N_2$. After refluxing for 10 hours, the reaction mixture was cooled, then quenched with saturated aqueous $Na_2SO_3$ (5 mL). The mixture was then passed through a short silica-gel column and eluted with ethyl acetate. The eluent was concentrated and redissolved in $CH_2Cl_2$. The resulting solution was washed with saturated aqueous $Na_2SO_3$ and water, dried over $Na_2SO_4$, and concentrated to afford DW-7 as white crystals.

To a stirred solution of DMSO (0.120 g, 1.6 mmol) in dry $CH_2Cl_2$ (0.5 mL) at −78° C. under nitrogen was added dropwise oxalyl chloride (0.072 mL, 0.75 mmol). The mixture was stirred for 10 min, then removed from the cold bath for 3 min, and recooled to −78° C. Alcohol DW-7 (0.19 g, 0.5 mmol) in dry $CH_2Cl_2$ (1.5 mL) was added in one portion and the mixture was stirred for 10 min. Triethylamine (0.34 mL, 2.5 mmol) was added, the mixture was stirred for 10 min and then slowly warmed to room temperature. The reaction mixture was quenched with saturated aqueous $NH_4Cl$, extracted with $CH_2Cl_2$, dried ($Na_2SO_4$), concentrated, and purified with flash chromatography (hexane:ethyl acetate, 5:1 to 2:1) to give the hydroxyl-ketone (0.115 g, 60%).

To a solution of the above hydroxyl-ketone (0.09 g, 0.24 mmol) in pyridine (1 mL) was added DMAP (0.005 g) and BzCl (0.2 mL). After being stirred at room temperature for 2 hours, the reaction mixture was quenched with saturated aqueous $NH_4Cl$, extracted with ether (4×10 mL), washed with water, brine, dried over $Na_2SO_4$, concentrated, and purified by flash chromatography (hexane:ethyl acetate, 8:1) to afford ketone DW-8 as a colorless syrup (0.096 g, 87%). IR (KBr): 1764, 1750 cm$^{-1}$. $^1$H NMR: δ 8.02 (m, 2H), 7.65 (m, 1H), 7.50 (m, 2H), 4.85 (d, J=6.0 Hz, 1H), 4.54 (ddd, J=6.0, 3.0, 1.5 Hz, 1H), 4.4 (ddd, J=10.2, 3.9, 3.0 Hz, 1H), 3.82 (s, 3H), 3.01 (dd, J=15.0, 10.2 Hz, 1H), 2.69 (ddd, J=15.0, 3.9, 1.5 Hz, 1H), 1.55 (s, each 3H), 1.4 (s, each 3H), 0.88 (s, 9H), 0.095, 0.072 (s, each 3H).

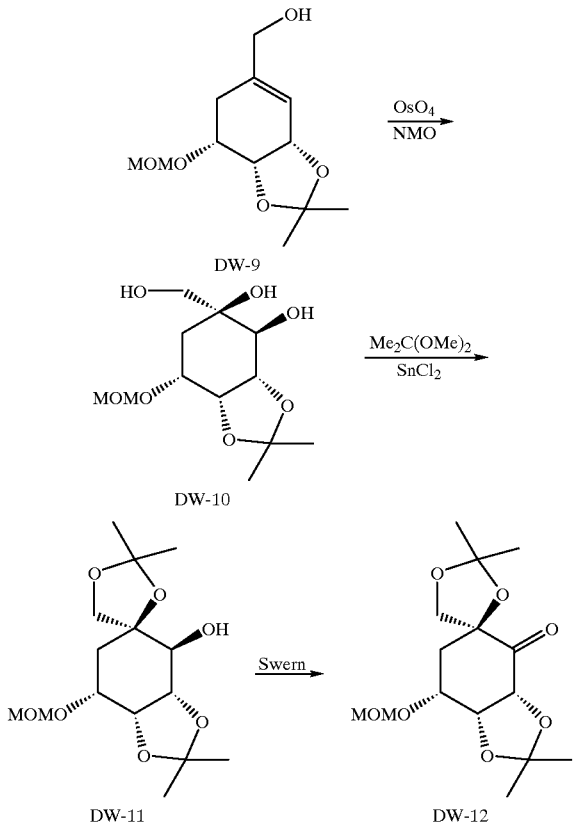

Preparation of DW-12.

To solution of alcohol DW-5 (10.3 g, 45.3 mmol) in dry $CH_2Cl_2$ (55 mL) were added i-$Pr_2NEt$ (12 mL), MOMCl (5.6 mL), and a catalytic amount of DMAP at 0 (C. After being stirred at room temperature overnight, the reaction mixture was quenched with saturated aqueous $NH_4Cl$, extracted with $CH_2Cl_2$, washed with water and brine, dried over $Na_2SO_4$, concentrated, and purified by flash chromatography (hexane:ethyl acetate, 4:1) to give DW-6b (10.4 g, 90%).

To a solution of DW-6b (8.8 g, 32 mmol) in dry THF (10 mL) was added dropwise a solution of DIBAL-H (1.0 M in hexane, 70 mL) over 20 min at −15° C. The mixture was stirred at 0° C. for 1 h, quenched with the saturated aqueous $NH_4Cl$, filtered, washed with ether, and concentrated to give DW-9 as a colorless syrup (7.9 g, 99%).

To a solution of DW-9 (7.8 g, 31 mmol), NMO (6.0 g, 51 mmol), pyridine (15 mL, 192 mmol), water (3 mL, 160 mmol) in t-BuOH (60 mL) was added $OsO_4$ (0.06 g) under nitrogen with stirring. After refluxing for 5 hours, the reaction mixture was cooled, quenched with saturated aqueous $Na_2S_2O_5$ (20 mL), and concentrated. The resulting residue was filtered through a short silica-gel filter and washed with ethyl acetate and $CH_2Cl_2$-EtOH (2:1). The filtrate was concentrated and the residue was recrystallized from hexane-CH$_2$Cl$_2$ to give DW-10 white crystals (6.8 g, 77%).

To a suspension of DW-10 (1.38 g, 5 mmol) in 2,2-dimethoxypropane (20 mL) was added catalytic amount of CSA at 0° C. with stirring. After being stirred at 0° C. for 2 hours, the reaction mixture was slowly warmed to room temperature, and stirred at this temperature for another 2 hours. The reaction was quenched with triethylamine (0.2 mL), and diluted with water and ether. The aqueous solution was extracted with ether. The combined extracts were washed with water and brine, dried over Na$_2$SO$_4$, and concentrated to give a syrup which was used for next step without further purification.

To a solution of DMSO (0.69 g, 8.9 mmol) in dry CH$_2$Cl$_2$ (2 mL) was added dropwise oxalyl chloride (0.43 mL, 4.45 mmol) at −78° C. The solution was stirred at −78° C. for 10 min, then removed from cold bath for 3 min, and recooled to −78° C. A solution of the above crude alcohol in dry CH$_2$Cl$_2$ (5 mL) was added. After the solution was stirred at −78° C. for 1 hour, triethylamine (1.86 mL, 13.5 mmol) was added dropwise, and the resulting mixture was stirred at −78° C. for 10 min, then warmed to room temperature. After the addition of saturated aqueous NH$_4$Cl (20 mL), the mixture was extracted with ether, washed with water and brine, dried over Na$_2$SO$_4$, concentrated and purified by flash chromatography (hexane:ethyl acetate, 5:1 to 2:1) to give ketone DW-12 as a light yellow oil, which was recrystallized from hexane to give white crystals (0.66 g, 42% from DW-10). MP 52–53° C. $[a]_D^{25}$=−41.7° (c 0.64, CH$_2$Cl$_2$). IR (KBr): 1743 cm$^{-1}$. $^1$H NMR: δ 4.82 (d, J=5.1 Hz, 1H), 4.8 (d, J=6.9 Hz, 1H), 4.77 (d, J=6.9 Hz, 1H), 4.7 (dd, J=5.1, 3.3, 1.2 Hz, 1H), 4.67 (d, J=8.8 Hz, 1H), 4.5 (ddd, J 11.1, 5.4, 3.3 Hz, 1H), 3.61 (d, J=8.8 Hz, 1H), 3.43 (s, 3H), 2.25 (ddd, J=13.5, 5.4, 1.2 Hz, 1H), 2.17 (dd, J=13.5, 11.1 Hz, 1H), 1.48, 1.44, 1.43, 1.26 (s, each 3H). $^{13}$C NMR: δ 204.1, 111.4, 111.1, 96.54, 83.17, 78.57, 77.87, 69.99, 68.42, 55.9, 36.65, 27.18, 27.08, 26.17 (2C). Anal. Calcd for C$_{15}$H$_{24}$O$_7$: C, 56.95; H, 7.65. Found: C, 57.14; H, 7.69.

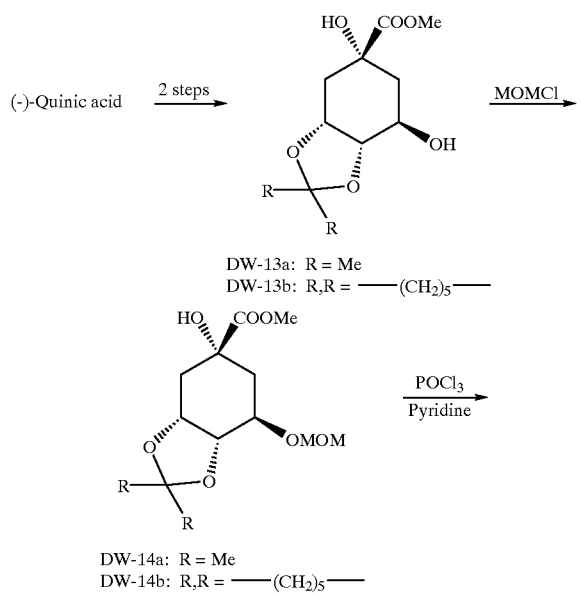

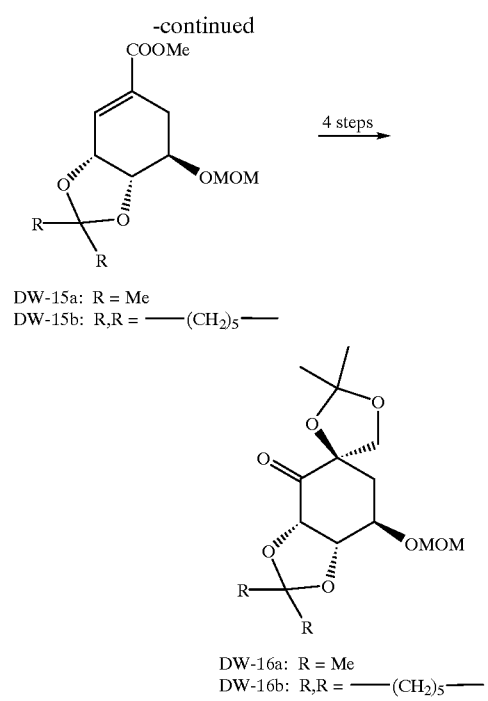

Preparation of DW-16a and DW-16b.

To a suspension of (−)-quinic acid (46 g, 0.239 mol) in 2,2-dimethoxypropane (60 mL) and benzene (180 mL) was added TsOH (0.1 g). After refluxing for 15 hours, the reaction mixture was cooled to room temperature and quenched with triethylamine (0.5 mL). The solvent was removed under reduced pressure, and the residue was treated with ethyl acetate (100 mL). After filtration, the filtrate was concentrated and recrystallized in hexane-ethyl acetate to yield a lactone as white needles (43 g, 83.8%).

To a solution of the above lactone (13.4 g, 63.5 mmol) in MeOH (75 mL) was added MeONa (4.4 g, 81.5 mmol). After being stirred at room temperature for 3 hours, AcOH (4.66 mL, 81.5 mmol) was added dropwise and the solvent was removed under reduce pressure. The resulting syrup was dissolved in ether (200 mL), filtered through a thin silica-gel, washed with ether and ethyl acetate,. concentrated, and purified by flash chromatography (hexane:ethyl acetate 3:1 to 1:2, v/v) to give alcohol DW-13a as a slightly yellow syrup (10.1 g, 82%) along with recovered lactone (2 g).

DW-13b was prepared based on a reported procedure. See T. K. M. Shing et al, *Tetrahedron*, 1990, 46, 6575–6584.

MOMCl (2.81 g, 35 mmol) was added dropwise to a solution of DW-13a (6.3 g, 25 mmol), i-Pr$_2$NEt (6.3 mL, 35 mmol), and catalytic amount of DMAP in CH$_2$Cl$_2$ (50 mL) at 0° C. After being stirred at 0° C. for 15 hours, the reaction mixture was quenched with saturated aqueous NH$_4$Cl, and extracted with CH$_2$Cl$_2$, washed with water and brine, dried (Na$_2$SO$_4$), and concentrated to give a yellow syrup which was used for next step without further purification. DW-14b was prepared similarly from DW-13b in 95% yield.

POCl$_3$ (2.5 mL) was added to a solution of crude DW-14a in pyridine (50 mL) at 0° C. with stirring. After being stirred at room temperature for 3 hours, the reaction mixture was diluted with ether, and quenched with saturated aqueous NH$_4$Cl at 0° C. The aqueous layer was extracted with ether (4×30 mL), washed with water (3×50 mL), dried over Na$_2$SO$_4$, concentrated and purified by flash chromatography (hexane:ether, 2:1) to give DW-15a as a colorless syrup (3.7 g, 54% from DW-13a).

DW-15b was prepared Similarly from DW-14b in 60% yield.

The synthesis of DW-16a was similar to the synthesis of DW-12 from DW-9. Colorless syrup. $[a]_D^{25}=-42.9°$ (c 0.49, $CH_2Cl_2$). $^1$H NMR: δ 4.73 (d, J=6.9 Hz, 1H), 4.64 (d, J=7.3 Hz, 1H), 4.62 (d, J=6.9 Hz, 1H), 4.57 (ddd, J=7.3, 4.2, 1.2 Hz, 1H), 4.34 (d, J=9.0 Hz, 1H), 3.8 (ddd, J=6.0, 4.2, 3.3 Hz, 1H), 3.78 (d, J=9.0 Hz, 1H), 3.34 (s, 3H), 2.44 (dd, J=15.2, 3.3 Hz, 1H), 2.29 (ddd, J=15.2, 6.0, 1.2 Hz, 1H), 1.5, 1.43, 1.4, 1.33 (s, each 3H). $^{13}$C NMR: δ 203.7, 111.6, 111.4, 95.01, 82.18, 79.91, 77.53, 72.3, 70.79, 55.78, 37.32, 26.68, 26.49, 26.11, 24.72. Anal. Calcd for $C_{15}H_{24}O_7$: C, 56.95; H, 7.65. Found: C, 56.74; H, 7.49.

DW-16b was prepared similarly from DW-15b. Colorless syrup. $[a]_D^{25}=-38.82°$ (c 0.76, $CH_2Cl_2$). IR (KBr): 1742 cm$^{-1}$. $^1$H NMR: δ 4.77 (d, J=6.9 Hz, 1H), 4.66 (d, J=6.9 Hz, 1H), 4.63 (d, J=6.9 HZ, 1H), 4.59 (ddd, J=6.9, 3.9, 1.5 Hz, 1H), 4.38 (d, J=9.0 Hz, 1H), 3.86 (ddd, J=6.0, 3.9, 3.0 Hz, 1H), 3.83 (d, J=9.0 Hz, 1H), 3.37 (s, 3H), 2.49 (dd, J=15.0, 3.0 Hz, 1H), 2.32 (ddd, J=15.0, 6.0, 1.5 Hz, 1H), 1.8–1.3 (m, 8H), 1.47, 1.43 (s, each 3H). 1.4 (br, 2H). Anal. Calcd for $C_{18}H_{28}O_7$: C, 60.66; H, 7.92. Found: C, 60.39; H, 7.76.

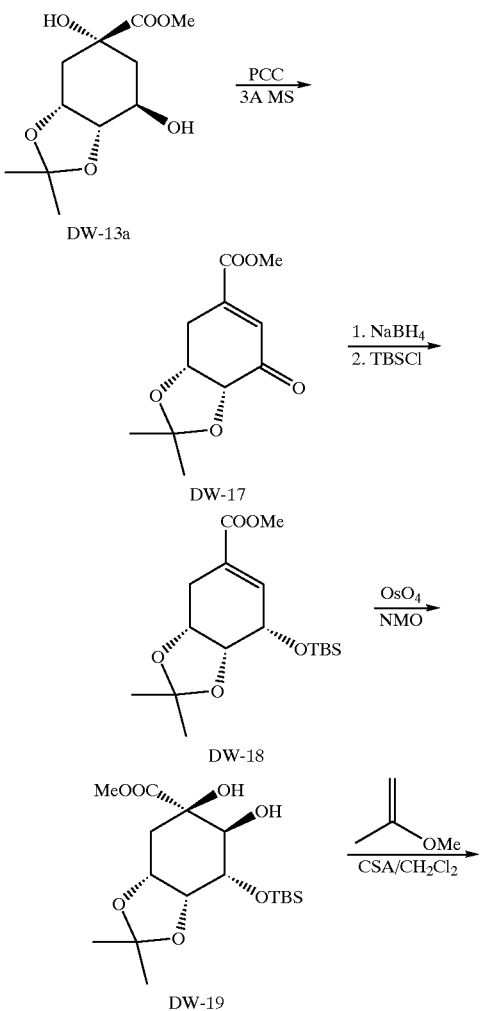

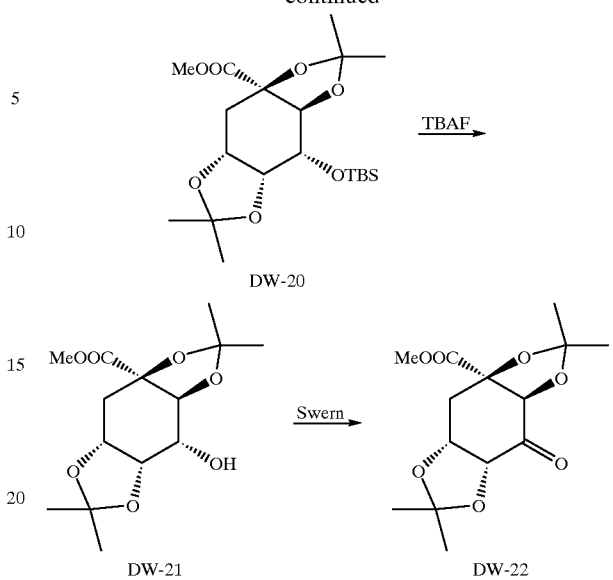

Preparation of DW-22

PCC (25 g, 116 mmol) and powdered 3A molecular sieve (17 g) were added to a solution of DW-13a (10 g, 40 mmol) and pyridine (10 mL) in dry $CH_2Cl_2$ (100 mL). After being stirred at room temperature for 24 hours, the reaction mixture was diluted with ether (300 mL), filtered through celite, and washed with ether. The filtrate was concentrated and purified with flash chromatography (hexane:ethyl acetate, 3:1) to give enone DW-17 as white needles (5.5 g, 60%).

$NaBH_4$ (1.0 g, 26 mmol) was added portionwise to a solution of enone DW-17 (5 g, 22.1 mmol) in MeOH (30 mL). After being stirred at room temperature for 0.5 hour, the reaction mixture was quenched with saturated aqueous $NH_4Cl$ (15 mL). After the removal of MeOH under reduced pressure, the resulting aqueous solution was extracted with $CH_2Cl_2$ (4×15 mL), washed with brine, dried over $Na_2SO_4$, and concentrated to give an allylic alcohol as a white solid (5 g, 98%) which was used for next step without further purification.

To a solution of the above allylic alcohol (3.2 g, 0.014 mol), Imidazole (1.7 g, 0.025 mol) and catalytic amount of DMAP in dry $CH_2Cl_2$ (50 mL), was added tert-butyldimethylsilyl chloride (3.0 g, 0.02 mol). After being stirred at room temperature for 2 hours, the reaction mixture was quenched with saturated aqueous $NH_4Cl$, extracted with ether (3×30 mL), washed with water and brine, dried over $Na_2SO_4$, concentrated and purified with flash chromatography (hexane:ether, 5:1, v/v) to give DW-18 as a colorless syrup (4.6 g, 96%).

$OsO_4$ (10 mg) was added to a solution of DW-18 (4.6 g, 13.5 mmol), NMO (2.8 g, 24 mmol), pyridine (7 mL), and water (1.4 mL) in t-BuOH (45 mL) at room temperature under $N_2$. The solution was refluxed under $N_2$ for 3 hours, then cooled to room temperature, and quenched with saturated aqueous $Na_2S_2O_5$ (15 mL). Upon removing the solvent under reduced pressure, the residue was purified by flash chromatography (hexane:ether, 1:1, v/v) to afford diol DW-19 as a colorless syrup (4.8 g, 95%).

To a solution of diol DW-19 (4.8 g, 12.8 mmol) and 2-methoxypropene (8 mL) in dry $CH_2Cl_2$ (80 mL) was added catalytic amount of CSA under $N_2$ at room temperature. The resulting solution was stirred for 2 hours, then quenched with triethylamine (0.5 mL). Upon removing the solvent, the resulting residue was purified by flash chromatography (hexane:ether, 10:1 to 5:1, the silica-gel was prebuffered with 1% triethylamine in hexane) to afford DW-20 as a colorless syrup (5.0 g, 94%).

DW-20 (1.6 g, 3.9 mmol) was dissolved in a solution of TBAF in THF (1M, 15 mL). After being stirred at room temperature for 1 hour, the reaction mixture was quenched with saturated aqueous $NH_4Cl$, extracted with ether (3×20 mL), washed with water and brine, dried ($Na_2SO_4$), concentrated and purified by flash chromatography (hexane:ether, 2:1 to 1:1, v/v) to give DW-21 as white crystals (0.82 g, 70%).

To a solution of DMSO (0.53 g, 6.7 mmol) in dry $CH_2Cl_2$ (2 mL) was added dropwise oxalyl chloride (0.29 mL, 3.3 mmol) under $N_2$ at −78° C. The mixture was stirred at −78° C. for 10 min, then removed from coolant and stirred for 3 min. Upon recooling to −78° C., a solution of alcohol DW-21 (0.67 g, 2.2 mmol) in dry $CH_2Cl_2$ (7 mL) was added in one portion. The resulting reaction mixture was stirred at −78° C. for additional 1 hour, then triethylamine (1.4 mL) was added dropwise. After being stirred at −78° C. for an another 10 mi, the reaction mixture was warmed to room temperature, quenched with saturated aqueous $NH_4Cl$ (5 mL), extracted with $CH_2Cl_2$ (3×20 mL), washed with water and brine, dried ($Na_2SO_4$), concentrated, and purified by flash chromatography (hexane:ether, 1:1 to 1:2, v/v) to give ketone DW-22 as a white solid (0.66 g, 99%). MP 66–68° C. (hexane). $[a]_D^{25}$=−1.9° (c 0.68, $CHCl_3$). IR (KBr): 3481 (hydrate), 1749 $cm^{-1}$. Ketone: $^1H$ NMR: δ 4.92 (s, 1H), 4.90 (dd, J=8.4, 0.7 Hz, 1H), 4.85 (ddd, J=8.5, 8.4, 3.9 Hz, 1H), 3.81 (s, 3H), 2.25 (ddd, J=14.4, 3.9, 0.7 Hz, 1H), 2.0 (dd, J 14.4, 8.5 Hz, 1H), 1.56, 1.49, 1.35, 1.34 (s, each 3H). $^{13}C$ NMR: δ 202.4, 171.4, 113.6, 110.9, 85.1, 79.9, 77.29, 73.42, 53.34, 36.12, 26.71, 26.33, 24.97, 24.35. Hydrate: $^1H$ NMR: 6 4.81 (s, 1H), 4.50 (ddd, J=8.8, 7.8, 5.1 Hz, 1H), 4.35 (d, J=7.8 Hz, 1H), 3.80 (s, 3H), 2.31 (dd, J=13.8, 5.1 Hz, 1H), 2.18 (dd, J=13.8, 8.8 Hz, 1H), 1.483, 1.481, 1.36, 1.33 (s, each 3H). $^{13}C$ NMR: δ 172.7, 110.5, 109.6, 93.73, 82.5, 79.51, 76.01, 71.64, 53.14, 33.94, 26.86, 26.33, 24.69, 24.26. Anal. Calcd for $C_{14}H_{20}O_7 \cdot 0.2H_2O$: C, 55.33; H, 6.77. Found: C, 55.35; H 6.64.

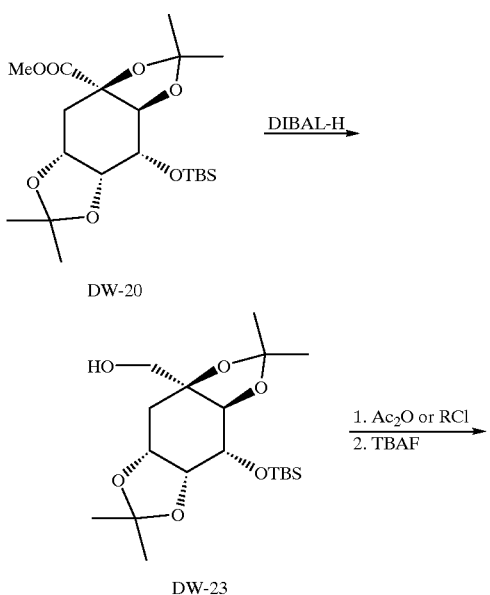

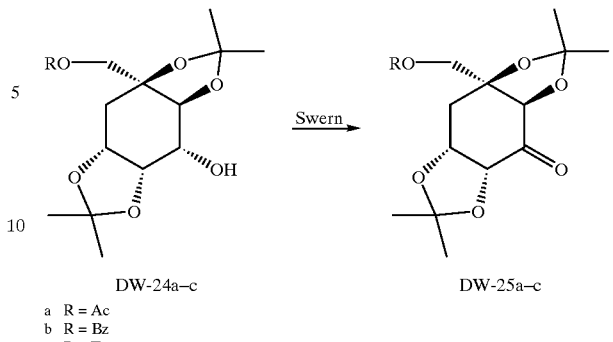

DW-24a–c      DW-25a–c a R = Ac
b R = Bz
c R = Ts

Preparation of DW-25a.

DIBAL-H (1.0 M in Hexane, 30 mL, 0.03 mol) was added dropwise to a solution of DW-20 (5.0 g, 0.0121 mol) in dry THF (30 mL) at −20° C. under $N_2$ over 30 min. After being stirred at 0° C. for 2 hours, the reaction mixture was quenched with saturated aqueous $NH_4Cl$ (10 mL) and filtered. The cake was washed with ether. The filtrate was extracted with ether, washed with brine, dried ($Na_2SO_4$), concentrated and purified by flash chromatography (hexane:ether, 2:1, v/v) to give DW-23 as a colorless syrup (4.3 g, 92.3%).

Acetic anhydride (0.4 mL, 4.2 mmol) was added to a solution of DW-23 (0.9 g, 2.33 mol), triethylamine (0.9 mL, 5.03 mmol), and catalytic amount of DMAP in dry $CH_2Cl_2$ (5 mL). After being stirred at room temperature for 2 hours, the reaction mixture was quenched with saturated aqueous $NH_4Cl$, extracted with $CH_2Cl_2$ (3×20 mL), washed with water and brine, dried over $Na_2SO_4$, and concentrated to give a colorless syrup which was used for next step directly.

The above crude acetate was dissolved in a solution of TBAF in THF (1 M, 8 mL). After being stirred at room temperature for 2 hours, the reaction mixture was quenched with saturated aqueous $NH_4Cl$, extracted with $CH_2Cl_2$ (4×15 mL), washed with water and brine, dried ($Na_2SO_4$), concentrated and purified by flash chromatography (hexane:ethyl acetate, 5:1 to 2:1, v/v) to afford DW-24a as white crystals (0.58 g, 86%).

To a solution of DMSO (0.41 g, 5.2 mmol) in dry $CH_2Cl_2$ (1.5 mL) was added dropwise oxalyl chloride (0.226 mL, 0.0026 mol) under $N_2$ at −78° C. The mixture was stirred at −78° C. for 10 min, then removed from coolant and stirred for 3 min. Upon recooling to −78° C., a solution of alcohol DW-24a (0.54 g, 0.00172 mol) in dry $CH_2Cl_2$ (5 mL) was added in one portion. After the mixture was stirred at −78° C. for additional 1 hour, triethylamine (1.1 mL) was added dropwise. The resulting mixture was stirred at −78° C. for an another 10 min, and warmed to room temperature. The reaction mixture was quenched with saturated aqueous $NH_4Cl$ (4 mL), extracted with $CH_2Cl_2$ (3×15 mL), washed with water and brine, dried over $Na_2SO_4$, concentrated and purified by flash chromatography (hexane:ether, 2:1 to 1:2, v/v) to give ketone DW-25a as a white solid (0.53 g, 95%). MP 72.5–74° C. (recrystallized from hexane). $[a]_D^{25}$=+11.2° (c 0.34, $CHCl_3$). IR (KBr): 3464 (hydrate), 1748 $cm^{-1}$. Ketone: $^1H$ NMR: δ 5.01 (dd, J=8.4, 0.6 Hz, 1H), 4.90 (ddd, J=10.2, 8.4, 4.5 Hz, 1H), 4.34 (s, 1H), 4.24, 4.04 (d, J=11.7, each 1H), 2.16 (ddd, J=14.1, 4.5, 0.6 Hz, 1H), 2.08 (s, 3H), 1.45 (dd, J=14.1, 10.2 Hz, 1H), 1.55, 1.50, 1.39, 1.36 (s, each 3H). $^{13}C$ NMR: δ 203.3, 170.6, 112.9, 110.5, 84.33, 81.09, 77.74, 73.28, 67.55, 36.78, 27.04, 26.98, 26.15, 24.56, 20.89. Hydrate: $^1H$ NMR: δ 4.50 (ddd, J=10.6, 7.5, 5.7 Hz, 1H), 4.41 (d, J=7.5 Hz, 1H), 4.25, 4.05 (d, J=11.5 Hz, each 1H), 4.11 (s, 1H), 2.08 (dd, J=13.5, 5.7 Hz, 1H), 2.09 (s, 3H), 1.60 (dd, J=13.5, 10.6 Hz, 1H), 1.50, 1.45, 1.40, 1.39 (s, each 3H). $^{13}C$ NMR: δ 170.8, 110.5, .109.7, 94.12 (hydrate C), 81.9, 80.11, 76.33, 72.0, 68.87, 34.69, 27.46, 27.24, 26.03, 25.04, 21.05. Anal. Calcd for $C_{15}H_{22}O_7 \cdot 0.8H_2O$: C, 54.80; H, 7.10. Found: C, 54.79; H, 7.03.

Preparation of DW-25b.

Benzoyl chloride (0.3 mL, 2.5 mmol) was added to a solution of alcohol DW-23 (0.77 g, 2 mmol), triethylamine (0.5 mL), and catalytic amount of DMAP in dry $CH_2Cl_2$ (5 mL). After being stirred at room temperature for 2 hours, the reaction mixture was quenched with saturated aqueous $NH_4Cl$, extracted with $CH_2Cl_2$ (3×20 mL), washed with water and brine, dried over $Na_2SO_4$, and concentrated to give a crude benzoate.

The above crude benzoate was dissolved in a solution of TBAF in THF (1 M, 8 mL). After being stirred at room temperature for 1 hour, the reaction mixture was quenched with saturated aqueous $NH_4Cl$, extracted with ether, washed with water and brine, dried ($Na_2SO_4$), concentrated and purified by flash chromatography (hexane:ethyl acetate, 2;1, v/v) to give DW-24b as a colorless syrup (0.75 g, 99%).

To a solution of DMSO (0.453 g, 5.8 mmol) in dry $CH_2Cl_2$ (2 mL) was added dropwise oxalyl chloride (0.254 mL, 2.9 mmol) under $N_2$ at −78° C. The mixture was stirred at −78° C. for 10 min, then removed from coolant and stirred for 3 min. Upon recooling to −78° C., a solution of alcohol DW-25b (0.73 g, 1.93 mmol) in dry $CH_2Cl_2$ (6 mL) was added in one portion. After the mixture was stirred at −78° C. for additional 1 hour, triethylamine (1.1 mL) was added dropwise. The resulting mixture was stirred at −78° C. for an another 10 min, warmed to room temperature, quenched with saturated aqueous $NH_4Cl$ (4 mL), extracted with $CH_2Cl_2$ (3×20 mL), washed with water and brine, dried over $Na_2SO_4$, concentrated and purified by flash chromatography (hexane:ether, 2:1 to 1:2, v/v) to give ketone DW-25b as a colorless syrup (0.71 g, 96%). $[a]_D^{25}$=+21.00 (c 0.84, $CHCl_3$). IR (KBr): 3468 (hydrate), 1749, 1724 cm$^{-1}$. $^1H$ NMR: δ 8.04 (m, 2H), 7.57 (m, 1H), 7.45 (m, 2H), 5.07 (d, J=8.4 Hz, 1H), 4.94 (ddd, J=10.2, 8.4, 4.5 Hz, 1H), 4.50 (s, 1H), 4.42 (d, J=11.4 Hz, 1H), 4.36 (d, J=11.4 Hz, 1H), 2.27 (dd, J=14.4, 4.5 Hz, 1H), 1.60 (dd, J=14.4, 10.2 Hz, 1H), 1.58, 1.52, 1.41, 1.39 (s, each 3H). $^{13}C$ NMR: δ 203.3, 166.1, 133.6, 130.0, 129.9, 128.7, 113.0, 110.5, 84.45, 81.45, 77.72, 73.33, 68.42, 36.93, 27.01, 27.0, 26.2, 24.56. Anal. Calcd for $C_{20}H_{24}O_7 \cdot H_2O$: C, 60.91; H, 6.64. Found: C, 60.85; H, 6.25.

Preparation of DW-25c:

TsCl (0.475 g, 2.5 mmol) was added to a solution of DW-23 (0.77 g, 2 mmol), pyridine (0.5 mL), and catalytic amount of DMAP in dry $CH_2Cl_2$ (5 mL) at 0° C. After being stirred at room temperature for 30 hours, the reaction mixture was quenched with saturated aqueous $NH_4Cl$, extracted with $CH_2Cl_2$ (3×20 mL), washed with water and brine, dried over $Na_2SO_4$, and concentrated to give the crude compound.

The above crude compound was dissolved in a solution of TBAF in THF (1 M, 10 mL). After being stirred at room temperature for 1 hour, the reaction mixture was quenched with saturated aqueous $NH_4Cl$, extracted with ether, washed with water and brine, dried ($Na_2SO_4$), concentrated, and purified by flash chromatography (hexane:ethyl acetate, 2:1, v/v) to give DW-24c as white crystals (0.7 g, 82%).

To a solution of DMSO (0.375 g, 4.8 mmol) in dry $CH_2Cl_2$ (1.5 mL) was added dropwise oxalyl chloride (0.21 mL, 2.4 mmol) under $N_2$ at −78° C. The mixture was stirred at −78° C. for 10 min, then removed from coolant and stirred for 3 min. Upon recooling to −78° C., a solution of alcohol DW-24c (0.67 g, 1.55 mol) in dry $CH_2Cl_2$ (4.5 mL) was added in one portion. After the mixture was stirred at −78° C. for 1 hour, triethylamine (1.05 mL) was added dropwise. The resulting mixture was stirred at −78° C. for an another 10 min, warmed to room temperature, quenched with saturated aqueous $NH_4Cl$ (4 mL), extracted with $CH_2Cl_2$ (3(15 mL), washed with water and brine, dried over $Na_2SO_4$, concentrated, and purified by flash chromatography (hexane:ethyl acetate, 5:1 to 1:1, v/v) to give ketone DW-25c as a colorless syrup (0.67 g, 100%). $[a]_D^{25}$=+4.3° (c 0.81, $CHCl_3$) IR (KBr): 3480 (hydrate), 1749, 1177, 990 cm$^{-1}$. $^1H$ NMR: δ 7.79 (d, J=8.4 Hz, 2H), 7.35 (d, J=8.4 Hz, 2H), 4.91 (d, J=8.1 Hz, 1H), 4.81 (ddd, J=9.3, 8.1, 4.2 Hz, 1H), 4.33 (s, 1H), 4.07 (d, J=10.2 Hz, 1H), 4.02 (d, J=10.2 Hz, 1H), 2.44 (s, 3H), 2.07 (dd, J=14.4, 4.2 Hz, 1.48 (dd, J=4.4, 9.3 Hz, 1H) 1.49, 1.45, 1.34, 1.31 (s, each 3H). $^{13}C$ NMR: δ 202.9, 145.5, 130.2, 130.0, 128.2, 113.3, 110.7, 83.95, 80.13, 77.57, 73.25, 71.91, 36.04, 27.21, 26.73, 26.26, 24.38, 21.81.

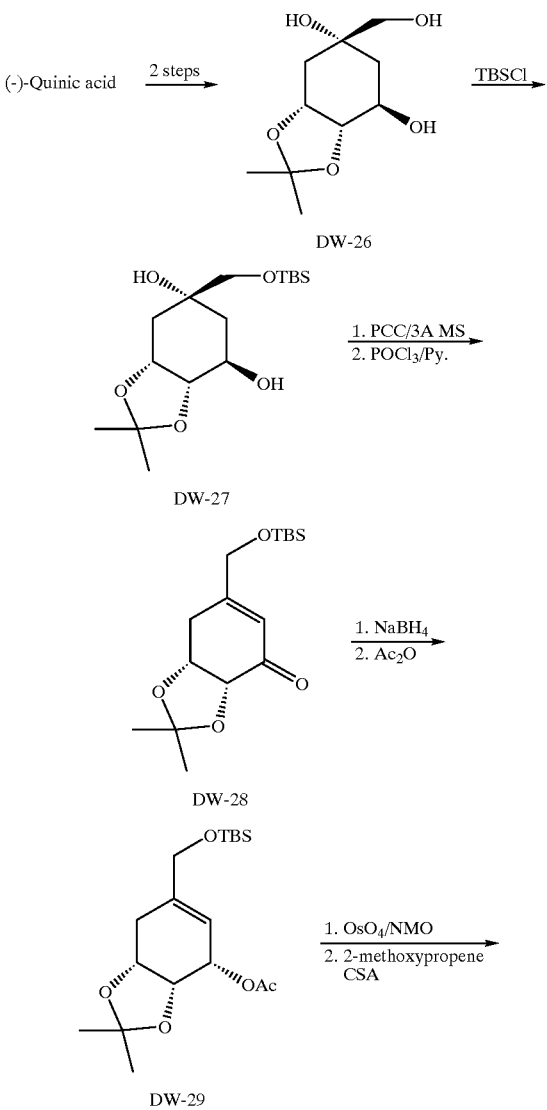

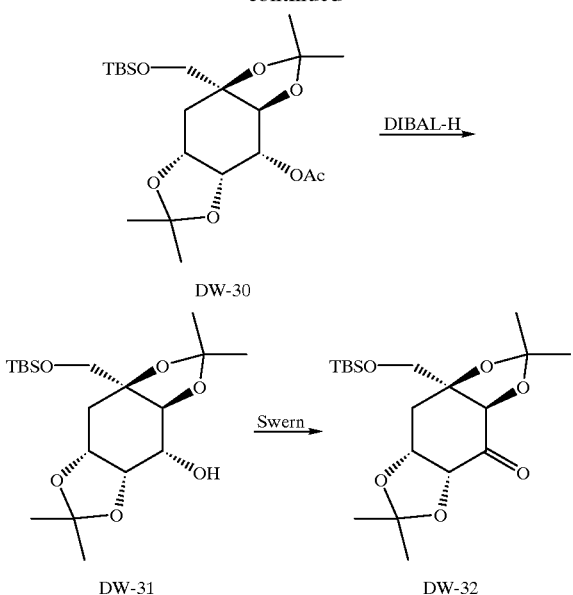

Preparation of DW-32.

After the lactone (6.2 g, 29.4 mmol) prepared from (−)-quinic acid (see the preparation of DW-16a) was dissolved in EtOH (120 mL), NaBH$_4$ (4 g) was added. After being stirred at room temperature for 15 hours, saturated aqueous NaCl (50 mL) was added, and the mixture was stirred for an another 15 hour. Upon removing EtOH and water under reduced pressure, the resulting solid was extracted with CH$_2$Cl$_2$/MeOH (2/1, v/v). The extracts was concentrated and the residue was recrystallized from EtOH to give triol DW-26 as white crystals (6.2 g, 98%).

To a solution of triol DW-26 (4.1 g, 18.8 mmol), imidazole (1.9 g, 33 mmol), and catalytic amount of DMAP in dry CH$_2$Cl$_2$ (50 mL) was added portionwise tert-butyldimethylsilyl chloride (3.5 g, 23 mmol) at 0° C. After being stirred at 0° C. for 2 hours, the reaction mixture was diluted with ether (100 mL), filtered through a thin silica-gel, and washed with ether (200 mL). The filtrate was concentrated to give DW-27 as a colorless oil (5.5 g), which was used for next step directly.

After the crude DW-27 (5.5 g) was dissolved in CH$_2$Cl$_2$ (100 mL), powdered 3A MS (7 g), PCC (9 g, 41.7 mmol), and pyridine (5 mL) were added. After being stirred at room temperature overnight, the reaction mixture was diluted with ether (300 mL), filtered through thin silica-gel, and washed with ether. The filtrate was concentrated to give a colorless syrup. After the syrup was dissolved in pyridine (20 mL), the POCl$_3$ (2 mL) was added, the reaction mixture was stirred at room temperature for 16 hours, quenched with saturated aqueous NH$_4$Cl and ether, extracted with ether (3×50 mL), washed with water and brine, dried over Na$_2$SO$_4$, concentrated, purified by flash chromatography (hexane:ethyl acetate, 4:1, v/v) to afford enone DW-28 as a colorless syrup (3.1 g, 54% yield from DW-26).

To a solution of enone DW-28 (1.1 g, 3.4 mmol) in EtOH (10 mL) was added NaBH$_4$ (0.3 g, 7.6 mmol). After being stirred at room temperature for 2 hours, the reaction mixture was quenched with saturated aqueous NH$_4$Cl (10 mL), extracted with CH$_2$Cl$_2$ (5×20 mL), washed with water, and brine, dried (Na2SO4), and concentrated to give a crude alcohol.

After the above crude alcohol was dissolved in dry CH$_2$Cl$_2$ (10 mL), pyridine (0.7 mL), acetic anhydride (0.7 mL), and catalyst amount of DMAP were added. After being stirred at room temperature for 10 hours, the reaction mixture was quenched with saturated aqueous NH$_4$Cl, extracted with CH$_2$Cl$_2$ (3×20 mL), washed with water and brine, dried over Na$_2$SO$_4$, concentrated, and purified by flash chromatography (hexane:ether, 3:1, v/v) to give DW-29 as a colorless syrup (1.2 g, 96%).

OsO$_4$ (10 mg) was added to a solution of DW-29 (1.2 g, 3.5 mmol), NMO (0.65 g, 5.5 mmol), pyridine (1.75 mL), and water (0.35 mL) in t-BuOH (10 mL) at room temperature under N$_2$. After being refluxed under N$_2$ for 3 hours, the reaction mixture was cooled to room temperature and quenched with saturated aqueous Na$_2$S$_2$O$_5$ (5 mL). Upon removing the solvent under reduced pressure, the resulting residue was purified by flash chromatography (hexane:ether, 1:1, v/v) to afford a diol as a colorless syrup (1.0 g, 85%). [a]$_D^{25}$=−31.60 (c 0.67, CHCl$_3$). IR (KBr): 3432, 3380, 1739, 1253, 1080 cm$^{-1}$. $^1$H NMR: δ5.28 (dd, J=9.9, 3.9 Hz, 1H), 4.47–4.35 (m, 2H), 4.0 (dd, J=9.9, 4.5 Hz, 1H), 3.7 (d, J=9.6 Hz, 1H), 3.6 (d, J=9.6 Hz, 1H), 2.94 (d, J=4.5 Hz, 1H, OH), 2.77 (s, 1H, OH), 2.18 (s, 3H), 1.95 (dd, J=14.4, 6.3 Hz, 1H), 1.67 (dd, J=14.4, 8.1 Hz, 1H), 1.50, 1.32, (s, each 3H), 0.88 (s, 9H), 0.078 (s, 6H). $^{13}$C NMR: δ 171.4, 109.7, 74.63, 73.54, 72.67, 72.26, 70.21, 69.44, 34.8, 28.33, 26.14, 26.0, 21.39, 18.35, −5.35, −5.38. Anal. Calcd for C$_{18}$H$_{34}$O$_7$Si: C, 55.35; H, 8.77. Found: C, 55.44; H, 8.57.

To a solution of the above diol (0.8 g, 2 mmol) and 2-methoxypropene (1.3 mL) in dry CH$_2$Cl$_2$ (15 mL) was added catalytic amount of CSA under N$_2$ at room temperature. After being stirred for 2 hours, the reaction mixture was quenched with triethylamine (0.1 mL), concentrated, and purified by flash chromatography (hexane:ether, 10:1 to 5:1, the silica-gel was prebuffered with 1% triethylamine in hexane) to afford DW-30 as a colorless syrup (0.81 g, 96%).

To a solution of DW-30 (0.81 g, 1.88 mmol) in dry THF (10 mL) was added dropwise DIBAL-H solution (1.0 M in hexane, 6 mL) at −20° C. over 30 min. After being stirred at 0° C. for 3 hours, the reaction mixture was quenched with saturated aqueous NH$_4$Cl (3 mL), filtered, and washed with ether. The filtrate was concentrated and purified by flash chromatography (hexane:ether, 2:1, v/v) to give DW-31 as a colorless syrup (0.75 g, 94%).

To a solution of DMSO (0.422 g, 5.4 mmol) in dry CH$_2$Cl$_2$ (1.5 mL) was added dropwise oxalyl chloride (0.250 mL, 2.7 mmol) under N$_2$ at −78° C. The mixture was stirred at −78° C. for 10 min, then removed from coolant and stirred for 3 min. Upon recooling to −78° C., a solution of alcohol DW-31 (0.70 g, 1.8 mmol) in dry CH$_2$Cl$_2$ (6 mL) was added in one portion. After the mixture was stirred at −78° C. for 1 hour, triethylamine (1.23 mL) was added dropwise. After being stirred at −78° C. for an another 10 min and warmed to room temperature, the reaction mixture was quenched with saturated aqueous NH$_4$Cl (4 mL), extracted with CH$_2$Cl$_2$ (3×20 mL), washed with water and brine, dried over Na$_2$SO$_4$, concentrated, and purified by flash chromatography (hexane:ether, 5:1 to 2:1, v/v) to give ketone DW-32 as a colorless syrup (0.63 g, 90%). [a]$_D^{25}$=+22.60 (c 1.23, CHCl$_3$). IR (KBr): 1752 cm$^{-1}$. $^1$H NMR: δ 5.05 (d, J=8.4 Hz, 1H), 4.93 (m, 1H), 4.33 (s, 1H), 3.64 (d, J=10.5 Hz, 1H), 3.57 (d, J=10.5, 1H), 2.08 (ddd, J=14.4, 4.8, 2.7 Hz, 1H), 1.42 (ddd, J=14.4, 3.0, 2.4 Hz, 1H), 1.56, 1.49 (s, each 3H), 1.38 (s, 6H), 0.88 (s, 9H), 0.06, 0.05 (s, each 3H). $^{13}$C NMR: δ 203.4, 112.3, 110.1, 86.38, 81.26, 77.76, 73.48, 67.67, 36.69, 27.24, 27.05, 26.41, 25.99, 24.82, 18.47, −5.26, −5.44. Anal. Calcd for C$_{19}$H$_{34}$O$_6$Si 1.5 H$_2$O: C, 55.18; H, 9.01. Found: C, 54.99; H, 8.69.

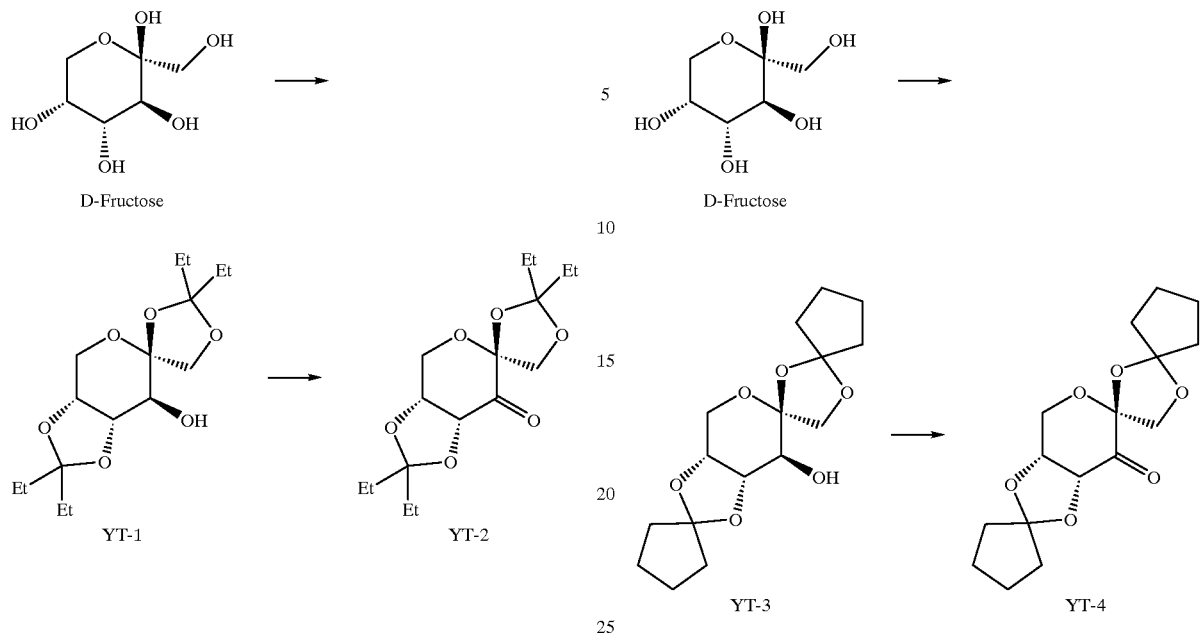

D-Fructose

YT-1

YT-2

D-Fructose

YT-3

YT-4

Preparation of YT-2.

To a solution of 3-pentanone (10.6 mL, 8.6 g, 100 mmol) and trimethyl orthoformate (8.8 mL, 8.5 g, 80 mmol) in methanol (50 mL) was added TsOH.H$_2$O (0.01 g). After the solution was heated at 60–70° C. for 3 hours (during this time methyl formate formed was distilled off), the bath temperature was raised to 90° C. and maintained at that temperature for 30 minutes to distill off the methanol. Upon cooling to room temperature, dioxane (100 mL) and D-fructose (7.2 g) were added. The reaction mixture was cooled in an ice bath, and 0.1 mL of 70% perchloric acid was added. After being stirred for 6 hours, the reaction was quenched by adding triethylamine and concentrated. The resulting residue was dissolved in dichloromethane (50 mL), washed with brine, dried over sodium sulfate, concentrated, and purified by flash chromatography (hexane:ether, 20:1 to 2:1, v/v) to give alcohol YT-1 as a syrup (7.8 g, 61%).

PCC (11.8 g, 55 mmol) was added portionwise over 15 min to a mixture of alcohol YT-1 (7.52 g, 24 mmol) and powdered 3A molecular sieves (22 g, activated at 180–200° C. under vacuum) in dichloromethane (100 mL). After the reaction mixture was stirred for 3 hours under nitrogen, it was filtered through celite and washed carefully with ether. The filtrate was concentrated and the residue was purified by passing through a short silica gel column (hexane:ether, 1:1, v/v) to afford a syrup (YT-2) which solidified in refrigerator after a few hours (1.47 g, 81%). $^1$H NMR: δ 4.71 (d, J=5.9, 1H), 4.62 (d, J=9.2 Hz, 1H), 4.58 (ddd, J=5.9, 2.3, 1.0 Hz, 1H), 4.39 (dd, J=13.5, 2.3 Hz, 1H), 4.14 (d, J=13.5 Hz, 1H), 3.96 (d, J=9.3 Hz, 1H). $^{13}$C NMR: δ 197.5, 118.4, 114.9, 114.2, 104.2, 77.73, 75.71, 70.65, 60.67, 30.71, 29.96, 29.16, 29.08, 8.60, 8.47, 8.44, 7.82. Anal. Cald. for $C_{16}H_{26}O_6$: C, 61.12; H, 8.34. Found: C, 61.36; H, 8.17.

Preparation of Ketone YT-4

Perchloric acid (70%) (0.1 g) was added to a suspension of D-fructose (1.8 g, 10 mmol) in cyclopentanone (30 mL) and 1,1-dimethoxycyclopentane (2.86 g, 22 mmol) at 0° C. (ice bath). After being stirred under nitrogen at 0° C. for 6 hours, the reaction mixture was neutralized with con. ammonium hydroxide and concentrated. The resulting residue was dissolved in CH$_2$Cl$_2$ (20 mL), washed with brine, dried over sodium sulfate, concentrated, and purified by flash chromatography (hexane:ether, 20:1 to 2:1, v/v), and followed by recrystallization (hexane) to give alcohol YT-3 as a white needle (1.15 g, 36.9%).

PCC (1.86 g, 8.6 mmol) was added portionwise over 15 min to a mixture of alcohol YT-3 (1.0 g, 3.2 mmol) and powdered 3A molecular sieves (3.5 g) in dichloromethane (100 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-4 as colorless crystal (0.83 g, 83%). IR: 1745 cm$^{-1}$. $^1$H NMR: δ 4.73 (d, J=5.5 Hz, 1H), 4.51 (d, J=9.5 Hz, 1H), 4.44 (ddd, J=5.5, 2.1, 0.9 Hz, 1H), 4.38 (dd, J=13.4, 2.1 Hz, 1H), 4.12 (d, J=13.4 Hz, 1H), 3.87 (d, J=9.5 Hz, 1H), 2.00–1.63 (m, 16H). $^{13}$C NMR: δ 196.8, 123.2, 120.5, 104.0, 78.36, 75.78, 70.03, 60.46, 37.41, 37.04, 36.87, 36.16, 23.91, 23.71, 23.41, 23.21. Anal. Calcd. for $C_{16}H_{22}O_6$: C, 61.9; H, 7.1. Found: C, 61.66; H, 7.21.

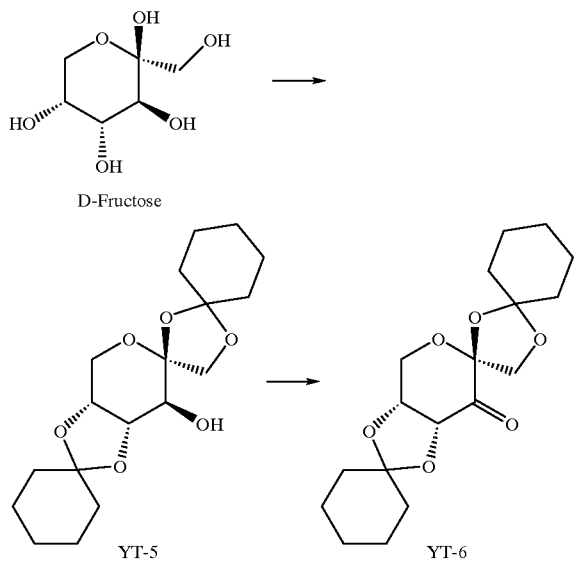

D-Fructose

YT-5   YT-6

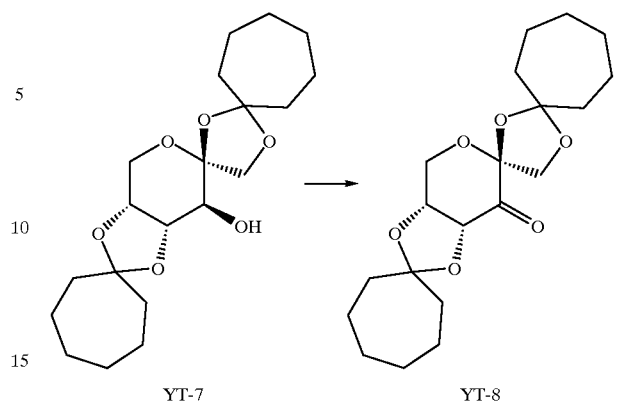

YT-7   YT-8

Preparation of Ketone YT-6

To a solution of con. sulfuric acid (3 mL) in cyclohexanone (40 mL) at 0° C. was added powered D-fructose (20.0 g, 111.1 mmol). The reaction mixture solidified after 40 min stirring at 0° C. After being stood at room temperature for additional 24 hours, the reaction mixture was dissolved in chloroform (150 mL) and washed with saturated sodium carbonate, brine, saturated ammonium chloride, water, brine, dried over magnesium sulfate, concentrated, and recrystallized (hexane) to give alcohol YT-5 as a white needle (13.6 g, 36.0%).

PCC (17.46 g, 81 mmol) was added portionwise over 15 min to a mixture of alcohol YT-5 (10.2 g, 30 mmol) and powdered 3A molecular sieves (31.8 g) in dichloromethane (150 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-6 as a white solid (8.11 g, 80.0%). $^1$H NMR: δ 4.75 (d, J=5.7 Hz, 1H), 4.59 (d, J=9.5 Hz, 1H), 4.55 (ddd, J=5.6, 2.2, 0.8 Hz, 1H), 4.39 (dd, J=13.5, 2.2 Hz, 1H), 4.13 (d, J=13.5 Hz, 1H), 3.98 (d, J=9.5 Hz, 1H), 1.79 (t, J=6.1 Hz, 2H), 1.68–1.57 (m, 14H), 1.41 (bs, 4H). $^{13}$C NMR: δ 197.5, 114.8, 111.5, 103.9, 77.78, 75.73, 69.79, 60.46, 36.49, 36.36, 35.65, 35.49, 25.11, 25.07, 24.15, 24.10, 23.95, 23.91. Anal. Calcd. for $C_{18}H_{26}O_6$: C, 63.89; H, 7.74. Found: C, 63.96; H, 7.72.

Preparation of Ketone YT-8

To a solution of cycloheptanone (23.6 mL, 22.4 g, 200 mmol) and trimethyl orthoformate (11.3 mL, 10.6 g, 100 mmol) in methanol (50 mL) was added TsOH.H$_2$O (0.05 g). After the solution was heated at 50–60° C. for 3 hours (during this time methyl formate formed was distilled off), the bath temperature was raised to 90° C. and maintained at that temperature for 30 minutes to distill off the methanol. Upon cooling to room temperature, dioxane (50 mL) and D-fructose (9.0 g, 50 mmol) were added. The reaction mixture was cooled in an ice bath, and 1 mL of 70% perchloric acid was added. After being stirred for 6 hours, the reaction mixture was neutralized by adding triethylamine and concentrated. The resulting residue was dissolved in dichloromethane (80 mL), washed with brine, dried over sodium sulfate, concentrated, and purified by flash chromatography (hexane:ether, 20:1 to 2:1) to give alcohol YT-7 as a white solid (3.64 g, 21.8%).

PCC (3.4 g, 16 mmol) was added portionwise over 15 min to a mixture of alcohol YT-7 (2.51 g, 6.8 mmol) and powdered 3A molecular sieves (7.0 g) in dichloromethane (50 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-8 as a white solid (2.25 g, 90.1%). $^1$H NMR: δ 4.68 (d, J=5.6 Hz, 1H), 4.52 (d, J=9.5 Hz, 1H), 4.46 (ddd, J=5.6, 2.1, 0.8 Hz, 1H), 4.33 (dd, J=13.4, 2.1 Hz, 1H), 4.08 (d, J=13.4 Hz, 1H), 3.91 (d, J=9.5 Hz, 1H), 2.00–1.40 (m, 24H). $^{13}$C NMR: δ 197.5, 118.8, 115.5, 104.0, 77.50, 69.86, 60.43, 40.26, 39.48, 38.83, 38.73, 29.48, 29.07, 25.58, 22.46, 22.44, 22.25. Anal. Calcd. for $C_{20}H_{30}O_6$: C, 65.55; H, 8.27. Found: C, 65.81; H, 8.17.

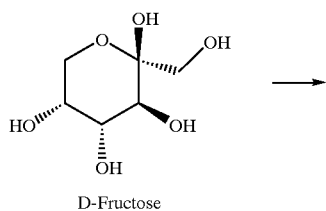

D-Fructose

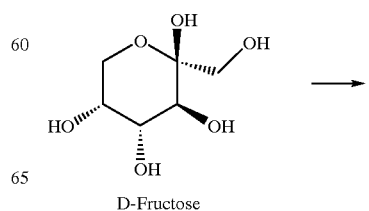

D-Fructose

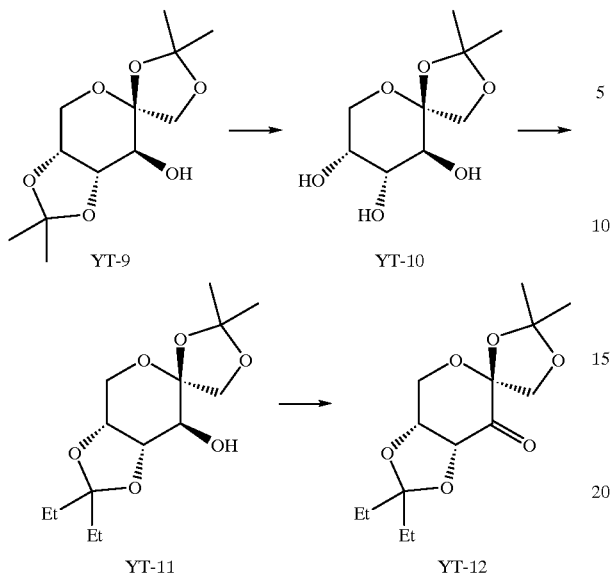

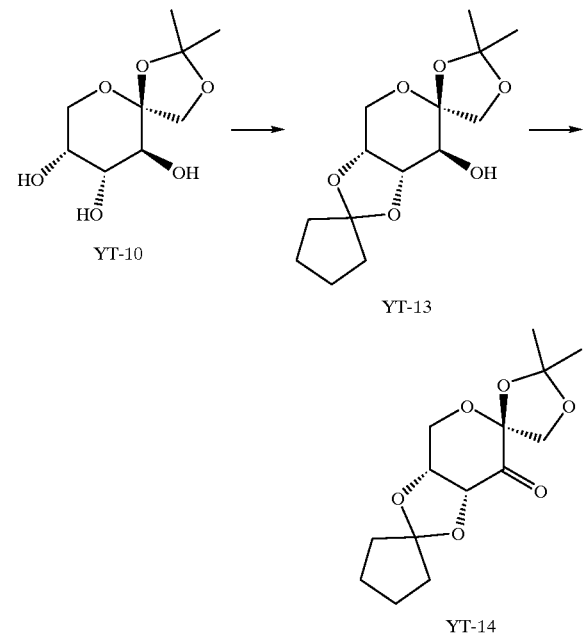

Preparation of Ketone YT-12

Perchloric acid (70%) (8.6 mL) was added to a suspension of D-fructose (36.84 g, 204.7 mmol) in acetone (740 mL) and 2,2-dimethoxypropane (14.8 mL, 120 mmol) at 0° C. (ice bath). After being stirred under nitrogen at 0° C. for 6 hours, the reaction mixture was neutralized with con. ammonium hydroxide and concentrated. The resulting solid residue was recrystallized from hexane-$CH_2Cl_2$ (4:1, v/v) to afford alcohol YT-9 as white needles (28.34 g, 53.2%).

To a solution of alcohol YT-9 (13.34 g, 51 mmol) in 150 mL of acetonitrile-water (9 : 1, v/v) was added DDQ (1.13 g, 5 mmol). After the mixture was stirred at room temperature for 6 hours, the solvent was evaporated. The resulting reddish solid residue was dissolved in ethyl acetate, dried over sodium sulfate, and concentrated to give alcohol YT-10 as a reddish solid (9.98 g, 88%).

To a solution of 3,3-dimethoxylpentane (4.41 g, 30 mmol) in 3-pentanone (22 mL) were added cupric sulfate (1.0 g) and con. sulfuric acid (0.05 g). After the mixture was stirred for 5 min, alcohol YT-10 (2.97 g, 13.5 mmol) was added. After being stirred additional 3.5 hours at room temperature, the reaction mixture was neutralized with triethylamine (0.8 mL) and filtered. The filtrate was concentrated and purified by flash chromatography (hexane:ether, 20:1 to 2:1, v/v) to afford alcohol YT-11 as a syrup (2.39 g, 61.5%).

PCC (4.10 g, 19.0 mmol) was added portionwise over 15 min to a mixture of alcohol YT-11 (2.03 g, 7.0 mmol) and powdered 3A molecular sieves (8.2 g) in dichloromethane (60 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-12 as a white solid (1.61 g, 79%). IR: 1750 $cm^{-1}$. $^1H$ NMR: δ 4.68 (d, J=5.9 Hz, 1H), 4.61–4.55 (m, 2H), 4.35 (dd, J=13.5, 2.2 Hz, 1 H), 4.12 (d, J=13.5 Hz, 1H), 3.98 (d, J=9.6 Hz, 1H), 1.70–1.61 (m, 4H), 1.55 (s, 3H), 1.40 (s, 3H), 0.92 (t, J=7.4, 3H), 0.91 (t, J=7.4 Hz, 3H). $^{13}C$ NMR: δ 197.5, 114.9, 114.0, 104.2, 76.67, 75.69, 70.48, 60.64, 29.91, 29.18, 26.72, 26.13, 8.56, 8.36. Anal. Calcd. for $C_{14}H_{22}O_6$: C, 58.73; H, 7.74. Found: C, 58.51; H, 7.58.

Preparation of Ketone YT-14

To a solution of 1,1-dimethoxylcyclopentane (3.9 g, 30 mmol) in cyclopentanone (20 mL) was added a solution of cupric sulfate (6.0 g) and con. sulfuric acid (0.2 g) in dioxane (20 mL). Upon stirring for 5 min, alcohol YT-10 (5.50 g, 25 mmol) was added. After being stirred 1.5 hours at room temperature, the reaction mixture was neutralized by adding triethylamine (1.0 mL) and filtered. The filtrate was concentrated and purified by flash chromatography (hexane:ether, 20:1 to 3:2) to give alcohol YT-13 (2.45 g, 33.6%).

PCC (1.85 g, 19 mmol) was added portionwise over 15 min to a mixture of alcohol YT-13 (0.91 g, 3.2 mmol) and powdered 3A molecular sieves (8.2 g) in dichloromethane (60 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-14 as a white solid (0.69 g, 76%). IR: 1743 $cm^{-1}$. $^1H$ NMR: δ 4.72 (d, J=5.3 Hz, 1H), 4.61 (d, J=9.5 Hz, 1H), 4.44–4.36 (m, 2H), 4.13 (d, J=13.1 Hz, 1H), 3.98 (d, J=9.5 Hz, 1H), 2.05–1.65 (m, 8H), 1.55 (s, 3H), 1.40 (s, 3H). $^{13}C$ NMR: δ 196.8, 120.5, 114.0, 104.3, 78.38, 75.80, 70.13, 60.22, 37.44, 37.07, 26.72, 26.23, 23.75, 23.44. Anal. Calcd. for $C_{14}H_{20}O_6$: C, 59.14; H, 7.09. Found: C, 58.96; H, 7.26.

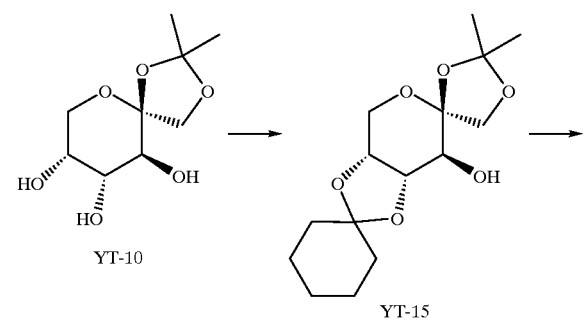

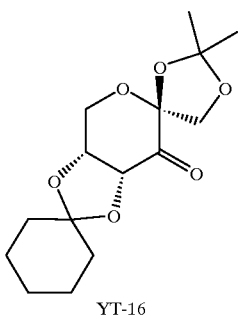

YT-16

Preparation of Ketone YT-16

To a mixture of alcohol YT-10 (2.91 g, 13.2 mmol) in cyclohexaone (30 mL) and 1,1-dimethoxylcyclohexane (5.0 mL) were added cupric sulfate (5.0 g) and con. sulfuric acid (0.05 g). After being stirred for 50 min at room temperature under nitrogen, the reaction mixture was neutralized with triethylamine (1.0 mL) and filtered. The filtrate was concentrated and purified by flash chromatography (hexane:ether, 20:1 to 3:2) to give alcohol YT-15 (2.60 g, 65.5%).

PCC (5.06 g, 23.5 mmol) was added portionwise over 15 min to a mixture of alcohol YT-15 (2.60 g, 8.7 mmol) and powdered 3A molecular sieves (10.0 g) in dichloromethane (50 mL). After being stirred for 3 hours under nitrogen, the reaction mixture was filtered through celite and washed carefully with ether. The filtrate was concentrated and purified by passing through a short silica gel column (hexane:ether, 20:1 to 8:1, v/v) to afford YT-16 as a white solid (1.89 g, 76%). $^1$H NMR: δ 4.72 (d, J=5.6 Hz, 1H), 4.60 (d, J=9.5 Hz, 1H), 4.55 (dd, J=5.6, 2.2 Hz, 1H), 4.37 (dd, J=13.4, 2.2 Hz, 1H), 4.13 (d, J=13.4, 1H), 3.98 (d, J=9.5 Hz, 1H), 1.62–1.34 (m, 10H), 1.55 (s, 3H), 1.40 (s, 3H). $^{13}$C NMR: δ 197.4, 113.9, 111.5, 104.3, 77.71, 75.66, 70.21, 60.43, 36.90, 35.61, 26.67, 26.16, 25.09, 24.07, 23.91. Anal. Calcd. for $C_{15}H_{20}O_6$: C, 60.39; H, 7.43, Found: C, 60.42; H, 7.47.

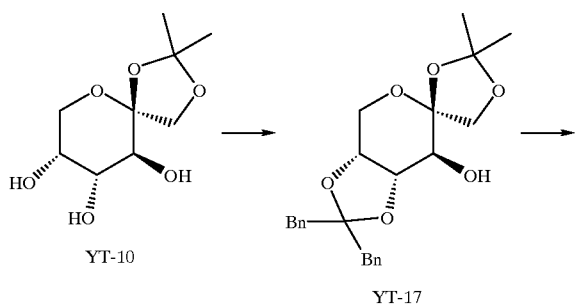

YT-10

YT-17

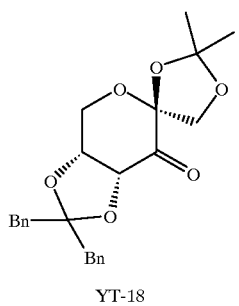

YT-18

Preparation of Ketone YT-18

To a solution of 2,2-dimethoxy-1,3-diphenylpropane (5.12 g, 20 mmol) in dioxane (50 mL), were added cupric sulfate (1.5 g) and con. sulfuric acid (0.12 g), followed by alcohol YT-17 (3.30 g, 15 mmol). After being stirred 3 hours at room temperature under nitrogen, the reaction mixture was neutralized with triethylamine and filtered. The filtrate was concentrated and purified by flash chromatography (hexane:ether, 17:1 to 2:1, v/v) to give alcohol YT-17 (2.94 g, 47.6%).

PCC (4.01 g, 18.6 mmol) was added portionwise over 15 min to a mixture of alcohol YT-17 (2.84 g, 6.9 mmol) and powdered 3A molecular sieves (8.02 g) in dichloromethane (50 mL). After being stirred for 3 hours under nitrogen, the reaction mixture was filtered through celite and washed carefully with ether. The filtrate was concentrated and purified by passing through a short silica gel column (hexane:ether, 20:1 to 2:1, v/v) to afford YT-18 as a white solid (1.96 g, 69.4%). $^1$H NMR: δ 7.45–7.20 (m, 10H), 4.50 (d, J=9.5 Hz, 1H), 4.44 (d, J=6.1 Hz, 1H), 4.08 (dd, J=13.5, 2.2 Hz, 1H), 3.98 (d, J=13.5 Hz, 1H), 3.88 (d, J=9.5 Hz, 1H), 3.58 (ddd, J=6.0, 2.0, 1.0 Hz, 1H), 2.98–2.81 (m, 4H). $^{13}$C NMR: δ 197.0, 136.2, 136.1, 131.1, 131.0, 128.2, 126.8, 114.0, 112.9, 104.0, 78.52, 75.87, 70.33, 60.30, 46.21, 43.94, 26.70, 26.09. Anal. Calcd. for $C_{24}H_{26}O_6$: C, 70.28; H, 6.38. Found: C, 70.18; H, 6.31.

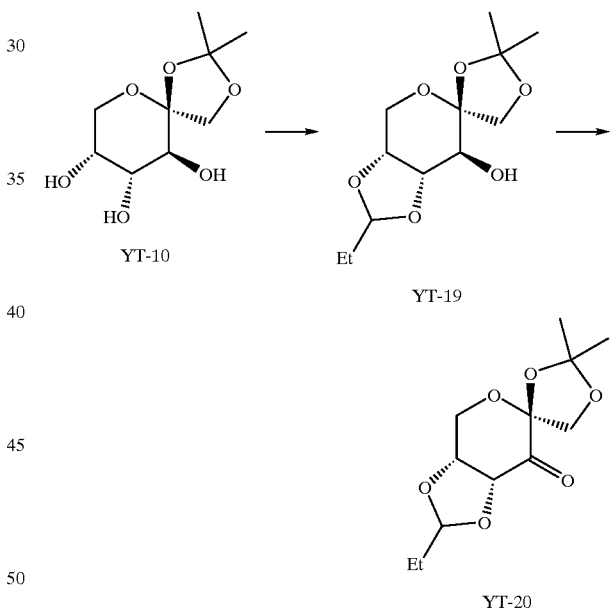

YT-10

YT-19

YT-20

Preparation of Ketone YT-20

To a mixture $CH(OMe)_3$ (2.2 mL, 2.22 g, 20 mmol), alcohol YT-10 (2.20 g, 10 mmol), and propanal (11.6 g, 200 mmol) in THF (40 mL) was added $TsOH.H_2O$ (0.5 g) at room temperature. After being stirred overnight, the reaction mixture was neutralized by with triethylamine, concentrated, and purified by flash chromatography (hexane:ether, 20:1 to 4:3, v/v) to give alcohol YT-19 as a white solid (1.20 g, 46%).

PCC (2.2 g, 10.3 mmol) was added portionwise over 15 min to a mixture of alcohol YT-19 (1.0 g, 3.8 mmol) and powdered 3A molecular sieves (4.4 g) in dichloromethane (20 mL). After being stirred for 3 hours under nitrogen, the reaction mixture was filtered through celite and silicon gel (lower layer) and washed carefully with hexane-ether (1:1, v/v), the filtrate was concentrated to afford YT-20 as a solid (0.83 g, 84%). $^1$H NMR: δ 5.02 (t, J=4.9 Hz, 1H), 4.69 (d, J=5.9 Hz, 1H), 4.60 (d, J=9.6 Hz, 1H), 4.49–4.04 (m, 3H), 3.99 (d, J=9.6 Hz, 1H), 1.82–1.62 (m, 2H), 1.55 (s, 3H), 1.40 (s, 3H), 0.97 (t, J=7.5 Hz ) $^{13}$C NMR: 196.4, 114.1, 107.0, 104.2, 79.61, 75.20, 70.29, 60.12, 27.60, 26.73, 26.19, 8.21. Anal. Calcd. for $C_{12}H_{18}O_6$: C, 55.81; H, 7.02. Found: C, 55.93; H, 7.11.

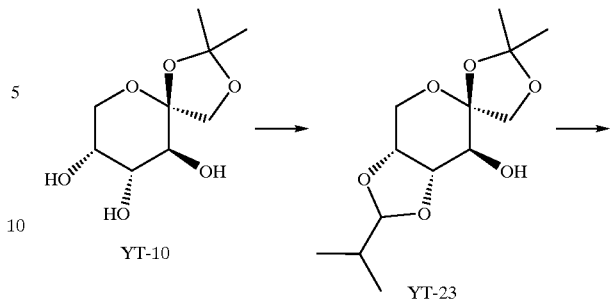

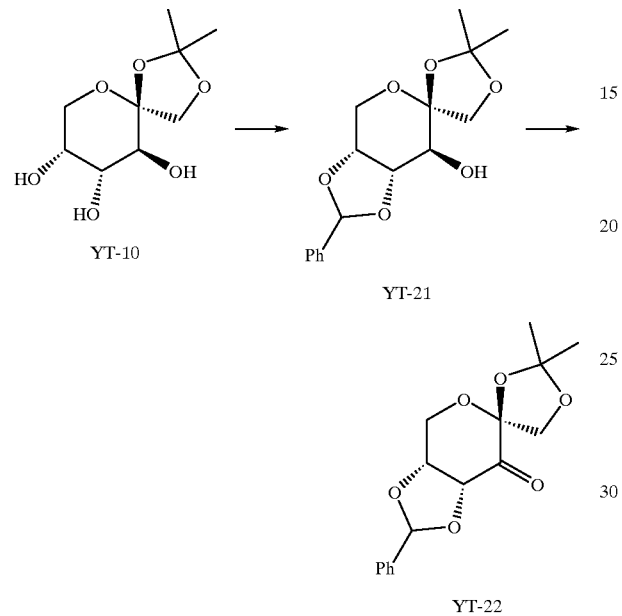

Preparation of Ketone YT-22

To a mixture $CH(OEt)_3$ (3 mL, 18 mmol) and $TsOH·H_2O$ (0.5 g) in dioxane (30 mL) was added benzaldehyde (15 mL) room temperature. After stirring for 1 hour, YT-10 (2.20 g, 10 mmol) was added. After 4 hours another patch of $CH(OEt)_3$ (2.0 mL, 12 mmol) was added. The reaction mixture was stirred for another 2 hours, neutralized with triethylamine (1 mL), concentrated, and purified by flash chromatography (hexane:ether, 20:1 to 3:2, v/v) to give alcohol YT-21 as a white solid (1.60 g, 52%).

PCC (1.9 g, 8.8 mmol) was added portionwise over 15 min to a mixture of alcohol YT-21 (1.0 g, 3.3 mmol) and powdered 3A molecular sieves (3.8 g) in dichloromethane (20 mL). After being stirred for 3 hours under nitrogen, the reaction mixture was filtered through celite and silicon gel (lower layer) and washed carefully with hexane:ether (1:1, v/v). The filtrate was concentrated to afford YT-22 as a solid (0.73 g, 74%). $^1$H NMR: δ 7.50 (m, 5H), 5.91 (s, 1H), 4.84 (d, J=6.1 Hz, 1H), 4.78–4.58 (m, 2H), 4.44 (d, J=13.8 Hz, 1H), 4.25 (d, J=13.8 Hz, 1H), 4.01 (d, J=9.1 Hz, 1H), 1.57 (s, 3H), 1.42 (s, 3H). $^{13}$C NMR: δ 196.0, 136.1, 130.0, 128.6, 127.3, 114.1, 105.4, 104.3, 80.13, 75.75, 70.45, 60.24, 26.73, 26.17. Anal. Calcd. for $C_{16}H_{18}O_6$: C, 62.74; H, 5.92. Found: C, 62.63; H, 6.00.

Preparation of Ketone YT-24

To a mixture $CH(OEt)_3$ (3 mL, 18 mmol) and $TsOH·H_2O$ (0.2 g) in dioxane (30 mL) at 0° C. was added isobutanal (30 mL) room temperature. After stirring for 1 hour, YT-10 (2.2 g, 10 mmol) was added. After 4 hours, another patch of $CH(OEt)_3$ (2.0 mL, 12 mmol) was added. The reaction mixture was stirred for another 2 hours, neutralized with triethylamine (1 mL), concentrated, and purified by flash chromatography (hexane:ether, 20:1 to 3:2, v/v) to give alcohol YT-23 as a white solid (1.48 g, 54%).

PCC (1.93 g, 9.0 mmol) was added portionwise over 15 min to a mixture of alcohol YT-23 (0.91 g, 3.3 mmol) and powdered 3A molecular sieves (3.86 g) in dichloromethane (20 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-24 as a solid (0.64 g, 71%). 1H NMR: δ 4.77 (d, J=5.4 Hz, 1H), 4.66 (d, J=5.9 Hz, 1H), 4.57–4.36 (m, 2H), 4.16 (d, J=13.4 Hz, 1H), 3.98 (d, J=9.5 Hz, 1H), 1.91–1.75 (m, 1H), 1.55 (s, 3H), 1.40 (s, 3H), 0,99 (d, J=6.9 Hz, 3H), 0.94 (d, J=6.9 Hz, 3H). $^{13}$C NMR: δ 196.3, 114.0, 109.8, 104.2, 79.33, 75.07, 70.38, 60.24, 32.31, 26,73, 26.17, 17,14, 16,94. Anal. Calcd. for $C_{13}H_{20}O_6$: C, 57.34; H, 7.43. Found: C, 57.28; H, 7.42.

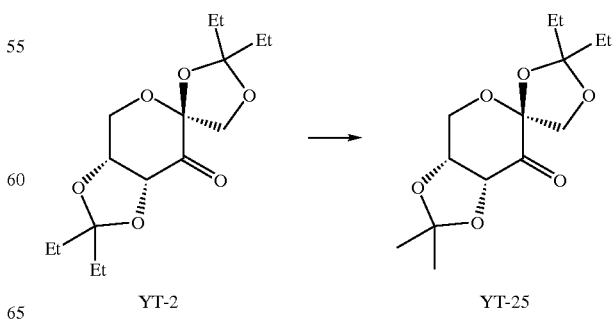

Preparation of Ketone YT-25

TsOH.H$_2$O (0.6 g) was added to a solution of ketone YT-2 (1.47 g, 5.7 mmol) in acetone (60 mL). After being stirred for 0.5 hour at room temperature, 2,2-dimethoxypropane (2.0 mL, 1.69 g, 16 mmol) was added. The mixture was stirred at room temperature for 3.5 hours, neutralized with triethylamine, concentrated, and purified by flash chromatography (hexane:ether, 15:1 to 10:1, v/v) to afford YT-25 as a syrup (0.62 g, 46.0%). $^1$H NMR: δ 4.76 (d, J=5.5 Hz, 1H), 4.63 (d, J=9.4 Hz, 1H), 4.56 (ddd, J=5.5, 2.2, 0.9 Hz, 1H), 4.42 (dd, J=13.5, 2.2 Hz, 1H), 4.13 (d, J=13.5 Hz, 1H), 3.96 (d, J=9.4 Hz, 1H), 1.86 (q, J=7.4, 2H), 1.63 (q, J=7.4, 2H), 1.46 (s, 3H), 1.40 (s, 3H), 0.96 (t, J=7.4 Hz, 3H), 0.82 (t, J=7.4 Hz, 3H). $^{13}$C NMR: δ 197.0, 118.3, 110.7, 104.3, 78.11, 76.05, 70.36, 60.34, 30.12, 29.06, 27.32, 26.23, 8.42, 7.75. Anal. Calcd. for C$_{14}$H$_{22}$O$_6$: C, 58.73; H, 7.74. Found: C, 58.81; H, 7.80.

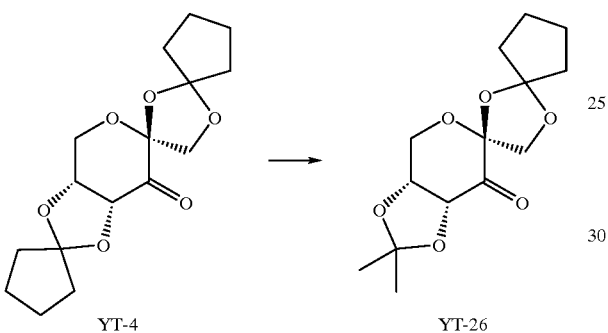

YT-4 → YT-26

Preparation of Ketone YT-26

TsOH.H$_2$O (0.25 g) was added to a solution of ketone YT-4 (0.62 g, 2.0 mmol) in acetone (30 mL). After being stirred for 0.5 hour at room temperature, 2,2-dimethoxypropane (1.0 mL, 0.84 g, 8 mmol) was added. The mixture was stirred at room temperature for 3.5 hours, neutralized with triethylamine, concentrated, and purified by chromatography to give YT-26 as a solid (0.30 g, 52%). $^1$H NMR: δ 4.74 (d, J=5.6 Hz, 1H), 4.56–4.54 (m, 2H), 4.38 (dd, J=9.4 Hz, 1H), 4.13 (d, J=13.5 Hz, 1H), 3.90 (d, J=9.4 Hz, 1H), 1.97–1.67 (m, 10H), 1.46 (s, 3H), 1.40 (s, 3H). $^{13}$C NMR: δ 197.2, 123.3, 110.9, 104.0, 78.16, 76.11, 70.17, 60.57, 36.93, 36.22, 27.37, 26.28, 23.96, 23.26. Anal. Calcd. for C13H$_{20}$O$_6$: C, 59.14; H, 7.09. Found: C, 58.95; H, 7.28.

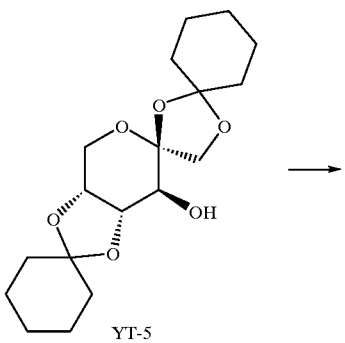

YT-5

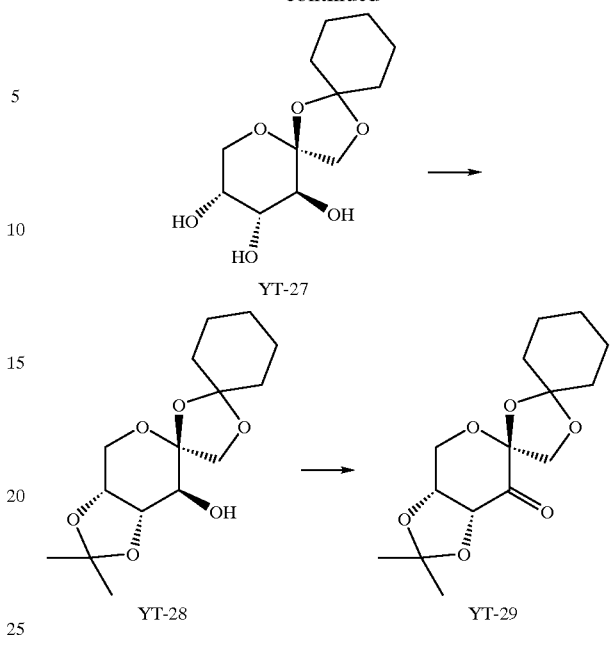

YT-27 → YT-28 → YT-29

Preparation of Ketone YT-29

To a solution of alcohol YT-5 (5.10 g, 15 mmol) in acetonitrile-water (100 mL, 9:1, v/v) was added DDQ (0.64 g, 3 mmol). After being stirred at room temperature for 3 hours, the reaction mixture was concentrated to a reddish residue. After being washed with ethyl acetate, the residue was dried under vacuum to give a reddish solid (YT-27) (2.19 g) which could be directly used for next reaction.

To a mixture of alcohol YT-27 (2.91 g), 2,2-dimethoxypropane (2.0 mL, 18 mmol), cupric sulfate (5.0 g) and acetone (40 mL) was added con. sulfuric acid (0.06 g). After being stirred for 1.5 hour at room temperature, the reaction mixture was neutralized with triethylamine (1 mL) and filtered. The filtrate was concentrated and purified by flash chromatography (hexane:ether, 10:1 to 3:2) to afford YT-28 as a solid (1.92 g, 76%).

PCC (3.05 g, 14.1 mmol) was added portionwise over 15 min to a mixture of alcohol YT-28 (1.57 g, 5.2 mmol) and powdered 3A molecular sieves (7.1 g) in dichloromethane (30 mL). After being stirred for 3 hours under nitrogen, the reaction mixture was diluted with hexane (50 mL), filtered through celite, and washed carefully with ether. The filtrate was concentrated and purified by passing through a short silica gel column (hexane:ether, 20:1 to 8:1, v/v) to afford YT-29 as a white solid (1.26 g, 80.8%). $^1$H NMR: δ 4.76 (d, J=5.6 Hz, 1H), 4.60 (d, J=9.5 Hz, 1H), 4.56 (ddd, J=5.6, 2.2, 0.9 Hz, 1H), 4.41 (dd, J=13.5, 2.2 Hz, 1H), 4.12 (dd, J=13.5, 0.9 Hz, 1H), 3.99 (d, J=9.5 Hz, 1H), 1.80 (t, J=6.1, 2H), 1.70–1.40 (m, 8H), 1.64 (s, 3H), 1.40 (s, 3H). $^{13}$C NMR: δ 197.2, 114.9, 110.8, 104.0, 78.17, 76.13, 69.81, 60.34, 36.39, 35.54, 27.38, 26.29, 25.09, 24.17, 23.93. Anal. Calcd. for C$_{15}$H$_{22}$O$_6$: C, 60.39; H, 7.43. Found: C, 60.50; H, 7.52.

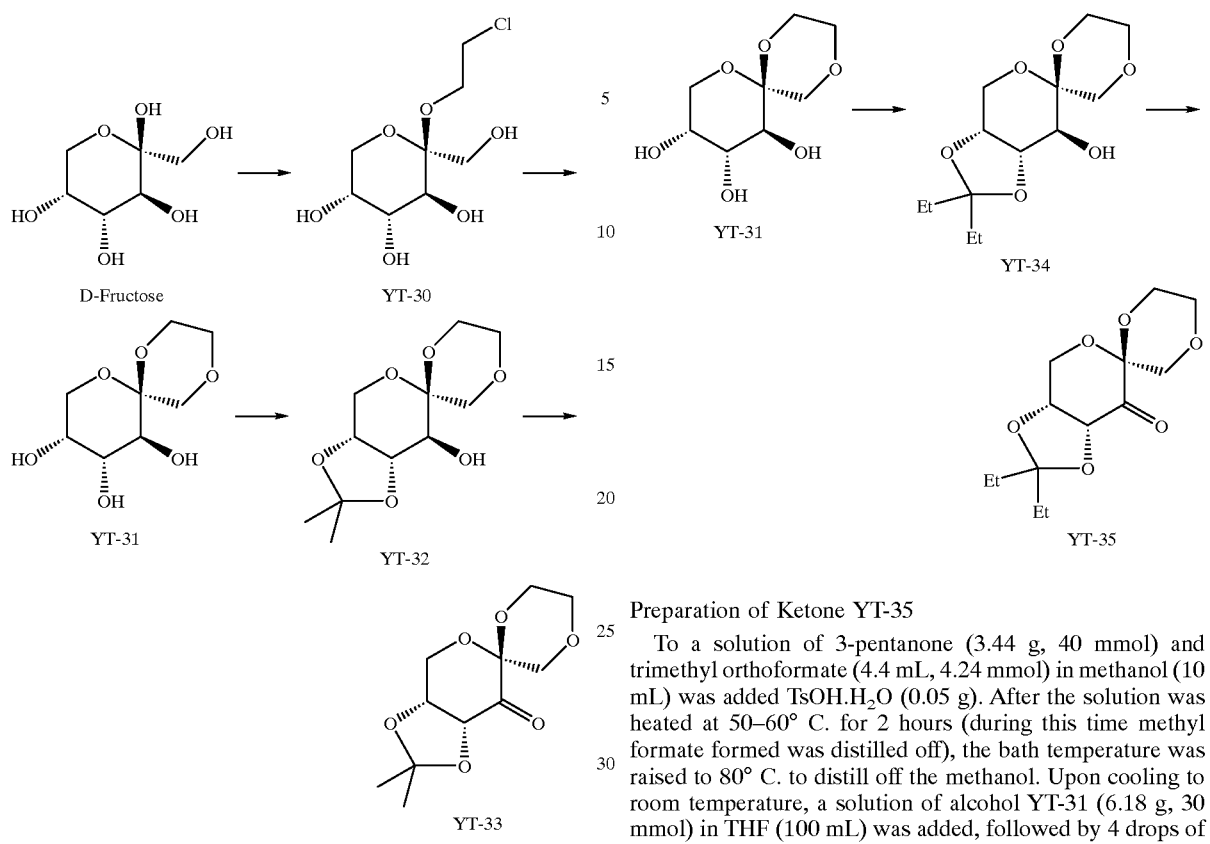

Preparation of Ketone YT-33

Perchloric acid (70%) (1 mL) was added to a mixture of alcohol YT-31(10.08 g, 52 mmol) (for preparation see J. Y. C. Chan, P. P. L. Cheong, L. Hough, and A. C. Richardson, *J. Chem. Soc. Perkin Trans.* I, 1985, 1447) and 2,2-dimethoxypropane (8.0 mL, 65 mmol) in acetone (100 mL) at 0° C. After being stirred under nitrogen at the temperature overnight, the reaction mixture was neutralized with con. NH$_4$OH solution, and concentrated. The resulting residue was dissolved in dichloromethane (100 mL), washed with brine, dried with sodium sulfate, concentrated, and purified with flash chromatography (ethyl acetate:hexane, 3:1 to 1:1, v/v) to give alcohol YT-32 as a solid (4.22 g, 35.3%).

PCC (5.82 g, 27 mmol) was added portionwise over 15 min to a mixture of alcohol YT-32 (2.46 g, 10 mmol) and powdered 3A molecular sieves (11 g) in dichloromethane (50 mL). After being stirred overnight under nitrogen, the reaction mixture was filtered through celite and washed carefully with ether. The filtrate was concentrated and purified by passing through a short silica gel column (hexane:ether, 1:1, v/v) to afford YT-33 as a white solid (2.04 g, 83.6%). $^1$H NMR: δ 4.73 (d, J=5.7 Hz, 1H), 4.58 (ddd, J=5.7, 2.0, 1.2 Hz, 1H), 4.24–4.02 (m, 3H), 3.90 (d, J=12.6 Hz, 1H), 3.82–3.59 (m, 4H), 1.45 (s, 3H), 1.38 (s, 3H). $^{13}$C NMR: δ 199.3, 110.7, 93.94, 78.72, 75.70, 67.23, 65.58, 60.49, 59.42, 27.36, 26.28. Anal. Calcd. for C$_{11}$H$_{14}$O$_6$: C, 54.09; H, 6.60. Found: C, 53.91; H, 6.89.

Preparation of Ketone YT-35

To a solution of 3-pentanone (3.44 g, 40 mmol) and trimethyl orthoformate (4.4 mL, 4.24 mmol) in methanol (10 mL) was added TsOH.H$_2$O (0.05 g). After the solution was heated at 50–60° C. for 2 hours (during this time methyl formate formed was distilled off), the bath temperature was raised to 80° C. to distill off the methanol. Upon cooling to room temperature, a solution of alcohol YT-31 (6.18 g, 30 mmol) in THF (100 mL) was added, followed by 4 drops of 70% perchloric acid. After being stirred at room temperature overnight, the reaction mixture was neutralized with con. NH$_4$OH and concentrated. The resulting residue was dissolved in dichloromethane (200 mL), washed with brine, dried over sodium sulfate, concentrated, and purified by flash chromatography (hexane:ether, 20:1 to 3:2, v/v) to give alcohol YT-34 as a solid (5.08 g, 61.8%).

PCC (10.52 g, 48.8 mmol) was added portionwise over 15 min to a mixture of alcohol YT-34 (5.00 g, 27.4 mmol) and powdered 3A molecular sieves (8.02 g) in dichloromethane (50 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-35 as a white solid (3.98 g, 79.0%). $^1$H NMR: δ 4.67 (dd, J=6.1, 1.1 Hz, 1H), 4.60 (ddd, J=6.1, 2.8, 1.5 Hz, 1H), 4.17 (s, 2 Hz, 1H), 4.05 (dtq, J=11.2, 3.2, 1.5 Hz, 1H), 3.92 (dd, J=12.3, 1.8 Hz, 1H), 3.82–3.58 (m, 4H), 1.64 (m, 4H), 0.91 (m, 6H). $^{13}$C NMR: δ 199.2, 114.8, 93.94, 78.18, 75.29, 67.31, 65.58, 60.38, 59.65, 29.87, 29,12, 8.583, 8,389. Anal. Calcd. for C$_{13}$H$_{20}$O$_6$: C, 57.34; H, 7.40. Found: C, 57.58; H, 7.45.

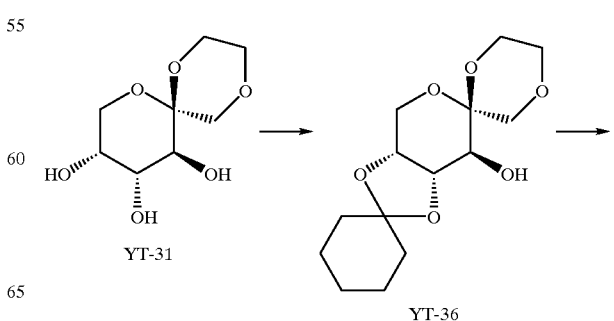

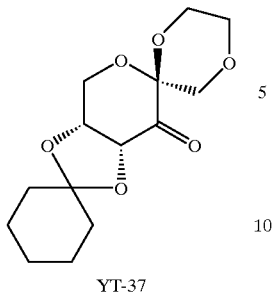

YT-37

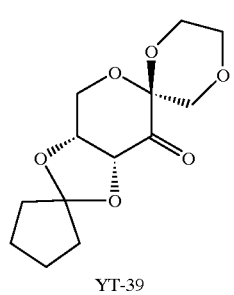

YT-39

Preparation of Ketone YT-37

To a solution of cyclohexanone (5.88 g, 60 mmol) and trimethyl orthoformate (4.4 mL, 4.24 mmol) in methanol (20 mL) was added TsOH.H$_2$O (0.05 g). After the solution was heated at 50–60° C. for 3 hours (during this time methyl formate formed was distilled off), the bath temperature was raised to 80° C. to distill off the methanol. Upon cooling to room temperature, a solution of alcohol YT-31 (8.24 g, 40 mmol) in THF (100 mL) was added, followed by 4 drops of 70% perchloric acid. After being stirred at room temperature for 5 hours, the reaction mixture was neutralized con. NH$_4$OH and concentrated. The resulting residue was dissolved in dichloromethane (150 mL), washed with brine, dried over sodium sulfate, concentrated, and purified by flash chromatography (hexane:ether, 10:1 to 5:2, v/v) to give alcohol YT-36 as a solid (7.64 g, 66.3%).

PCC (10.52 g, 48.8 mmol) was added portionwise over 15 min to a mixture of alcohol YT-36 (5.76 g, 20 mmol) and powdered 3A molecular sieves (9.92 g) in dichloromethane (100 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-37 as a white solid (4.98 g, 86.5%). $^1$H NMR: δ 4.73 (d, J=5.6 Hz, 1H), 4.59 (d, J=5.6 Hz, 1H), 4.19 (d, J=1.4, 2H), 4.10–3.60 (m, 7H), 1.62 (m, 8H), 1.40 (bs, 2H). $^{13}$C NMR: δ 199.5, 111.3, 93.93, 78.26, 75,28, 67.25, 65.55, 60.42, 59.53, 36.91, 35.61, 25.07, 24.05, 23.90. Anal. Calcd. . for C$_{14}$H$_{20}$O$_6$: C, 59.14; H, 7.09. Found: C, 59.21; H, 7.03.

Preparation of Ketone YT-39

To a solution of cyclopetanone (5.04 g, 60 mmol) and trimethyl orthoformate (4.4 mL, 4.24 g, 40 mmol) in methanol (20 mL) was added TsOH.H$_2$O (0.05 g). After the solution was heated at 50–60° C. for 3 hours (during this time methyl formate formed was distilled off), the bath temperature was raised to 80° C. to distill off the methanol. Upon cooling to room temperature, a solution of alcohol YT-31 (8.24 g, 40 mmol) in THF (100 mL) was added, followed by 4 drops of 70% perchloric acid. After being stirred at room temperature for 5 hours, the reaction mixture was neutralized with con. NH$_4$OH and concentrated. The resulting residue was dissolved in dichloromethane (150 mL), washed with brine, dried over sodium sulfate, concentrated, and purified by flash chromatography (hexane:ether, 10:1 to 5: 2, v/v) to give alcohol YT-38 as a solid (5.97 g, 51.8%).

PCC (9.92 g, 46 mmol) was added portionwise over 15 min to a mixture of alcohol YT-38 (5.48 g, 20 mmol) and powdered 3A molecular sieves (20 g) in dichloromethane (100 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-39 as a white solid (4.29 g, 78%). $^1$H NMR: δ 4.73 (d, J=5.8 Hz, 1H), 4.46 (ddd, J 5.7, 1.8, 0.6 Hz, 1H), 4.25–4.03 (m, 8H), 2.05–1.61 (m, 8H). $^{13}$C NMR: δ 198.8, 120.3, 93.85, 78.97, 75.40, 67.16, 65.55, 60.45, 59.34, 37.47, 23.71, 23.40. Anal. Calcd. for C$_{13}$H$_{18}$O$_6$: C, 57.77; H, 6.71. Found: C, 57.62; H, 6.81.

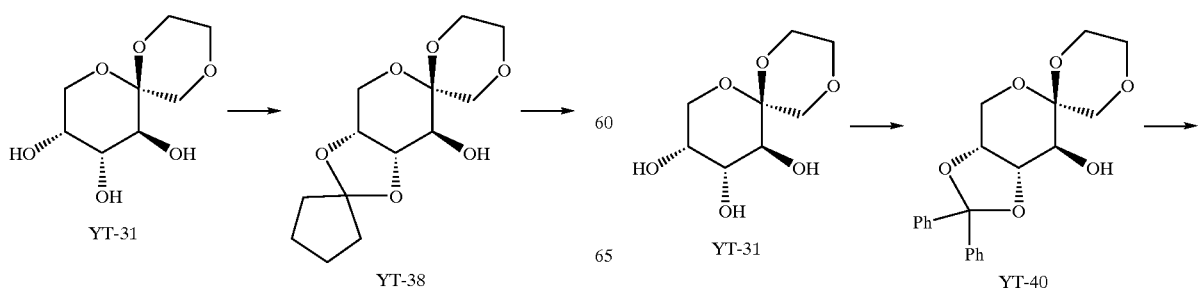

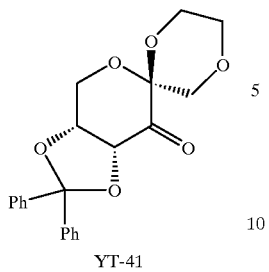

YT-41

Preparation of ketone YT-41

To a solution of benzophenone (4.86 g, 30 mmol) and trimethyl orthoformate (3.1 mL, 30 mmol) in methanol (20 mL) was added TsOH.H$_2$O (0.02 g). After the solution was heated at 50–60° C. for 3 hours (during this time methyl formate formed was distilled off), the bath temperature was raised to 100° C. to distill off the methanol. Upon cooling to room temperature, a solution of alcohol YT-31 (6.18 g, 30 mmol) in THF (150 mL) was added, followed by 3 drops of 70% perchloric acid. After being stirred at room temperature overnight, the reaction mixture was neutralized with con. NH$_4$OH and concentrated. The resulting residue was dissolved in dichloromethane (150 mL), washed with brine, dried over sodium sulfate, concentrated, and purified by flash chromatography (hexane:ether, 10:1 to 5:2, v/v) to give alcohol YT-40 as a solid (7.24 g, 67%).

PCC (4.0 g, 18.6 mmol) was added portionwise over 15 min to a mixture of alcohol YT-40 (2.79 g, 8.1 mmol) and powdered 3A molecular sieves (80 g) in dichloromethane (80 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-41 as a white solid (1.43 g, 51%). $^1$H NMR: δ 7.6–7.2 (m, 10H), 4.79 (d, J=6.6 Hz, 1H), 4.53 (dd, J=6.4, 1.8 Hz, 1H), 4.32 (d, J=13.4, 1H), 4.18 (dd, J=13.4, 2.4 Hz, 1H), 4.07 (dt, J=11.2, 3.2 Hz, 1H), 3.85 (d, J=12.4 Hz, 1H), 3.80–3.57 (m, 4H); $^{13}$C NMR: δ 197.8, 141.9, 140.9, 128.8, 128.5, 128.4, 128.2, 126.5, 110.8, 94.17, 78.58, 75.63, 67.47, 65.60, 60.44, 59.55. Anal. Calcd. for C$_{21}$H$_{20}$O$_6$: C, 68.47; H, 5.47. Found: C, 68.34; H, 5.85.

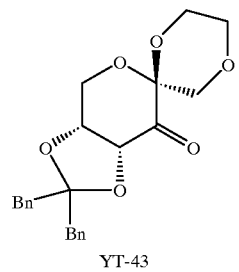

YT-43

Preparation of ketone YT-43

To a solution of 1,3-diphenylacetone (2.1 g, 10 mmol) and trimethyl orthoformate (1.2 mL, 11 mmol) in methanol (10 mL) was added TsOH.H$_2$O (0.01 g). After the solution was heated at 50–60° C. for 3 hours (during this time methyl formate formed was distilled off), the bath temperature was raised to 90° C. to distill off the methanol. Upon cooling to room temperature, a solution of alcohol YT-31 (3.10 g, 15 mmol) in THF (100 mL) was added, followed by 3 drops of 70% perchloric acid. After being stirred at room temperature overnight, the reaction mixture was neutralized with con. NH$_4$OH and concentrated. The resulting residue was dissolved in dichloromethane (150 mL), washed with brine, dried over sodium sulfate, concentrated, and purified by flash chromatography (hexane:ether, 10:1 to 5:2, v/v) to give alcohol YT-42 (2.36 g, 59.2%).

PCC (2.34 g, 10.4 mmol) was added portionwise over 15 min to a mixture of alcohol YT-42 (1.8 g, 4.5 mmol) and powdered 3A molecular sieves (5.0 g) in dichloromethane (50 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-43 as a solid (1.68 g, 93%). $^1$H NMR: δ 7.45–7.20 (m, 10H), 4.45 (d, J=6.3 Hz, 1H), 4.07–3.61 (m, 8H), 3.54 (dd, J=11.1, 2.4 Hz, 1H), 2.98 (d, J=13.8 Hz, 1H), 2.93 (d, J=13.8 Hz, 1H), 2.91 (d, J=13.9 Hz, 1H), 2.82 (d, J=13.9 Hz, 1H ). $^{13}$C NMR: δ 198.9, 136.2, 136.0, 131.0, 130.9, 128.2, 128.1, 126.7, 112.5, 93.63, 79.03, 75.45, 66.99, 65.39, 60.22, 59.23, 46.13, 43.63, Anal. Calcd. for C$_{23}$H$_{24}$O$_6$: C, 69.68; H, 6.10. Found: C, 69.46; H, 5.88.

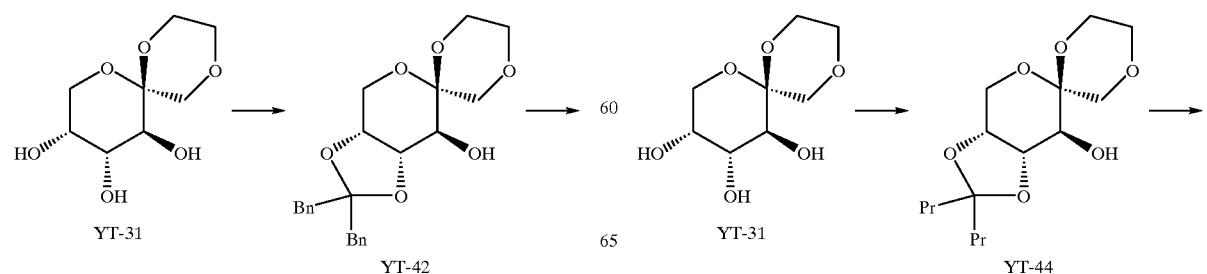

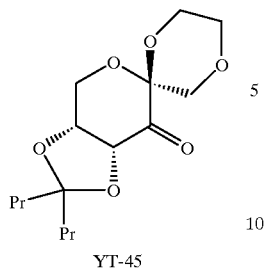

YT-45

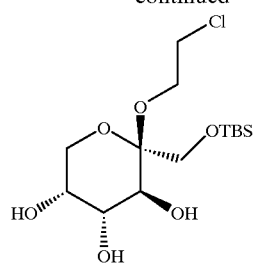

YT-46

Preparation of Ketone YT-45

To a solution of 4-heptanone (11.4 g, 100 mmol) and trimethyl orthoformate (4.24 g, 40 mmol) in methanol (50 mL) was added TsOH.H$_2$O (0.01 g). After the solution was heated at 50–70° C. for 2 hours (during this time methyl formate formed was distilled off), the bath temperature was raised to 100° C. to distill off the methanol. Upon cooling to room temperature, a solution of alcohol YT-31 (6.18 g, 30 mmol) in dioxane (60 mL) was added, followed by cupric sulfate (6.0 g) and 3 drops of con. sulfuric acid. After being stirred at room temperature overnight, the reaction mixture was neutralized with con. NH$_4$OH and concentrated. The resulting residue was dissolved in dichloromethane (150 mL), washed with brine, dried over sodium sulfate, concentrated, and purified by flash chromatography (hexane:ether, 50:1 to 3:1, v/v) to give alcohol YT-44 as a syrup (5.56 g, 46.0%).

PCC (9.12 g, 42.3 mmol) was added portionwise over 15 min to a mixture of alcohol YT-44 (4.73 g, 15.7 mmol) and powdered 3A molecular sieves (18.24 g) in dichloromethane (100 mL). After being stirred for 3 h under nitrogen, the reaction mixture was filtered through celite and washed carefully with ether. The filtrate was concentrated and purified by passing through a short silica gel column (hexane:ether, 1:1, v/v) to afford YT-45 as a syrup (3.89 g, 83%). 1H NMR: δ 4.66 (d, J=6.1 Hz, 1H), 4.50 (ddd, J=5.2, 1.5, 1.5 Hz, 1H), 4.17 (d, J=1.5 Hz, 2H), 4.06 (dt, J=11.1, 3.2 Hz, 1H), 3.92 (d, J=12.4 Hz, 1H), 3.82–3.60 (m, 4H), 1.62–1.26 (m, 8H), 0.912 (t, J=7,3 Hz, 3H), 0.907 (t, J=7.2 Hz, 3H). $^{13}$C NMR: δ 199.2, 114.1, 94.03, 78.09, 75.26, 67.42, 65.62, 60.62, 59.74, 39.89, 39.22, 17.65, 17.44, 14.55. Anal. Calcd. for C$_{13}$H$_{24}$O$_6$: C, 69.68; H, 6.10. Found: C, 69.46; H, 5.88.

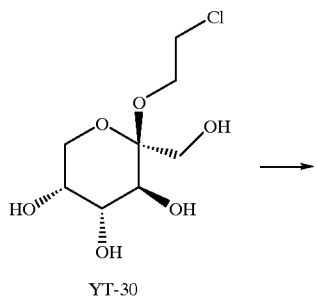

YT-30

Preparation of Ketone YT-48 t-Butyldimethylsilyl chloride (22.61 g, 150 mmol) was added to a mixture alcohol YT-30 (36.32 g, 150 mmol), DMAP (1.0 g), and imidazole (10.8 g, 150 mmol) in DMF (200 mL) at room temperature. After being stirred overnight, the reaction mixture was concentrated to give a residue. The residue was treated with ethyl acetate (400 mL). After filtration, the filtrate was dried over sodium sulfate, concentrated to give alcohol YT-46 as a syrup.

The syrup was mixed with acetone (800 mL), 2,2-dimethoxypropane (70 mL, mmol), cupric sulfate (180 g), and con. sulfuric acid (2.8 g). After being stirred at room temperature for 40 min, the reaction mixture was neutralized with triethylamine, filtered, and concentrated. The resulting residue was dissolved in ethyl acetate (300 mL), washed with brine, dried over sodium sulfate, concentrated, and purified with flash chromatography (hexane:ether, 100:0 to 10:1, v/v) to give alcohol YT-47 as a syrup (21.28 g, 35.8%).

PCC (27.82 g, 129 mmol) was added portionwise over 15 min to a mixture of alcohol YT-47 (20.25 g, 51 mmol) and powdered 3A molecular sieves (44.5 g) in dichloromethane (100 mL). After being stirred for 3 h under nitrogen, the reaction mixture was filtered through celite and washed carefully with ether. The filtrate was concentrated and the purified by passing through a short silica gel column (hexane:ether, 1:1, v/v) to afford YT-48 as a syrup (15.86 g, 78.7%). $^1$H NMR: δ 4.85 (d, J=5.8 Hz, 1H), 4.59 (dd, J=5.8, 2.1 Hz, 1H), 4.38 (dd, J=13.4, 2.1 Hz, 1H), 4.08–3.70 (m. 7H), 1.48 (s, 3H), 1.38 (s, 3H), 0.87 (s, 9H), 0.092 (s, 3H), 0.085 (s, 3H). $^{13}$C NMR: δ 198.7, 110.5, 99.53, 78.79, 76.12, 63.07, 61.53, 60.01, 43.29, 27.36, 26.24, 25.99, 18.47, −5.29, −5.41. Anal. Calcd. for C$_{17}$H$_{29}$O$_6$ClSi: C, 51.69; H, 7.91. Found: C, 51.90; H, 8.03.

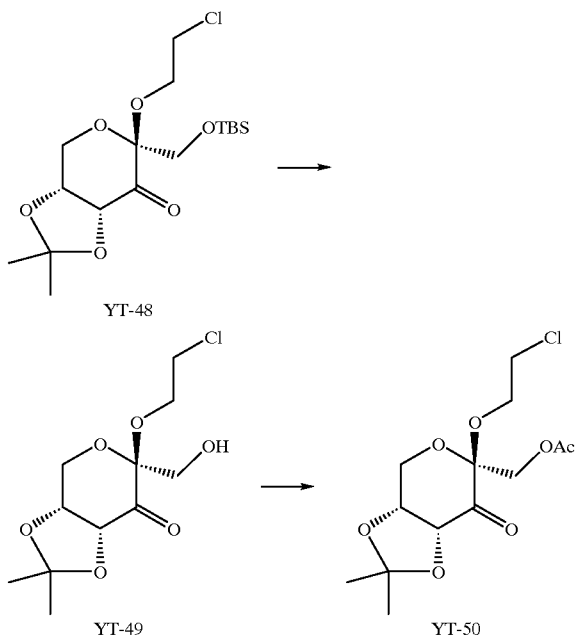

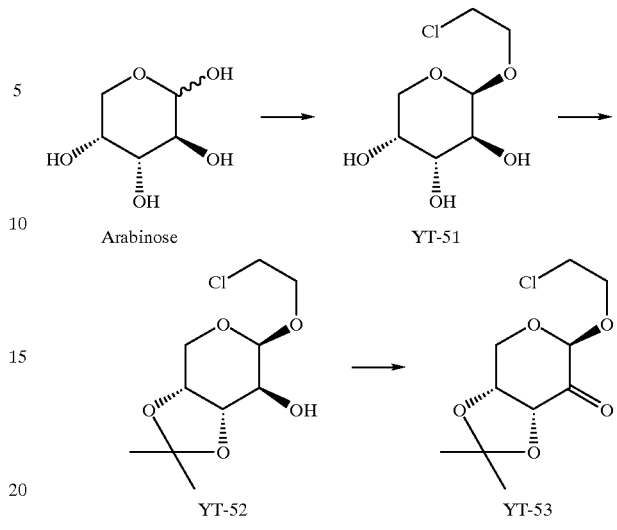

Preparation of Ketone YT-49 and Ketone YT-50

To a solution of ketone YT-48 (1.98 g, 50 mmol) in pyridine (2 mL) and water (2 mL) was added TBAF (10 mL, 1 M in THF). After being stirred at room temperature for 15 min, the reaction mixture was poured into water (10 mL), extracted with chloroform, washed with brine, dried over sodium sulfate, concentrated, and purified with a flash chromatography (hexane:ether, 10:1 to 1:1, v/v) to give ketone YT-49 (0.90 g, 64%). IR: 3511 cm$^{-1}$. $^1$H NMR: δ 4.82 (d, J=5.6 Hz, 1H), 4.58 (ddd, J=5.6, 2.2, 1.0 Hz, 1H), 4.50 (dd, J 13.3, 2.2 Hz, 1H), 4.12 (d, J=13.3 Hz, 1H), 4.03 (dt, J 10.5, 4.3 Hz, 1H), 3.96–3.70 (m, 5H), 3.75 (dd, J=4.4, 1.0 Hz, 1H), 3.73 (d, J=4.3 Hz, 1H), 2.23 (bs, 1H), 1.46 (s, 3H), 1.40 (s, 3H). $^{13}$C NMR: δ 201.4, 110.6, 98.91, 78.11, 75.63, 62.84, 61.08, 59.67, 43.15, 27.36, 26.21. Anal. Calcd. for $C_{11}H_{17}O_6Cl$: C, 47.1; H, 6.1. Found: C, 46.98; H, 6.18.

To a mixture of ketone YT-49 (1.40 g, 5 mmol), DMAP (0.20 g), and pyridine (6 mL) in dichloromethane (15 mL) was added acetic anhydride (4.0 mL, mmol). After being stirred overnight, the reaction mixture was poured into ice-water (20 mL), extracted with dichloromethane, washed with brine, dried over sodium sulfate, concentrated, and purified with a flash chromatography to give ketone YT-50 as a syrup (0.89 g, 49.2%). IR: 1752 cm$^{-1}$. $^1$H NMR: δ 4.82 (d, J=5.9 Hz, 1H), 4.60 (ddd, J=5.9, 2.0, 0.9 Hz, 1H), 4.43 (d, J=12.3 Hz, 1H), 4.40 (dd, J=13.5, 2.0 Hz, 1H), 4.32 (d, J=12.3 Hz, 1H), 4.13 (d, J=13.5, 1H), 3.98–3.70 (m, 4H), 2.08 (s, 3H), 1.47 (s, 3H), 1.40 (s, 3H). $^{13}$C NMR: δ 198.1, 170.3, 110.8, 98.81, 78.05, 75.63, 62.87, 60.76, 60.00, 42.94, 27.24, 26.21, 20.94. Anal. calcd. for $C_{13}H_{19}O_7Cl$: C, 48.38; H, 5.93. Found: C, 48.45; H, 6.23.

Preparation of Ketone YT-53

D-Arabinose (10 g, 66.7 mmol) was added to 2-chloroethanol (50 mL) (containing 1.5 mL of AcCl). After being stirred at 50° C. for 24 hours, the reaction mixture was cooled down in a refrigerator. The resulting suspension was filtered and the cake was washed with ethanol to give alcohol YT-51 as a white solid (7.42 g, 57.8%).

Con. sulfuric acid (0.1 g) was added to a mixture of 2-chloroethyl arabinoside YT-51 (6.02 g, 31 mmol), 1,1-dimethoxypropane (5 mL, 4.25 g, 41 mmol), and $CuSO_4$ (10 g) in acetone (100 mL ). After being stirred overnight, the reaction mixture was filtered. The filtrate was concentrated and purified by chromatography (hexane:ether, 20:1 to 2:1, v/v)to give alcohol YT-52 as a white solid (5.87 g, 81%).

PCC (13.58 g, 63 mmol) was added portionwise over 15 min to a mixture of alcohol YT-52 (5.87 g, 23.2 mmol) and powdered 3A molecular sieves (26 g) in dichloromethane (100 mL). After being stirred for 3 hours under nitrogen, the reaction mixture was filtered through celite and washed carefully with ether. The filtrate was concentrated and the purified by passing through a short silica gel column (hexane:ether, 1:1, v/v) and subsequent recrystallization (diisopropyl ether) to give ketone YT-53 as a white solid (1.63 g, 28%). $^1$H NMR: δ 4.87 (s, 1H), 4.72 (d, J=5.6 Hz, 1H), 4.56 (ddd, J=5.6, 2.1, 0.9 Hz, 1H), 4.39 (dd, J=13.4, 2.1 Hz, 1H), 4.10 (d, J=13.4 Hz, 1H), 4.03 (dt, J=11.0, 5.9 Hz, 1H), 3.85 (dt, J=11.0, 4.9 Hz, 1H), 3.70 (dd, J=5.9, 4.9 Hz, 2H), 1.47 (s, 3H), 1,40 (s, 3H). $^{13}$C NMR: δ 198.5, 110.8, 100.1, 77.66, 75.52, 68.81, 59.06, 42.67, 27.36, 26.31. Anal. Calcd. for $C_{10}H_{15}O_5Cl$: C, 47.91; H, 6.03. Found: C, 48.00; H, 6.24.

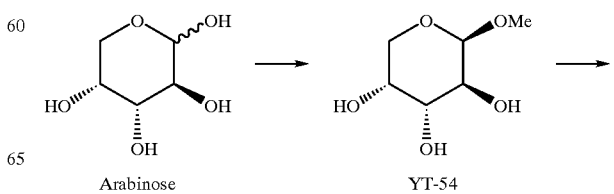

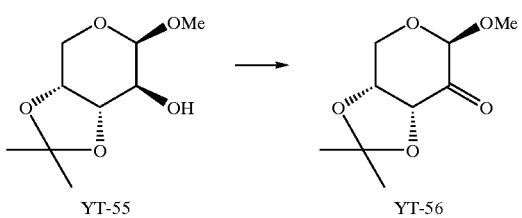

Preparation of Ketone YT-56

Ketone YT-56 was prepared based on a reported procedure (M. Bennett, G. B. Gill, G. Pattenden, A. J. Shucker, and A. Stapleton, *J. Chem. soc. Perkin Trans*. I, 1991, 929).

Kinetic Resolution of Compounds Containing an Olefin Moiety

This example illustrate the utility of using chiral ketones in resolving a racemic mixture of a variety of compounds containing an olefin moiety and a chiral center.

Table 3 shows some of the kinetic resolution results of a variety of racemic compounds using methods of the present invention.

TABLE 3

Kinetic Resolution of Olefins by Ketone 1 Catalyzed Asymmetric Epoxidation[a]

| entry | substrate | temp (° C.) | con.[h] (%) | recovered S.M. ee(%) | epoxide ee(%) | epoxide[m] (trans/cis) | $K_{rel}$[n] ($k_f/k_s$) |
|---|---|---|---|---|---|---|---|
| 1[c] | R = TMS | −10 | 50 | 96[i] | 95[i] | 70 | 153 |
| 2[e] | R = Me | −10 | 54 | 99[i] | 85[o] | ND | 60 |
| 3[f] | R = COMe | 0 | 52 | 96[j] | 88[l] | 12 | 42 |
| 4[g,q] | R = COOEt | −10 | 49 | 94[i] | 97[l] | 22 | 203 |
| 5[d] | R = TBS | −10 | 55 | 99[i] | 81[p] | 6 | 51 |
| 6[b] | R = Me | −10 | 61 | 95[i] | ND | 6 | 14 |
| 7[b] | CH(CO2Me)2 | 0 | 72 | 81[j] | ND | 1.7 | 4 |
| 8[b] | R = TBS | −10 | 49 | 75[k] | ND | 13 | 18 |
| 9[b] | R = TBS | 20 | 66 | 96[k] | ND | 8 | 11 |
| 10[b] | R = TMS | 0 | 70 | 84[k] | ND | 2.6 | 5 |
| 11[c] | t-Bu | 0 | 63 | 90[j] | 53[o] | 25 | 9 |

TABLE 3-continued

Kinetic Resolution of Olefins by Ketone 1 Catalyzed Asymmetric Epoxidation[a]

| entry | substrate | temp (° C.) | con.[h] (%) | recovered S.M. ee(%) | epoxide ee(%) | epoxide[m] (trans/cis) | $K_{rel}$[n] ($k_f/k_s$) |
|---|---|---|---|---|---|---|---|
| 12[g] | (structure with OTMS and OPiv on cyclohexene) | −10 | 54 | 87[l] | 76[o] | 4 | 21 |

[a]All reactions were carried out with substrate (1 eq), ketone (0.25–0.60 eq), and Oxone (2.3 eq) in $CH_3CN$—DMM-0.05 M $Na_2B_4O_7 \cdot 10H_2O$ in aqueous EDTA (4 × $10^{-4}$ M) solution (1:2:2, v/v/v), unless otherwise noted.
[b]0.25 eq ketone was used.
[c]0.35 eq ketone was used.
[d]0.40 eq. ketone was used.
[e]0.45 eq ketone was used.
[f]0.50 eq ketone was used.
[g]0.60 eq ketone was used.
[h]The conversion was determined by $^1H$ NMR of the crude reaction mixture. In cases where the ee of the epoxide was determined, the conversion was cross-checked using the ee's of the olefin and epoxide using the following equation: ee(olefin)/ee(epoxide) = C/1 − C. In cases where the NMR conversion was different than the calculated conversion, the calculated conversion is reported.
[i]Enantioselectivity was determined by chiral HPLC (Chiralcel OD).
[j]Enantioselectivity was determined by chiral HPLC (Chiralcel OJ).
[k]Enantioselectivity was determined by chiral HPLC (Chiralcel OD) after desilylation with TBAE.
[l]Enantioselectivity was determined by chiral HPLC (Chiralcel AD).
[m]The ratio of trans and cis epoxides was determined by NMR integration.
[n]$K_{rel}$ was calculated from the conversion and ee of the starting material from the following equation: $K_{rel} = \ln[(1-C)(1-ee)]/\ln[(1-C)(1+ee)]$. Alternatively, $K_{rel}$ was calculated from the conversion and ee of the epoxide from the following equation: $K_{rel} \ln[1 - C(1 + ee)]/\ln[1 - C(1 - ee)]$. If both the olefin and epoxide ee have been determined, the value shown was calculated from the equation that provided the lower value.
[o]Enantioselectivity was determined by chiral shift NMR analysis using $Eu(hfc)_3$ as chiral shift reagent.
[p]Enantioselectivity was determined by chiral HPLC (Chiralcel AD) of the corresponding benzoate.
[q]2.8 eq Oxone was used.

General Method for Kinetic Resolution:

To a solution of 6-acetoxy-1-phenylcyclohexene (0.5 mmol) in $DMM/CH_3CN$ (15 mL, 2:1 v/v) was added $Na_2B_4O_7 \cdot 10H_2O$ buffer (0.05 M in 4×$10^{-4}$ M EDTA solution, 10 mL) and $Bu_4NHSO_4$ (15 mg). The mixture was cooled to −10° C. using an ice/salt bath and ketone catalyst (64 mg, 0.5 eq) was added. To this mixture was added Oxone (2.3 eq, as a solution in 4×$10^{-4}$ M EDTA, 9.8 mL) and aqueous $K_2CO_3$ (11 eq, in 9.8 mL $H_2O$) separately via syringe pump over 2.5 h. The reaction was quenched by the addition of hexane (20 mL), the layers were separated, and the organic layer was extracted with hexane (2×20 mL). The combined organics were washed with brine (1×50 mL), dried ($Na_2SO_4$), concentrated under reduced pressure, and purified by flash column chromatography (hexane/ethyl acetate, 60:1 v/v) to give recovered olefin (42% yield, 96% ee) and epoxide (32% yield, 88% ee) as colorless oils.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for increasing a relative concentration of at least one stereoisomer of a compound having at least one olefinic moiety, from a stereoisomer mixture of said compound, said method comprising contacting an oxidizing agent with a mixture comprising a chiral ketone and said stereoisomer mixture, wherein said method epoxidizes said olefinic moiety of said compound producing an epoxide of at least one stereoisomer of said compound at a relatively higher rate than an epoxide of another stereoisomer of said compound.

2. The method of claim 1, wherein said stereoisomer mixture comprises a geometrical isomer of said olefin moiety.

3. The method of claim 1, wherein said compound further comprises at least one chiral center.

4. The method of claim 3, wherein said stereoisomer mixture comprises a stereoisomer of said chiral center.

5. The method of claim 4, wherein said stereoisomer mixture is a racemic mixture.

6. The method of claim 4, wherein said method produces an enriched mixture of said compound, wherein said enriched mixture has at least about 50% enantiomeric excess.

7. The method of claim 1, wherein the ratio of said chiral ketone to said stereoisomer mixture is less than about 1:1.

8. The method of claim 1, wherein the ratio of said oxidizing agent to said chiral ketone is less than about 10:1.

9. The method of claim 1, wherein enantiomeric excess of said chiral ketone is at least about 90%.

10. The method of claim 1, wherein said chiral ketone is selected from the group consisting of compounds of the formula:

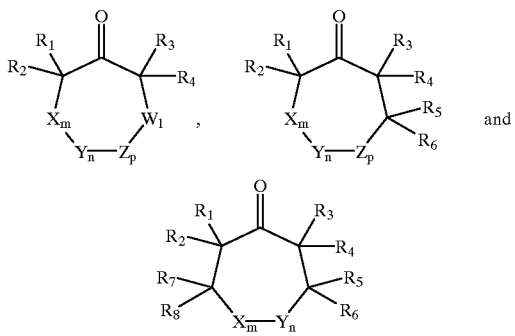

wherein
each of W, X, Y and Z is independently $CR_9R_{10}$, or O;
each of 1, m, n and p is independently an integer from 0 to 3;
each of $R_1$, $R_2$, $R_3$, $R_4$, $R_5$, $R_6$, $R_7$, $R_8$, $R_9$ and $R_{10}$ is independently hydrogen, halide, hydroxyl, nitro, thio, or alkyl, alkoxy, aryl, silyl, siloxy, carbonyl, carboxyl, ester, amino, sulfinyl, sulfonyl, sulfate, sulfite, phosphate or phosphite groups containing from 1 to about 20 carbon atoms, or two or more $R_1$, $R_2$, $R_3$, $R_4$, $R_5$, $R_6$, $R_7$, $R_8$, $R_9$ and $R_{10}$ are linked to form 3 to about 10 membered cyclic moiety containing 1 to about 20 carbon atoms; and
each of $R_{11}$ and $R_{12}$ is hydrogen, oxygen or alkyl, sulfonyl, alkoxy or carbonyl groups containing from 1 to about 20 carbon atoms, or $R_{11}$ and $R_{12}$ are linked to form 3 to about 10 membered cyclic moiety containing 1 to about 20 carbon atoms.

11. The method of claim 10, wherein said chiral ketone is a compound of the formula:

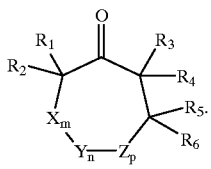

12. The method of claim 11, wherein m is 0, Y is O or $CR_9R_{10}$, n and p are 1, and Z is $CR_9R_{10}$.

13. The method of claim 12, wherein two or more $R_1$, $R_2$, $R_3$, $R_4$, $R_5$, $R_6$, $R_9$ and $R_{10}$ together form 3 to about 10 membered cyclic moiety containing 1 to about 20 carbon atoms.

14. The method of claim 13, wherein $R_1$ and $R_2$ together form a moiety of the formula:

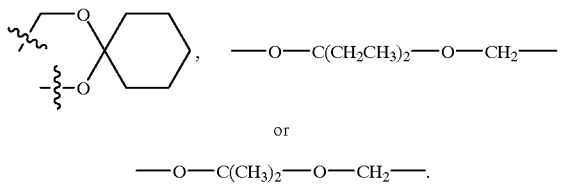

—O—C(CH$_2$CH$_3$)$_2$—O—CH$_2$— or —O—C(CH$_3$)$_2$—O—CH$_2$—.

15. The method of claim 14, wherein $R_1$ and $R_2$ together form a moiety of the formula:

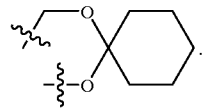

16. The method of claim 14, wherein $R_1$ and $R_2$ together form a moiety of the formula —O—C(CH$_3$)$_2$—O—CH$_2$— or —O—C(CH$_2$CH$_3$)$_2$—O—CH$_2$—.

17. The method of claim 16, wherein $R_3$ and $R_6$ together form a moiety of the formula —O—C(CH$_3$)$_2$—O— or —O—C(CH$_2$CH$_3$)$_2$—O—.

18. The method of claim 12, wherein $R_4$, $R_5$, $R_9$ and $R_{10}$ are independently hydrogen, halide, or sulfinyl, alkoxy, carboxyl or alkyl groups having 1 to about 20 carbon atoms.

19. The method of claim 12 wherein said chiral ketone is derived from a group consisting of (D)-fructose, (L)-fructose, (D)-arabinose, (L)-arabinose and (L)-sorbose.

20. The method of claim 10, wherein said chiral ketone is of the formula:

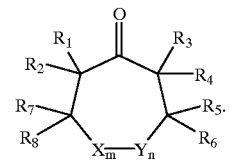

21. The method of claim 20, wherein m is 0, Y is $CR_9R_{10}$, and n is 1.

22. The method of claim 21 wherein two or more $R_1$, $R_2$, $R_3$, $R_4$, $R_5$, $R_6$, $R_7$, $R_8$, $R_9$ and $R_{10}$ together form 3 to about 10 membered cyclic moiety containing 1 to about 20 carbon atoms.

23. The method of claim 20, wherein $R_1$ and $R_7$ are linked to form a moiety of the formula —O—C(CH$_3$)$_2$—O— or —O—C(CH$_2$CH$_3$)$_2$—O—.

24. The method of claim 20, wherein $R_3$ and $R_6$ are linked to form a moiety of the formula —O—C(CH$_3$)$_2$—O— or —O—C(CH$_2$CH$_3$)$_2$O—.

25. The method of claim 24, wherein $R_1$ and $R_7$ are linked to form a moiety of the formula —C(CH$_3$)$_2$—.

26. The method of claim 21, wherein $R_4$, $R_5$, $R_9$ and $R_{10}$ are independently hydrogen, halide or alkoxy, sulfinyl, carboxyl or alkyl groups having 1 to about 20 carbon atoms.

27. The method of claim 20, wherein said chiral ketone is derived from quinic acid.

28. The method of claim 1, wherein said step of adding oxidizing agent to said mixture further comprises adding a base to said reaction solution.

29. The method of claim 28, wherein said base is added at a rate effective to maintain the pH of said mixture at from about pH 10 to about pH 14.

30. The method of claim 29, wherein said base is selected from the group consisting of potassium carbonate, potassium bicarbonate, sodium bicarbonate, sodium carbonate, sodium hydroxide, sodium borate, sodium phosphate, potassium phosphate, tetraalkylammonium hydroxide and potassium hydroxide.

31. The method of claim 1, wherein a reaction temperature of said epoxidation is less than about 30° C.

32. The method of claim 1, wherein said mixture further comprises a solvent selected from the group consisting of acetonitrile, dimethoxymethane, dimethoxyethane, water, dimethyl formamide, dioxane, and mixtures thereof.

33. The method of claim 1, wherein said oxidizing agent is selected from the group consisting of peracids, hydrogen peroxide, sodium hypochlorite, potassium peroxomonosulfate, sodium perborate, tetrabutylammonium monopersulfate and hypofluoride (HOF).

34. The method of claim 1, wherein said oxidizing agent is potassium peroxomonosulfate.

35. A method for increasing a relative concentration of at least one stereoisomer of a compound having at least one chiral center and at least one olefinic moiety, from a stereoisomer mixture of said compound, said method comprising contacting an oxidizing agent with a mixture comprising a chiral ketone and said stereoisomer mixture, wherein said method epoxidizes said olefinic moiety of said compound, producing an epoxide of at least one stereoisomer of said compound at a relatively higher rate than an epoxide of another stereoisomer of said compound.

36. The method of claim 35, wherein said stereoisomer mixture comprises a stereoisomer of said chiral center.

37. The method of claim 36, wherein said stereoisomer mixture is a racemic mixture.

38. The method of claim 36, wherein said method produces an enriched mixture of said compound, wherein said enriched mixture has at least about 50% enantiomeric excess.

39. The method of claim 35, wherein the ratio of said chiral ketone to said stereoisomer mixture is less than about 1:1.

40. The method of claim 35, wherein the ratio of said oxidizing agent to said chiral ketone is less than about 10:1.

41. The method of claim 35, wherein enantiomeric excess of said chiral ketone is at least about 90%.

42. The method of claim 35, wherein said chiral ketone is selected from the group consisting of compounds of the formula:

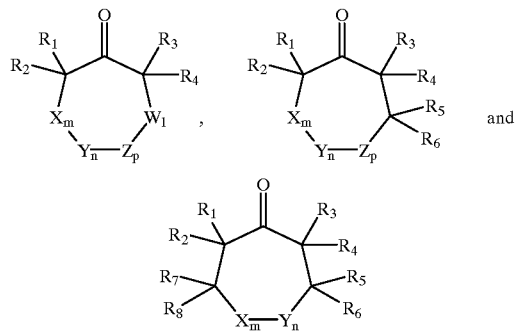

wherein
each of W, X, Y and Z is independently $CR_9R_{10}$, or O;
each of l, m, n and p is independently an integer from 0 to 3;
each of $R_1$, $R_2$, $R_3$, $R_4$, $R_5$, $R_6$, $R_7$, $R_8$, $R_9$ and $R_{10}$ is independently hydrogen, halide, hydroxyl, nitro, thio, or alkyl, alkoxy, aryl, silyl, siloxy, carbonyl, carboxyl, ester, amino, sulfinyl, sulfonyl, sulfate, sulfite, phosphate or phosphite groups containing from 1 to about 20 carbon atoms, or two or more $R_1$, $R_2$, $R_3$, $R_4$, $R_5$, $R_6$, $R_7$, $R_8$, $R_9$ and $R_{10}$ are linked to form 3 to about 10 membered cyclic moiety containing 1 to about 20 carbon atoms; and each of $R_{11}$ and $R_{12}$ is hydrogen, oxygen or alkyl, sulfonyl, alkoxy or carbonyl groups containing from 1 to about 20 carbon atoms, or $R_{11}$ and $R_{12}$ are linked to form 3 to about 10 membered cyclic moiety containing 1 to about 20 carbon atoms.

43. The method of claim 42, wherein said chiral ketone is a compound of the formula:

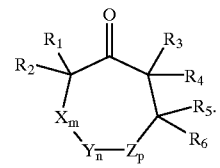

44. The method of claim 43, wherein m is 0, Y is O or $CR_9R_{10}$, n and p are 1, and Z is $CR_9R_{10}$.

45. The method of claim 44, wherein said chiral ketone is a compound of the formula:

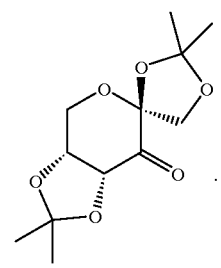

46. The method of claim 35, wherein said step of adding oxidizing agent to said mixture further comprises adding a base to said reaction solution.

47. The method of claim 46, wherein said base is added at a rate effective to maintain the pH of said mixture at from about pH 10 to about pH 14.

48. The method of claim 47, wherein said base is selected from the group consisting of potassium carbonate, potassium bicarbonate, sodium bicarbonate, sodium carbonate, sodium hydroxide, sodium borate, sodium phosphate, potassium phosphate, tetraalkylammonium hydroxide and potassium hydroxide.

49. The method of claim 35, wherein a reaction temperature of said epoxidation is less than about 30° C.

50. The method of claim 35, wherein said mixture further comprises a solvent selected from the group consisting of acetonitrile, dimethoxymethane, dimethoxyethane, water, dimethyl formamide, dioxane, and mixtures thereof.

51. The method of claim 35, wherein said oxidizing agent is selected from the group consisting of peracids, hydrogen peroxide, sodium hypochlorite, potassium peroxomonosulfate, tetrabutylammonium persulfate, sodium perborate and hypofluoride (HOF).

52. The method of claim 35, wherein said oxidizing agent is potassium peroxomonosulfate.

53. A method for increasing a relative concentration of at least one stereoisomer of a compound having at least one chiral center and at least one olefinic moiety, from a stereoisomer mixture of said compound, said method comprising contacting potassium peroxomonosulfate with a mixture comprising a chiral ketone of the formula:

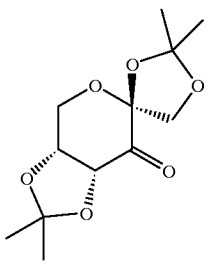

and said stereoisomer mixture, wherein said method epoxidizes said olefinic moiety of said compound producing an epoxide of at least one stereoisomer of said compound at a relatively higher rate than an epoxide of another stereoisomer of said compound.

54. The method of claim 53, wherein said stereoisomer mixture comprises a stereoisomer of said chiral center.

55. The method of claim 54, wherein said stereoisomer mixture is a racemic mixture.

56. The method of claim 54, wherein said method produces an enriched mixture of said compound, wherein said enriched mixture has at least about 50% enantiomeric excess.

57. The method of claim 53, wherein the ratio of said chiral ketone to said stereoisomer mixture is less than about 1:1.

58. The method of claim 53, wherein the ratio of said oxidizing agent to said chiral ketone is less than about 10:1.

59. The method of claim 53, wherein enantiomeric excess of said chiral ketone is at least about 90%.

60. The method of claim 53, wherein said step of adding oxidizing agent to said mixture further comprises adding a base to said reaction solution.

61. The method of claim 60, wherein said base is added at a rate effective to maintain the pH of said mixture at from about pH 10 to about pH 14.

62. The method of claim 61, wherein said base is selected from the group consisting of potassium carbonate, potassium bicarbonate, sodium bicarbonate, sodium carbonate, sodium hydroxide, sodium borate, sodium phosphate, potassium phosphate, tetraalkylammonium hydroxide and potassium hydroxide.

63. The method of claim 53, wherein a reaction temperature of said epoxidation is less than about 30° C.

64. The method of claim 53, wherein said mixture further comprises a solvent selected from the group consisting of acetonitrile, dimethoxymethane, dimethoxyethane, water, dimethyl formamide, dioxane, and mixtures thereof.

* * * * *